(12) United States Patent
Landis et al.

(10) Patent No.: US 11,458,270 B2
(45) Date of Patent: Oct. 4, 2022

(54) HIGH FLOW THERAPY DEVICE UTILIZING A NON-SEALING RESPIRATORY INTERFACE AND RELATED METHODS

(71) Applicant: ResMed Pty Ltd, Bella Vista (AU)

(72) Inventors: Robert M Landis, Mountainside, NJ (US); Charles A Lewis, Carrabelle, FL (US); Louis Javier Collazo, Pompano Beach, FL (US); Chris Agami, Coral Springs, FL (US)

(73) Assignee: ResMed Pty Ltd

( * ) Notice: Subject to any disclaimer, the term of this patent is extended or adjusted under 35 U.S.C. 154(b) by 0 days.

(21) Appl. No.: 15/134,900

(22) Filed: Apr. 21, 2016

(65) Prior Publication Data

US 2016/0367779 A1    Dec. 22, 2016

Related U.S. Application Data

(63) Continuation-in-part of application No. 14/016,042, filed on Aug. 30, 2013, now Pat. No. 11,071,464,
(Continued)

(51) Int. Cl.
*A61M 16/06* (2006.01)
*A61M 16/16* (2006.01)
(Continued)

(52) U.S. Cl.
CPC ........ *A61M 16/0666* (2013.01); *A61J 7/0053* (2013.01); *A61M 16/0066* (2013.01);
(Continued)

(58) Field of Classification Search
CPC .............. A61M 16/00; A61M 16/0051; A61M 16/0057; A61M 16/0063; A61M 16/0066;
(Continued)

(56) References Cited

U.S. PATENT DOCUMENTS

| 3,181,895 A | 5/1965 | Cator |
| 3,295,521 A * | 1/1967 | Balch .................... A61M 16/06 |
| | | 128/206.28 |

(Continued)

FOREIGN PATENT DOCUMENTS

| DE | 3708146 A1 | 9/1988 |
| FR | 2827778 A1 | 1/2003 |

(Continued)

OTHER PUBLICATIONS

Final Office Action dated Dec. 14, 2020 for U.S. Appl. No. 14/016,042, 22 pages.
(Continued)

*Primary Examiner* — Annette Dixon
(74) *Attorney, Agent, or Firm* — Botos Churchill IP Law LLP

(57) ABSTRACT

A high flow therapy system for delivering heated and humidified respiratory gas to an airway of a patient, the system including a respiratory gas flow pathway for delivering the respiratory gas to the airway of the patient by way of a non-sealing respiratory interface; wherein flow rate of the pressurized respiratory gas is controlled by a microprocessor.

18 Claims, 42 Drawing Sheets

Related U.S. Application Data which is a continuation of application No. 11/999,675, filed on Dec. 6, 2007, now Pat. No. 8,522,782, which is a continuation-in-part of application No. 11/638,981, filed on Dec. 14, 2006, now Pat. No. 8,333,194, which is a continuation of application No. 11/520,490, filed on Sep. 12, 2006, now abandoned.

(51) Int. Cl.
| | | |
|---|---|---|
| *A61M 16/00* | (2006.01) | |
| *A61M 16/12* | (2006.01) | |
| *A61M 16/08* | (2006.01) | |
| *A61M 16/10* | (2006.01) | |
| *A61M 16/04* | (2006.01) | |
| *A61J 7/00* | (2006.01) | |
| *A61J 17/00* | (2006.01) | |
| *A61B 5/1455* | (2006.01) | |
| *A61B 5/087* | (2006.01) | |
| *A61B 5/08* | (2006.01) | |

(52) U.S. Cl.
CPC ...... *A61M 16/049* (2014.02); *A61M 16/0488* (2013.01); *A61M 16/0677* (2014.02); *A61M 16/085* (2014.02); *A61M 16/0858* (2014.02); *A61M 16/107* (2014.02); *A61M 16/1075* (2013.01); *A61M 16/122* (2014.02); *A61M 16/16* (2013.01); *A61M 16/161* (2014.02); *A61B 5/087* (2013.01); *A61B 5/0816* (2013.01); *A61B 5/14551* (2013.01); *A61J 17/001* (2015.05); *A61M 16/0816* (2013.01); *A61M 16/105* (2013.01); *A61M 16/109* (2014.02); *A61M 2016/0021* (2013.01); *A61M 2016/0027* (2013.01); *A61M 2016/0039* (2013.01); *A61M 2016/103* (2013.01); *A61M 2016/1025* (2013.01); *A61M 2202/0208* (2013.01); *A61M 2205/18* (2013.01); *A61M 2205/3334* (2013.01); *A61M 2205/3368* (2013.01); *A61M 2205/50* (2013.01); *A61M 2205/502* (2013.01); *A61M 2230/42* (2013.01)

(58) Field of Classification Search
CPC .......... A61M 16/0069; A61M 16/0488; A61M 16/049; A61M 16/0493; A61M 16/0666; A61M 16/0672; A61M 16/0677; A61M 16/08; A61M 16/0816; A61M 16/0825; A61M 16/0833; A61M 16/085; A61M 16/0858; A61M 16/101; A61M 16/105; A61M 16/107; A61M 16/1075; A61M 16/108; A61M 16/1085; A61M 16/109; A61M 16/1095; A61M 16/12; A61M 16/122; A61M 16/125; A61M 16/142; A61M 16/16; A61M 16/161; A61M 16/18; A61M 16/20; A61M 16/203; A61M 2016/0021; A61M 2016/0024; A61M 2016/0027; A61M 2016/0039; A61M 2016/1025; A61M 2016/103; A61M 2202/0208; A61M 2205/18; A61M 2205/3334; A61M 2205/3368; A61M 2205/3382; A61M 2205/3386; A61M 2205/3561; A61M 2205/3592; A61M 2205/3633; A61M 2205/3653; A61M 2205/42; A61M 2205/50; A61M 2205/502; A61M 2205/52; A61M 2205/581; A61M 2205/582; A61M 2205/583; A61M 2230/005; A61M 2230/42; A61M 2230/432; A61M 2230/435; A61M 2230/50; Y10S 261/31
USPC ............ 128/200.24, 200.26, 203.16, 203.17, 128/203.26, 203.27, 204.14, 204.17, 128/204.18, 204.21, 204.23, 206.29, 128/207.18; 261/DIG. 31; 600/561
See application file for complete search history.

(56) References Cited

U.S. PATENT DOCUMENTS

| | | | | |
|---|---|---|---|---|
| 3,807,445 | A | * | 4/1974 | McPhee ............ A61M 16/0051 137/557 |
| 3,863,630 | A | * | 2/1975 | Cavallo ............... A61M 16/202 128/203.27 |
| 3,864,440 | A | * | 2/1975 | Giocoechea .......... A62B 21/00 261/122.1 |
| 3,913,843 | A | * | 10/1975 | Cambio, Jr. ........... A61M 11/06 239/338 |
| 4,060,576 | A | | 11/1977 | Grant |
| 4,109,509 | A | | 8/1978 | Cramer et al. |
| 4,203,027 | A | | 5/1980 | Brickell et al. |
| 4,260,180 | A | | 4/1981 | Halushka et al. |
| 4,399,349 | A | | 8/1983 | Deming et al. |
| 4,444,183 | A | * | 4/1984 | Heckendorn ...... A61M 16/0627 128/204.18 |
| 4,535,767 | A | * | 8/1985 | Tiep ................. A61M 16/0666 128/205.17 |
| 4,621,632 | A | | 11/1986 | Bartels et al. |
| 4,682,010 | A | | 7/1987 | Drapeau et al. |
| 4,708,831 | A | | 11/1987 | Elsworth et al. |
| 4,722,334 | A | * | 2/1988 | Blackmer ................ A61D 7/04 128/203.16 |
| 4,753,233 | A | | 6/1988 | Grimes |
| 4,807,616 | A | | 2/1989 | Adahan |
| 4,838,258 | A | | 6/1989 | Dryden et al. |
| 4,913,140 | A | | 4/1990 | Orec et al. |
| 4,941,469 | A | | 7/1990 | Adahan |
| 4,967,744 | A | | 11/1990 | Chua |
| 5,031,612 | A | * | 7/1991 | Clementi .......... A61M 16/1075 128/204.14 |
| 5,099,836 | A | | 3/1992 | Rowland et al. |
| 5,139,741 | A | | 8/1992 | Hagiwara |
| 5,195,515 | A | | 3/1993 | Levine |
| 5,226,411 | A | | 7/1993 | Levine |
| 5,237,987 | A | | 8/1993 | Anderson et al. |
| 5,239,994 | A | | 8/1993 | Atkins |
| 5,284,160 | A | | 2/1994 | Dryden |
| 5,394,881 | A | | 3/1995 | Block |
| 5,445,143 | A | | 8/1995 | Sims |
| 5,495,848 | A | | 3/1996 | Aylsworth et al. |
| 5,503,146 | A | * | 4/1996 | Froehlich .......... A61M 16/0051 128/202.22 |
| 5,551,419 | A | | 9/1996 | Froehlich et al. |
| 5,588,423 | A | | 12/1996 | Smith |
| 5,682,877 | A | * | 11/1997 | Mondry ................ A61M 16/10 128/204.22 |
| 5,692,497 | A | | 12/1997 | Schnitzer et al. |
| 5,720,276 | A | | 2/1998 | Kobatake et al. |
| 5,743,253 | A | | 4/1998 | Castor et al. |
| 5,752,506 | A | | 5/1998 | Richardson |
| 5,832,919 | A | * | 11/1998 | Kano ................... A61G 10/005 128/205.26 |
| 5,868,133 | A | * | 2/1999 | DeVries .............. A61M 16/125 128/204.18 |
| 5,950,621 | A | | 9/1999 | Klockseth et al. |
| 5,954,050 | A | | 9/1999 | Christopher |
| 6,010,118 | A | | 1/2000 | Milewicz |
| 6,093,169 | A | | 7/2000 | Cardoso |
| 6,150,661 | A | | 11/2000 | McCaul et al. |
| 6,155,986 | A | | 12/2000 | Brydon et al. |
| 6,213,955 | B1 | | 4/2001 | Karakasoglu et al. |
| 6,272,933 | B1 | * | 8/2001 | Gradon .................. G08B 21/16 73/861 |
| 6,349,724 | B1 | * | 2/2002 | Burton ............... A61M 16/0057 128/204.18 |
| 6,516,800 | B1 | | 2/2003 | Bowden |
| 6,533,984 | B2 | | 3/2003 | Curti |

(56) References Cited

U.S. PATENT DOCUMENTS

| | | | |
|---|---|---|---|
| 6,536,432 B2 | 3/2003 | Truschel | |
| 6,571,794 B1 | 6/2003 | Hansen | |
| 6,595,215 B2 | 7/2003 | Wood | |
| 6,626,175 B2 | 9/2003 | Jafari et al. | |
| 6,655,385 B1 | 12/2003 | Curti et al. | |
| 7,007,692 B2 | 3/2006 | Aylsworth et al. | |
| 7,007,694 B2 | 3/2006 | Aylsworth et al. | |
| 7,043,979 B2 | 5/2006 | Smith et al. | |
| 7,051,733 B2 | 5/2006 | Gradon et al. | |
| 7,086,399 B2 | 8/2006 | Makinson et al. | |
| 7,106,955 B2 | 9/2006 | Thudor et al. | |
| 7,114,497 B2 | 10/2006 | Aylsworth et al. | |
| 7,152,604 B2 | 12/2006 | Hickle et al. | |
| 7,380,551 B2 | 6/2008 | Alvey | |
| 7,520,277 B1* | 4/2009 | Grady | A61M 16/0833 128/201.23 |
| 7,543,584 B2 | 6/2009 | Brookman | |
| 8,220,458 B2 | 7/2012 | Landis et al. | |
| 8,267,084 B2 | 9/2012 | Kwok | |
| 8,333,194 B2* | 12/2012 | Lewis | A61J 11/0005 128/200.24 |
| RE44,453 E | 8/2013 | Virr et al. | |
| 8,522,782 B2 | 9/2013 | Lewis et al. | |
| 9,427,547 B2* | 8/2016 | Landis | A61J 11/0005 |
| 10,449,320 B2 | 10/2019 | Miller et al. | |
| 10,617,835 B2 | 4/2020 | Schermeier et al. | |
| 10,737,049 B1 | 8/2020 | Orr et al. | |
| 10,828,482 B2 | 11/2020 | Osborne et al. | |
| 11,071,464 B2 | 7/2021 | Landis et al. | |
| 2001/0017134 A1 | 8/2001 | Bahr | |
| 2002/0005201 A1 | 1/2002 | Gradon et al. | |
| 2002/0053286 A1 | 5/2002 | Czabala | |
| 2002/0053345 A1* | 5/2002 | Jafari | A61M 16/026 128/204.23 |
| 2002/0053346 A1 | 5/2002 | Curti et al. | |
| 2002/0100320 A1 | 8/2002 | Smith et al. | |
| 2003/0111079 A1* | 6/2003 | Matthews | A61M 16/026 128/204.18 |
| 2003/0111080 A1 | 6/2003 | Olsen et al. | |
| 2004/0065335 A1 | 4/2004 | Huber et al. | |
| 2004/0182392 A1 | 9/2004 | Gerder et al. | |
| 2005/0076906 A1* | 4/2005 | Johnson | A61M 16/0051 128/204.21 |
| 2005/0178383 A1 | 8/2005 | Mackie et al. | |
| 2005/0199242 A1 | 9/2005 | Matula et al. | |
| 2006/0042631 A1 | 3/2006 | Martin et al. | |
| 2006/0118111 A1 | 6/2006 | Pelerossi et al. | |
| 2006/0219245 A1 | 10/2006 | Holder | |
| 2007/0107737 A1 | 5/2007 | Landis et al. | |
| 2007/0169776 A1* | 7/2007 | Kepler | A61M 16/109 128/200.23 |
| 2007/0175473 A1 | 8/2007 | Lewis et al. | |
| 2008/0051674 A1* | 2/2008 | Davenport | A61B 5/087 600/561 |
| 2008/0142019 A1 | 6/2008 | Lewis et al. | |
| 2008/0308100 A1 | 12/2008 | Pujol et al. | |
| 2009/0101147 A1 | 4/2009 | Landis et al. | |
| 2013/0340752 A1 | 12/2013 | Landis et al. | |
| 2016/0367776 A1* | 12/2016 | Landis | A61J 11/0005 |
| 2016/0367779 A1 | 12/2016 | Landis et al. | |
| 2017/0304570 A1 | 10/2017 | Landis et al. | |
| 2021/0353158 A1 | 11/2021 | Landis et al. | |
| 2021/0353159 A1 | 11/2021 | Landis et al. | |

FOREIGN PATENT DOCUMENTS

| | | |
|---|---|---|
| WO | 2004105846 A2 | 12/2004 |
| WO | 2004112873 A1 | 12/2004 |
| WO | 2005011785 A1 | 2/2005 |
| WO | 2005018724 A1 | 3/2005 |
| WO | 2005055809 A2 | 6/2005 |
| WO | 2006056445 A1 | 6/2006 |
| WO | 2006125252 A1 | 11/2006 |
| WO | 2006126900 A1 | 11/2006 |

OTHER PUBLICATIONS

International Search Report and Written Opinion for International Application No. PCT/US2007/025085, dated Apr. 24, 2008, 8 pages.

International Search Report and Written Opinion from PCT/US2006/035947, dated Apr. 13, 2007, 15 pages.

Non Final Office Action dated Dec. 2, 2021 for U.S. Appl. No. 17/387,505.

Notice of Allowance dated Mar. 15, 2022 for U.S. Appl. No. 17/387,538.

Non Final Office Action dated Nov. 15, 2021 for U.S. Appl. No. 17/387,538.

International Search Report from PCT/US2006/035947 dated Dec. 22, 2006.

Final Office Action dated Dec. 24, 2020 for U.S. Appl. No. 14/016,042.

* cited by examiner

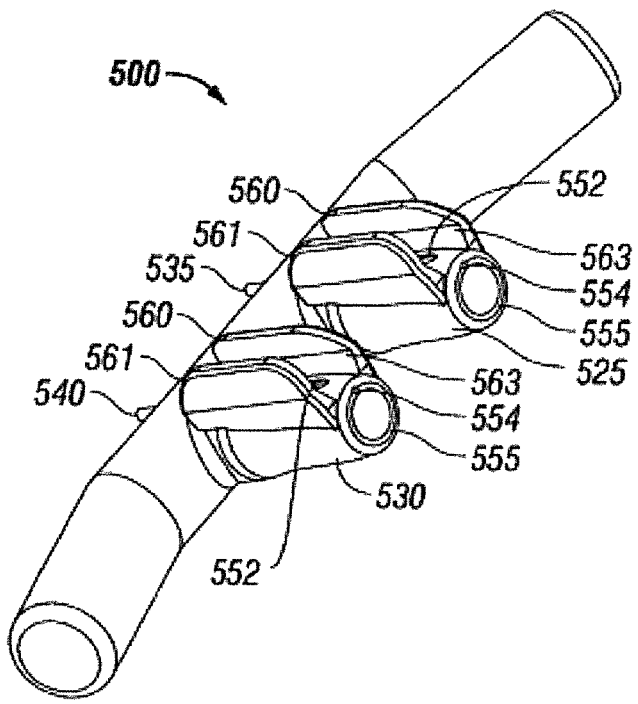
FIG. 5
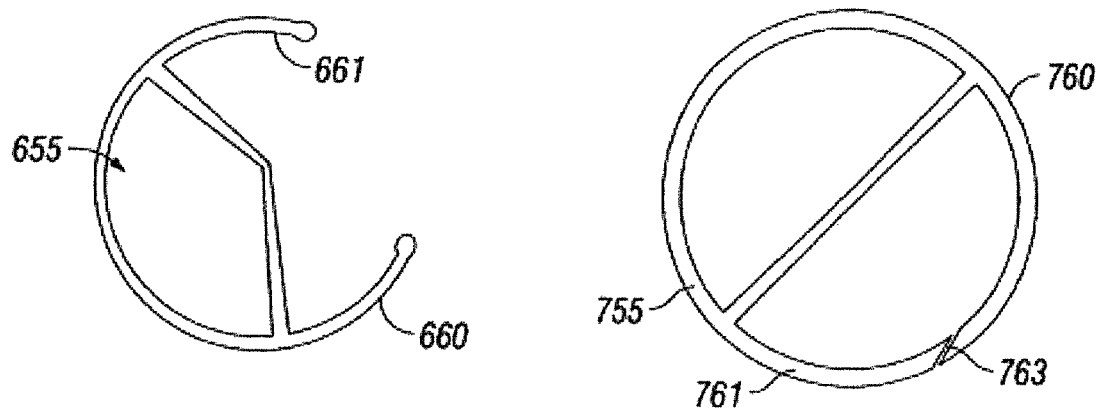
FIG. 6
FIG. 7

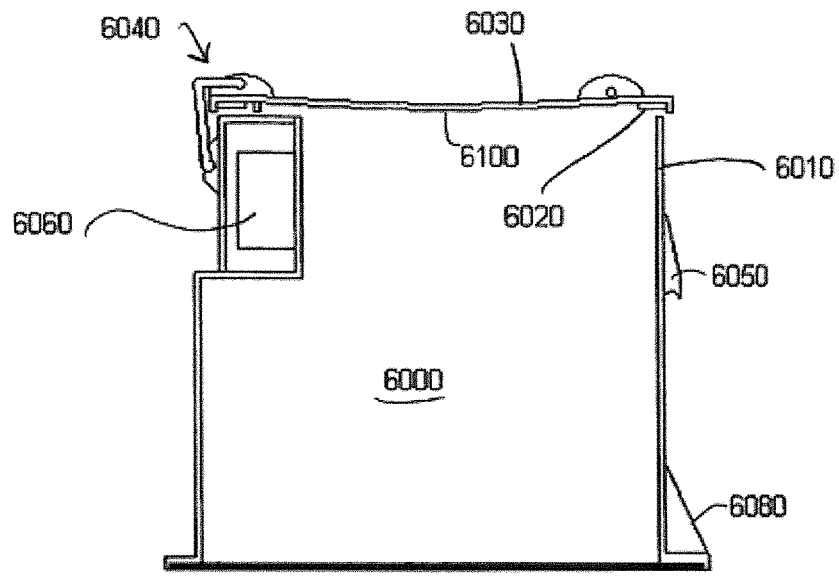
FIG. 33A
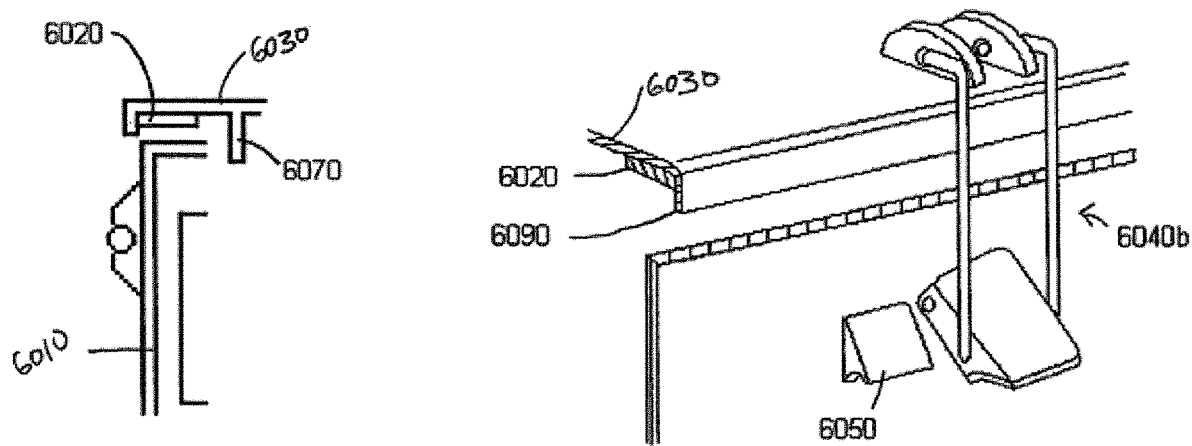
FIG. 33B
FIG. 33C

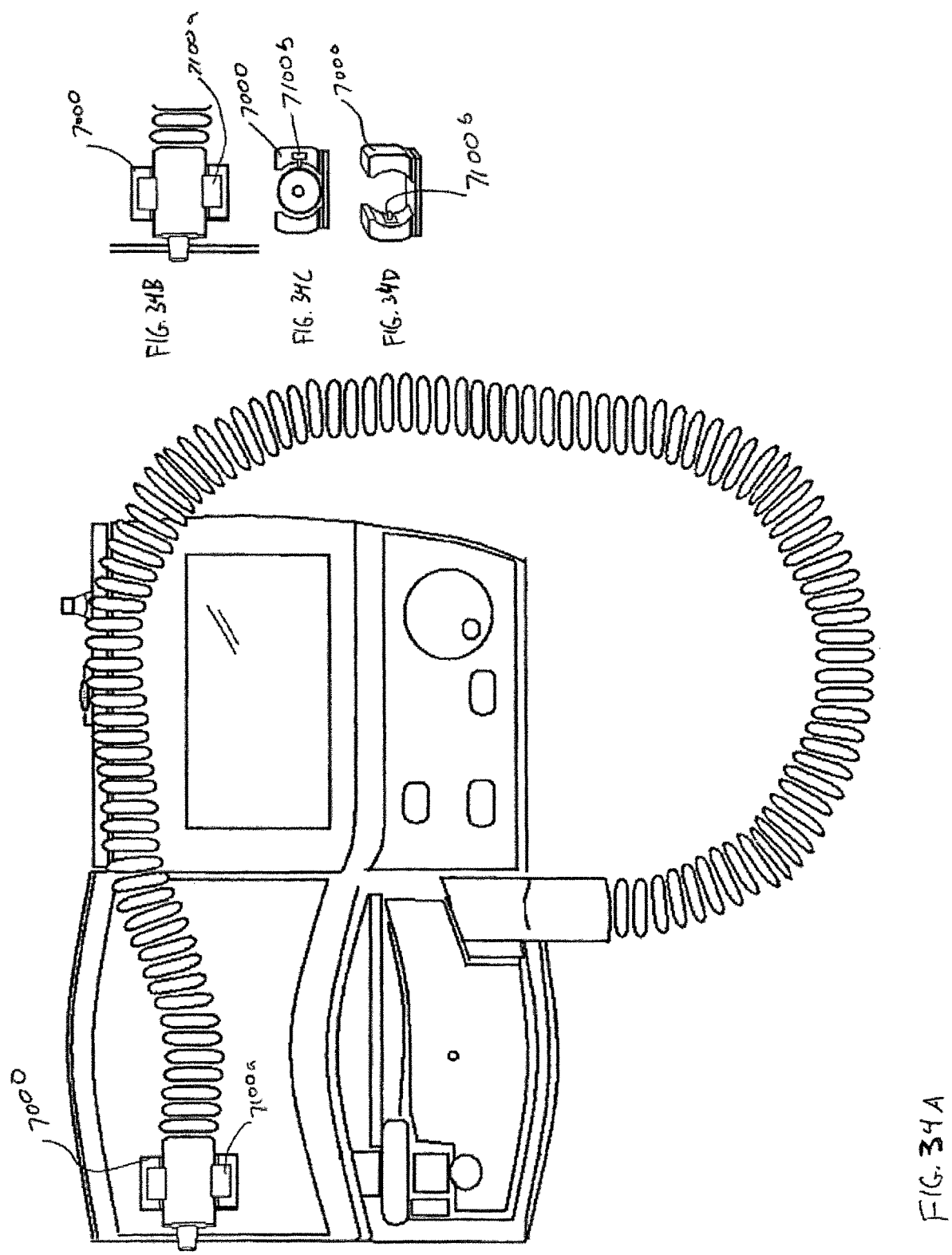

HIGH FLOW THERAPY DEVICE UTILIZING A NON-SEALING RESPIRATORY INTERFACE AND RELATED METHODS

CROSS-REFERENCE TO RELATED APPLICATIONS

This application is a continuation-in part-application of U.S. patent application Ser. No. 14/016,042, filed on Aug. 30, 2013 which is a continuation application of U.S. patent application Ser. No. 11/999,675, filed on Dec. 6, 2007, which is now U.S. Pat. No. 8,522,782 and issued Sep. 3, 2013, which is a continuation-in-part application of U.S. patent application Ser. No. 11/638,981, filed on Dec. 14, 2006, which is now U.S. Pat. No. 8,333,194 and issued Dec. 18, 2012, which is a continuation-in-part application of U.S. patent application Ser. No. 11/520,490, filed on Sep. 12, 2006, which claims the benefit of U.S. Provisional Patent Application Ser. No. 60/716,776, filed Sep. 12, 2005. U.S. patent application Ser. No. 11/638,981 also claims the benefit and priority of U.S. Provisional Patent Application Ser. No. 60/750,063, filed on Dec. 14, 2005; U.S. Provisional Patent Application Ser. No. 60/792,711, filed on Apr. 18, 2006; and U.S. Provisional Patent Application Ser. No. 60/852,851, filed on Oct. 18, 2006. The entire contents of each of these applications are hereby incorporated by reference herein.

BACKGROUND

In respiratory medicine, ventilation devices are typically used to deliver respiratory gases for therapeutic effect. Ventilators have been used with invasive patient interface, such as endotracheal tubes. Bi-level, Bi-PAP, and CPAP devices have been used with non-invasive patient interfaces, such as respiratory masks. When an option, non-invasive respiratory systems are preferred for increased patient comfort and reduced risks. Non-invasive ventilation (NIV) systems such as Bi-Level PAP (positive airway pressure) require the use of a sealed patient interface, such as a full face mask. Systems with patient interface that seal on the patient (i.e. closed systems) can generate higher pressures with low flows or non-continuous flows. Sealed patient interfaces are not as comfortable or easy to apply as non-sealed patient interface, such as nasal cannulas. However, non-sealing nasal cannulas do not work properly with NIV systems. Nasal cannulas are typically used with basic oxygen delivery systems that have flow limitations for various reasons. There is a need for a respiratory gas delivery system that works optimally with non-sealing patient interfaces to produce therapeutic effects to the patient similar to that of NIV systems. Because the system has a non-sealing patient interface and therefore some gas and pressure is lost to atmosphere, this respiratory gas delivery system must be able to deliver gas at high flows that are high enough to generate positive pressure in the patient's airway.

Respiratory interfaces, e.g., nasal cannulas are used to deliver respiratory gases for therapeutic effect, including oxygen therapy, treatment for sleep apnea, and respiratory support. Small nasal cannulas are commonly used for delivery of low volumes of oxygen. Sealing nasal cannulas, such as the cannulas disclosed in U.S. Pat. No. 6,595,215 to Wood, are used for the treatment of sleep apnea. However, treatment with certain types of nasal cannulas may be limited by the lack of information available on important treatment parameters. These parameters include information regarding the gases within the user's upper airway, such as pressure, flow rate, and carbon dioxide buildup. These and other data may be useful in judging the efficacy of treatment as well as for controlling and monitoring treatment.

In addition, prior art nasal cannula designs (especially those designed for neonatal oxygen therapy) may undesirably create a seal with the user's nares, which may have detrimental effects on the user's health.

Oxygen ($O_2$) therapy is often used to assist and supplement patients who have respiratory impairments that respond to supplemental oxygen for recovery, healing and also to sustain daily activity.

Nasal cannulas are generally used during oxygen therapy. This method of therapy typically provides an air/gas mixture including about 24% to about 35% $O_2$ at flow rates of 1-6 liters per minute (L/min). At around two liters per minute, the patient will have an $FiO_2$ (percent oxygen in the inhaled $O_2$/air mixture) of about 28% oxygen. This rate may be increase somewhat to about 8 L/min if the gas is passed through a humidifier at room temperature via a nasal interface into the patient's nose. This is generally adequate for many people whose condition responds to about 35-40% inhaled $O_2$ ($FiO_2$), but for higher concentrations of $O_2$, higher flow rates are generally needed.

When a higher $FiO_2$ is needed, one cannot simply increase the flow rate. This is true because breathing 100% $O_2$ at room temperature via a nasal cannula is irritating to the nasal passage and is generally not tolerated above about 7-8 L/min. Simply increasing the flow rate may also provoke bronchospasm.

To administer $FiO_2$ of about 40% to about 100%, non-rebreathing masks (or sealed masks) are used at higher flows. The mask seals on the face and has a reservoir bag to collect the flow of oxygen during the exhalation phase and utilize one-way directional valves to direct exhalation out into the room and inhalation from the oxygen reservoir bag. This method is mostly employed in emergency situations and is generally not tolerated well for extended therapy.

High flow nasal airway respiratory support ("high flow therapy" or "HFT") is administered through a nasal cannula into an "open" nasal airway. The airway pressures are generally lower than Continuous Positive Airway Pressure (CPAP) and Bi-level Positive Airway Pressure (BiPAP) and are not monitored or controlled. The effects of such high flow therapies are reported as therapeutic and embraced by some clinicians while questioned by others because it involves unknown factors and arbitrary administration techniques. In such procedures, the pressures generated in the patients' airways are typically variable, affected by cannula size, nare size, flow rate, and breathing rate, for instance. It is generally known that airway pressures affect oxygen saturation, thus these variables are enough to keep many physicians from utilizing HFT.

SUMMARY

The present disclosure relates to a gas delivery conduit adapted for fluidly connecting to a respiratory gases delivery system in a high flow therapy system. In one embodiment, the gas delivery conduit includes a first connector adapted for connecting to the respiratory gases delivery system, a second connector adapted for connecting to a fitting of a patient interface and tubing fluidly connecting the first connector to the second connector where the first connector has a gas inlet adapted to receive the supplied respiratory gas. In one aspect of this embodiment, the gas delivery conduit includes one of electrical contacts and temperature contacts integrated into the first connector. In another aspect of this embodiment, the gas delivery conduit includes a sensing conduit integrated into the gas delivery conduit. In yet another aspect of this embodiment, the first connector of the gas delivery conduit is adapted to allow the user to couple the first connector with the respiratory gases delivery system in a single motion. In yet another aspect of this embodiment, the first connector of the gas delivery conduit is adapted to allow the user to couple the first connector with the respiratory gases delivery system by moving the connector in a direction along an axis of the gas inlet.

The present disclosure relates to a high flow therapy system including a microprocessor, one or more heating elements, a non-sealing respiratory interface and a sensor. The heating elements are disposed in electrical communication with the microprocessor and are capable of heating a liquid to create a gas. The non-sealing respiratory interface is configured to deliver the gas to a patient. The sensor is disposed in electrical communication with the microprocessor and is configured to measure pressure in an upper airway of the patient.

The present disclosure also relates to a method of supplying a patient with gas. The method includes providing a high flow therapy device including a microprocessor, one or more heating elements disposed in electrical communication with the microprocessor and capable of heating a liquid to create a gas, a non-sealing respiratory interface configured to deliver the gas to a patient and a sensor disposed in electrical communication with the microprocessor and configured to measure pressure in the upper airway of the patient. This method also includes heating the gas and delivering the gas to a patient.

The present disclosure also relates to a method of minimizing respiratory infections of a patient. The method includes providing a high flow therapy device, heating the gas and delivering the gas to a patient. The high flow therapy device of this method includes at least one heating element capable of heating a liquid to create a gas and a non-sealing respiratory interface configured to deliver the gas to a patient.

The present disclosure also relates to a method of supplying a patient with gas. The method including providing a high flow therapy device, heating a gas and delivering the gas to a patient. The high flow therapy device of this method includes at least one heating element, a non-sealing respiratory interface, a blower, an air inlet port and an air filter. The at least one heating element is capable of heating a liquid to create a gas. The non-sealing respiratory interface is configured to deliver the gas to a patient. The blower is disposed in mechanical cooperation with the non-sealing respiratory interface and is capable of advancing the gas at least partially through the non-sealing respiratory interface. The air inlet port is configured to enable ambient air to flow towards to the blower. The air filter is disposed in mechanical cooperation with the air inlet port and is configured to remove particulates from the ambient air.

The present disclosure also relates to a method of supplying a patient with gas. The method includes providing a high flow therapy device, heating a gas and delivering the gas to a patient. The high flow therapy device of this method includes at least one heating element, a non-sealing respiratory interface, and controlling a source of one or more compressed gases. The at least one heating element is capable of heating a liquid to create a gas. The non-sealing respiratory interface is configured to deliver the gas to a patient. The compressed gas control mechanism is disposed in mechanical cooperation with the non-sealing respiratory interface and is capable of advancing the gas at least partially through the non-sealing respiratory interface.

The present disclosure also relates to a method of treating a patient for an ailment such as a headache, upper airway resistance syndrome, obstructive sleep apnea, hypopnea and snoring. The method includes providing a high flow therapy device, heating a gas and delivering the gas to a patient. The high flow therapy device includes at least one heating element capable of heating a liquid to create a gas and a non-sealing respiratory interface configured to deliver the gas to a patient.

The present disclosure also relates to a method of delivering respiratory gas to a patient. The method includes providing a high flow therapy device, monitoring the respiratory phase of the patient and pressurizing the gas. The high flow therapy device of this method includes at least one heating element capable of heating a liquid to create a gas, a non-sealing respiratory interface configured to deliver the gas to a patient, and a sensor configured to measure pressure in the upper airway of the patient.

The present disclosure also relates to a high flow therapy device including a microprocessor, at least one heating element, a non-sealing respiratory interface, a sensor and a mouthpiece. The at least one heating element is disposed in electrical communication with the microprocessor and is capable of heating a liquid to create a gas. The non-sealing respiratory interface is configured to deliver the gas to a patient. The sensor is disposed in electrical communication with the microprocessor and is configured to measure pressure in an upper airway of the patient. The mouthpiece is disposed in mechanical cooperation with the sensor.

BRIEF DESCRIPTION OF THE DRAWINGS

Reference will now be made to the accompanying drawing figures, which are not necessarily drawn to scale.

FIG. 5 is a front perspective view of a nasal cannula according to a further embodiment of the invention.

FIG. 6 depicts a cross section of a nasal insert of a nasal cannula according to a particular embodiment of the invention.

FIG. 7 depicts a cross section of a nasal insert of a nasal cannula according to a further embodiment of the invention.

FIGS. 33A-33C show various aspects of a humidity chamber in accordance with embodiments of the present disclosure.

FIGS. 34A-34D illustrate a saddle for use with a therapy device of the present disclosure.

DETAILED DESCRIPTION OF THE INVENTION

Figure 1:
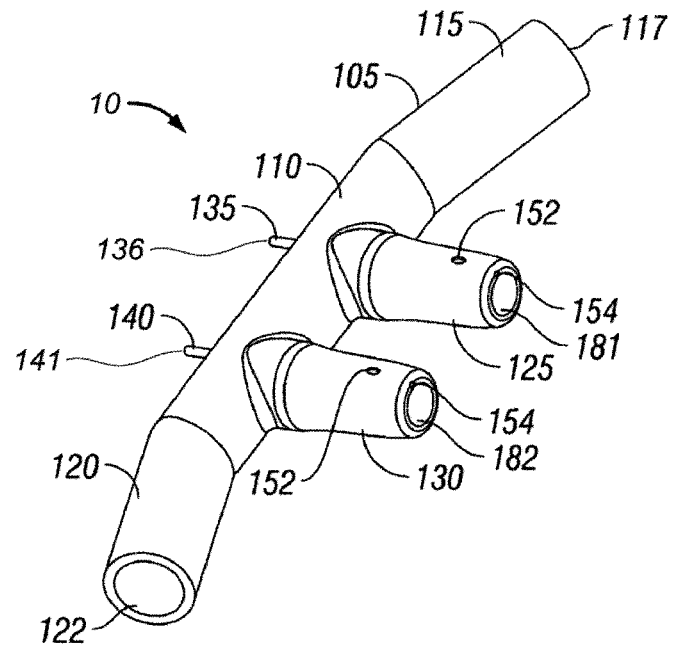
FIG. 1 is a perspective view of a nasal cannula according to a particular embodiment of the invention.

The present inventions now will be described with reference to the accompanying drawings, in which some, but not all embodiments of the inventions are shown. Indeed, these inventions may be embodied in many different forms and should not be construed as limited to the embodiments set forth herein. Rather, these embodiments are provided so that this disclosure will satisfy applicable legal requirements. Like numbers refer to like elements throughout. For example, elements 130, 230, 330, 430, 530, 830, and 930 are all nasal inserts according to various embodiments of the invention.

Overview of Functionality

Nasal cannula according to various embodiments of the invention may be configured to deliver high-flow therapeutic gases to a patient's upper airway through the patient's nose. Such gases may include, for example, air, humidity, oxygen, therapeutic gases or a mixture of these, and may be heated or unheated. In particular embodiments of the invention, the cannula may be useful for CPAP (continuous positive airway pressure) applications, which may be useful in the treatment of sleep apnea and in providing respiratory support to patients (e.g., after abdominal surgery), to alleviate snoring, or for other therapeutic uses.

Nasal cannula according to particular embodiments of the invention include (or are adapted to facilitate the positioning of) one or more sensors adjacent or within one or more of the cannula's nasal inserts. Accordingly, the nasal cannula may be configured so that at least a portion of one or more sensors is in place in one or both of a user's nares when the nasal cannula is operably worn by the user. This may be particularly helpful in evaluating the environment of the internal portion of the user's nose and/or the user's upper airway. As described in greater detail below, in various embodiments of the invention, the cannula is adapted so that it will not create a seal with the patient's nares when the cannula is in use.

Nasal cannula according to other embodiments of the invention include nozzles that are adapted to remain outside of a user's nares while the cannula is in use. Accordingly, the nozzles avoid sealing with the patient's nares while the cannula is in use. In some embodiments, the nasal cannula include elongate extensions that are inserted into the user's nares to detect pressure in one or both nares.

In certain embodiments of the invention, sensors are provided adjacent or within both of the nasal cannula's nasal inserts. In various other embodiments, sensors are provided adjacent or within one or more elongate extensions that extend into the user's nares. In various embodiments, elongate extensions may be used in conjunction with nasal inserts or with nozzles. The use of sensors may be useful, for example, in monitoring environmental changes from one of the user's nares to the other. This information may be helpful, for example, in determining when the dominant flow of air changes from one of the user's nares to the other, which may affect the desired flow characteristics of therapy. Accordingly, data from each nare may provide information that may be useful in establishing or modifying the user's treatment regimen. Further, multiple sensors may be used in various embodiments.

Overview of Exemplary Cannula Structures

A cannula 10 according to one embodiment of the invention is shown in FIG. 1. As may be understood from this figure, in this embodiment, the cannula 10 includes a base portion 105, which is hollow, elongated, and tubular that includes a central portion 110, a first end portion 115, and a second end portion 120. The first and second end portions 115, 120 may be angled relative to the central portion 110 as shown in FIG. 1.

In various embodiments of the invention, the cannula 10 includes a first inlet 117 adjacent the outer end of the first end portion 115, and a second inlet 122 adjacent the second end portion 120 (in other embodiments, the cannula may include only one such inlet). The cannula 10 further comprises a pair of hollow, elongated, tubular nasal inserts (e.g., nasal catheters), nasal inserts 125, 130, that extend outwardly from the base portion 105 and that are in gaseous communication with the base portion's interior. In various embodiments, the respective central axes of the nasal inserts 125, 130 are substantially parallel to each other, and are substantially perpendicular to the central axis of the central portion 110 of the base portion 105.

In particular embodiments of the invention, the cannula defines at least one conduit that is adapted to guide at least one sensor so that the sensor is introduced adjacent or into the interior of the cannula so that, when the cannula is being operably worn by a user, the environment being monitored by the at least one sensor reflects that of the internal portion of the user's nose and/or the user's upper airway. In various embodiments of the invention, a user may temporarily insert the at least one sensor into or through the conduit to determine correct settings for the cannula system, and then may remove the sensor after the correct settings have been achieved. In other embodiments, the at least one sensor may be left in place within the conduit for the purpose of monitoring data within (or adjacent) the cannula over time (e.g., for purposes of controlling the user's therapy regimen). In a further embodiment, the at least one sensor may be positioned adjacent an outlet of the conduit.

The at least one sensor may be connected (e.g., via electrical wires) to a computer and/or a microprocessor that is controlling the flow of respiratory gases into the cannula. The computer may use information received from the at least one sensor to control this flow of gas and/or other properties of the system, or may issue an alarm if the information satisfies pre-determined criteria (e.g., if the information indicates potentially dangerous conditions within the patient's airway or if the system fails to operate correctly).

Figure 8A:
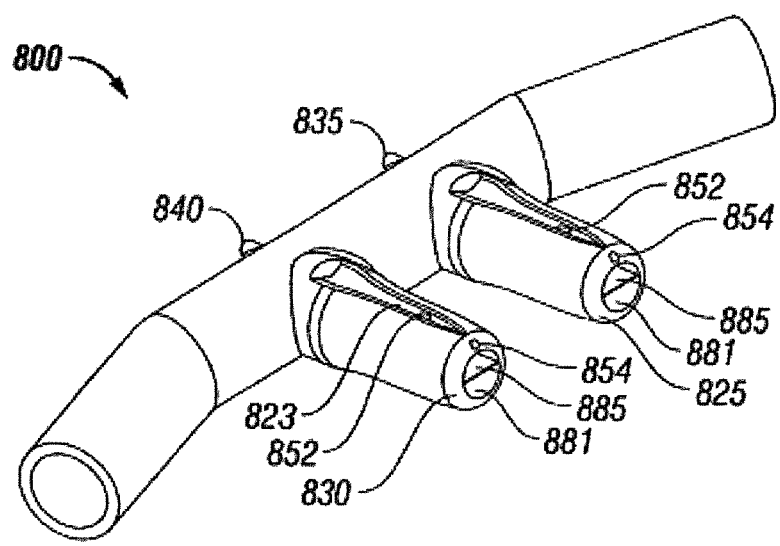
FIG. 8A is a front perspective view of a nasal cannula according to another embodiment of the invention.
Figure 8B:
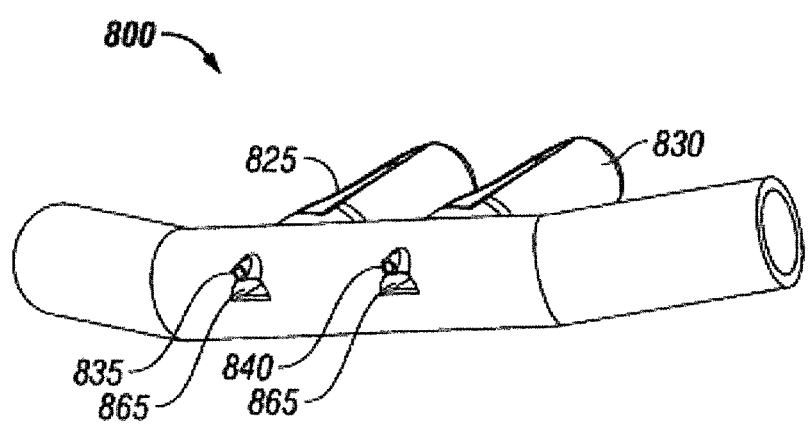
FIG. 8B is a rear perspective view of the nasal cannula shown in FIG. 8A.
Figure 8C:
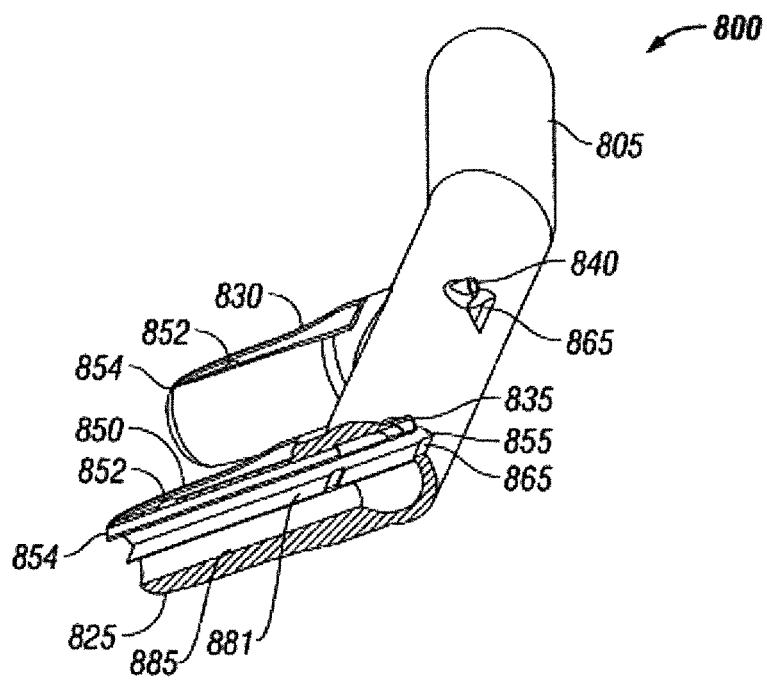
FIG. 8C is a perspective cross-sectional view of the nasal cannula shown in FIG. 8A.

As may be understood from FIGS. 8A-8C, in a particular embodiment of the invention, at least one of the cannula's conduits 850 is defined by, and extends within, a side wall of the cannula 800. Alternatively, the conduit may be disposed within an interior passage defined by the cannula. For example, one or more of the conduits may be defined by a tube that is attached immediately adjacent an interior surface of the cannula (e.g., adjacent an interior surface of the cannula's base portion, or an interior surface of one of the cannula's nasal inserts). The cannula's conduits are preferably adapted for: (1) receiving a flow of gas at one or more inlets that are in communication with the conduit, and (2) guiding this flow of gas to an outlet in the cannula. In various embodiments, one or more of the inlets is defined within an exterior portion of one of the cannula's nasal inserts.

As may be understood from FIG. 1, in various embodiments of the invention, each of the cannula's conduit outlets 136, 141 is located at the end of a respective elongate, substantially tubular, outlet member 135, 140. For example, in the embodiment shown in FIG. 1, the cannula 10 includes a first outlet member 135 that is substantially parallel to the cannula's first nasal insert 125. In this embodiment, the first outlet member 135 and the first nasal insert 125 may be positioned on opposite sides of the base portion 105 as shown in FIG. 1. Similarly, in a particular embodiment of the invention, the cannula 10 includes a second outlet member 140 that is substantially parallel to the cannula's second nasal insert 130. The second outlet member 140 and second nasal insert 130 are also preferably positioned on opposite sides of the base portion 105. Nasal inserts 125, 130 also may have nozzle outlets 181, 182 respectively.

In various embodiments of the invention, a sensor (e.g., a pressure, temperature, or $O_2$ sensor) is provided in communication or adjacent at least one of (and preferably each of) the cannula's outlets 136, 141 and is used to measure the properties of gas from that outlet 136, 141. In a further embodiment of the invention, accessory tubing is used to connect each outlet 135, 140 with at least one corresponding sensor (and/or at least one external monitoring device) that may, for example, be spaced apart from the cannula 10.

In yet another embodiment of the invention, one or more sensors are provided within the conduit, and used to measure the properties of gas accessed through the conduit. In this embodiment, information from each sensor may be relayed to a control system outside the cannula via, for example, an electrical wire that extends from the sensor and through the outlet 135, 140 of the conduit in which the sensor is disposed.

In alternative embodiments of the invention, each of the cannula's conduits may extend: (1) from the conduit inlets 152, 154; (2) through, or adjacent, a side wall of one of the nasal inserts 125, 130; (3) through, or adjacent, a side wall of the body portion 105; and (4) to an outlet 135, 140 that is defined within, or disposed adjacent, the body portion 105. In one such embodiment, the conduit comprises a substantially tubular portion that is disposed adjacent an interior surface of the cannula's body portion.

Figure 2:
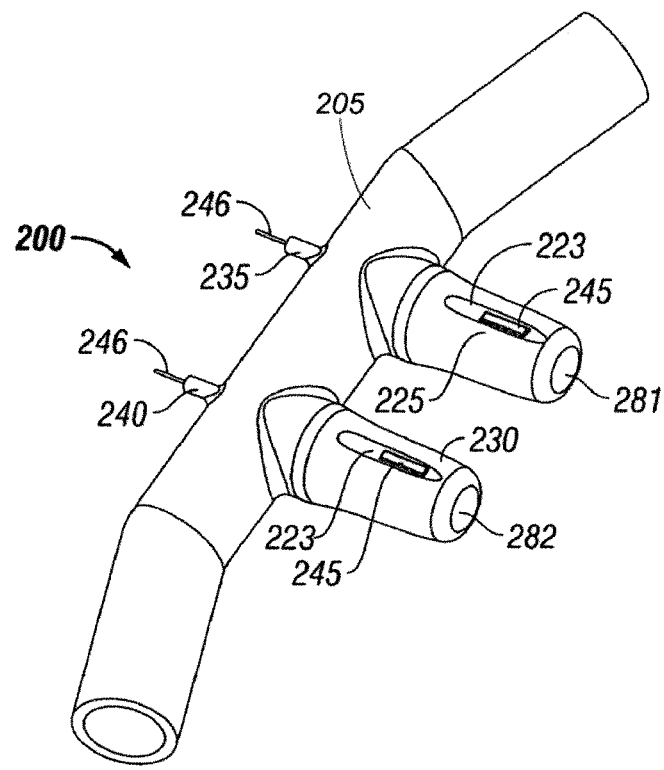
FIG. 2 is a perspective view of a nasal cannula according to a further embodiment of the invention.
Figure 3:
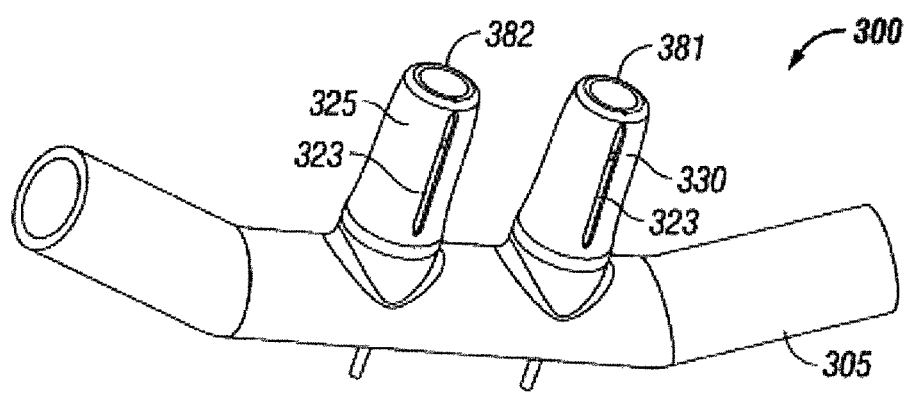
FIG. 3 is a perspective view of a nasal cannula according to another embodiment of the invention.

As may be understood from FIG. 2, in certain embodiments of the invention, the cannula 200 includes at least one sensor 245 that is integrated into an exterior portion of the cannula 200 (e.g., within a recess 223 formed within an exterior surface of one of the cannula's nasal inserts, nasal inserts 225, 230). In this embodiment, information from the sensor 245 may be relayed to a control system outside the cannula 200 via an electrical wire 246 that extends from the sensor 245, through a conduit, and out an outlet 235, 240 in the conduit. In various embodiments of the invention, the conduit extends through or adjacent an interior portion of a sidewall of one of the nasal inserts 225, 230 and/or through or adjacent an interior portion of a sidewall of the body portion 205. Nasal inserts 225,230 also have nozzle outlets 281, 282 respectively.

In particular embodiments of the invention, at least one sensor 245 is fixedly attached to the cannula 10 so that it may not be easily removed by a user. Also, in particular embodiments, at least one sensor 245 is detachably connected adjacent the cannula 10 so that the sensor 245 may be easily detached from (and, in certain embodiments, reattached to) the cannula 10.

Figure 10:
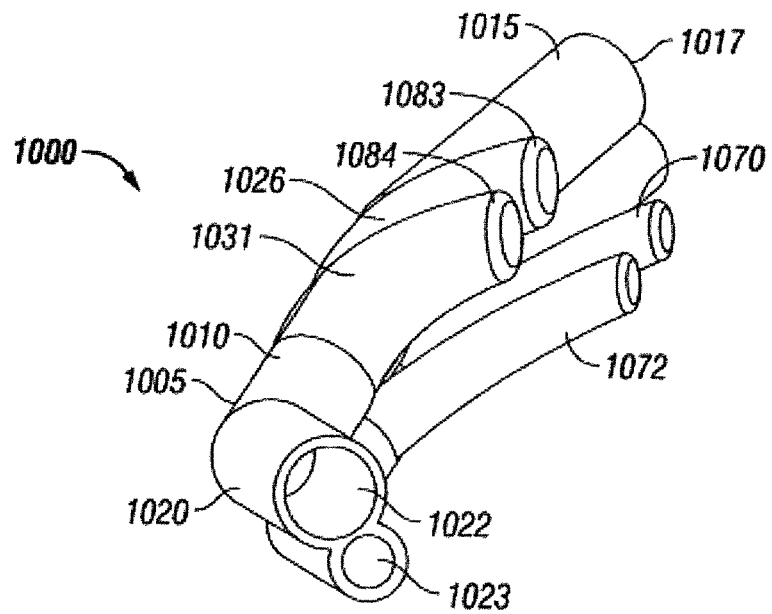
FIG. 10 is a perspective view of a nasal cannula according to another embodiment of the invention.

The cannula 1000 includes a base portion 1005, which is hollow, elongated, and tubular, that includes a central portion 1010, a first end portion 1015, and a second end portion 1020. The first and second end portions 1015 and 1020 may be angled relative to the central portion 1010, as shown in FIG. 10. In various embodiments of the invention, the cannula 1000 includes a first tubing inlet 1017 adjacent the outer end of the first end portion 1015, and a second tubing inlet 1022 adjacent the outer end of the second end portion 1020.

The cannula 1000 further comprises a pair of hollow, elongated, tubular nozzles (a first nozzle 1026 and a second nozzle 1031) that extend outwardly from the base portion 1005. In various embodiments, the respective central axes of the nozzles 1026, 1031 are substantially parallel to each other and are substantially perpendicular to the central axis of the central portion 1010 of the base portion 1005. In various embodiments, the nozzles 1026, 1031 define passageways that are in gaseous communication with the interior of the base portion 1005. In particular embodiments of the invention, the first and second nozzles 1026, 1031 are adapted to be positioned outside of a user's nares while the cannula is in use. In particular embodiments, the nozzles 1026, 1031 each define a respective nozzle outlet. For example, the first nozzle 1026 defines a first nozzle outlet 1083, and the second nozzle 1031 defines a second nozzle outlet 1084. In various embodiments, when the cannula 1000 is operatively positioned adjacent a user's nares, each of the nozzle's outlets 1083, 1084 is positioned to direct a focused flow of gas into a corresponding one of the user's nares.

Figure 12:
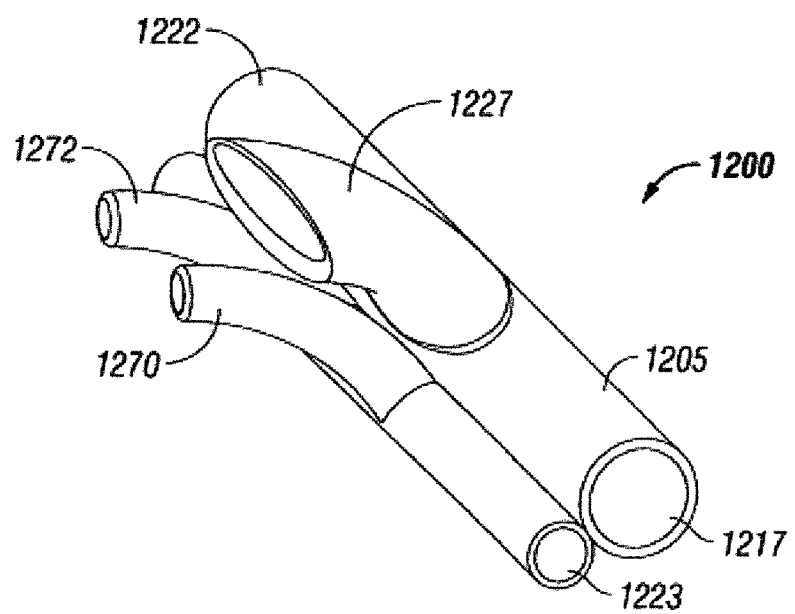
FIG. 12 is a perspective view of a nasal cannula according to yet another embodiment of the invention.

In alternative embodiments, such as the embodiment shown in FIG. 12, the cannula 1200 may include a single nozzle 1227 that defines a passageway that is in gaseous communication with an interior portion of the base portion 1205. As described in greater detail below, in various embodiments, the nozzle 1227 extends outwardly from the base portion 1205 and has an oblong, or elliptical, cross-section. In this and other embodiments, the nozzle 1227 is shaped to deliver a focused flow of gas simultaneously into both of a user's nares when the cannula 1200 is in use.

In various embodiments, the nasal cannula includes one or more elongate extensions that are adapted for insertion into one or more of the user's nares. For example, returning to the embodiment shown in FIG. 10, the cannula 1000 may include multiple elongate extensions (for example a first elongate extension 1070 and a second elongate extension 1072) that are long enough to allow each of the elongate extensions 1070, 1702 to be inserted into a respective one of the user's nares while the cannula 1000 is in use. In embodiments, elongate extensions 1070, 1072 may have conduit inlets 1052, 1053 respectively. In various embodiments, each of the elongate extensions 1070, 1072 may have a central axis that runs substantially parallel to the central axis of a corresponding nozzle 1026, 1031. For example, as can be understood from FIG. 10, in certain embodiments, a first elongate extension 1070 has a central axis that lies substantially parallel to and below the central axis of a corresponding first nozzle 1026, when the cannula is operatively positioned adjacent a user's nares. Similarly, in various embodiments, a second elongate extension 1072 has a central axis that lies substantially parallel to and below the central axis of a corresponding second nozzle 1031, when the nasal cannula 1000 is operatively positioned adjacent a user's nares. In various other embodiments, the elongate extensions may lie within, and extend outwardly from, their corresponding nozzles 1070, 1072.

As a further example, FIG. 12 illustrates an exemplary cannula 1200 having multiple elongate extensions (a first elongate extension 1270 and a second elongate extension 1272), which both lie substantially below a single nozzle 1227 when the cannula 1200 is in an operative position adjacent the user's nose. In some embodiments, the central axes of the first and second elongate extensions 1270, 1272, may be substantially parallel to the central axis of the nozzle 1227. Also, in various embodiments, one or both of the elongate extensions 1270, 1272 may lie within the nozzle 1227. In this and other embodiments, a distal end of each of the elongate extensions 1270, 1272 may extend beyond a distal end of the nozzle 1227. Elongate extensions 1270, 1272 may have conduit inlets 1252, 1253 respectively, while nozzle 1227 has a nozzle outlet 1281.

As described above, in certain embodiments of the invention, the nasal cannula includes one or more sensors that are adapted to measure gas data (e.g., gas pressure) within the user's nares while the cannula is in use. For example, the cannula 1000 shown in FIG. 10 may include a sensor positioned adjacent the distal end of one or both of the first and second elongate extensions 1070, 1072. In various embodiments, each elongate extension may be adapted to: (1) support a sensor adjacent (e.g., at) the distal end of the elongate extension; and (2) support a wire that is simultaneously connected to the sensor and a control mechanism that is adapted to adjust the properties of gas flowing through the cannula 1000.

In other embodiments, the elongate extensions define conduits. For example, one or more sensor(s) may be positioned within the interior or exterior of the elongate extensions and information from the sensor(s) may be relayed to a control system via a wire extending through a conduit (for example, elongate extension conduit 1023 of FIG. 10) or passages defined by each of the elongate extensions. In one embodiment, as shown, for example, in FIG. 10, the elongate extension conduit 1023 is shaped similarly to the base portion 1005, and lies substantially below the base portion 1005 when the cannula 1000 is operatively in use. In various embodiments, the elongate extension conduit 1023 is positioned within the base portion 1005 such that the first and second elongate extensions 1070, 1072 lie within, and extend outwardly from, the respective first and second nozzles 1026, 1031.

In various embodiments, each elongate extension defines a respective conduit that can serve as an air passageway. For example, in certain embodiments, each conduit is adapted to provide a passage that permits gaseous communication between a user's nares and a control system or other device for measuring and adjusting the properties of the air. In this and other embodiments, a sensor may be positioned at the control box to measure the properties (e.g., pressure) of air in the user's nares. In some embodiments, the elongate extensions define a conduit that serves both as an air passageway as well as a conduit for allowing a wire to pass from a sensor positioned adjacent the tip of the elongate extension to the control system or other device.

Data Monitored by Sensors

In various embodiments of the invention, such as those described above, one or more sensors may be positioned to measure gas data within an interior portion of one of the nasal cannula's conduits, or to measure gas data adjacent an exterior portion of the cannula. In such embodiments, one or more sensors may be, for example, positioned adjacent an interior or exterior surface of the cannula. In certain embodiments of the invention, one or more of the cannula's sensors is adapted to monitor one or more of the following types of data within the cannula's conduits, or adjacent the cannula's exterior surface (e.g., adjacent a side portion, or distal end of, one of the cannula's nasal inserts): (1) gas pressure; (2) gas flow rate; (3) carbon dioxide content; (4) temperature; (5) level; and/or (6) oxygen content.

Absolute Vs. Relative Pressure Measurements

In various embodiments of the invention, the cannula may be configured for sensing absolute pressure within, or adjacent, a particular portion of the cannula. Similarly, in particular embodiments, the cannula may be configured to measure the difference between the pressure at two different locations within the cannula. This may be done, for example, by providing two separate sensors (e.g., that are positioned in different locations within one of the cannula's conduits), or by providing two physically distinct gas intake conduits, each of which is adapted for routing gas from a different location within the cannula. For example, in various embodiments of the invention shown in FIG. 1, the first inlet 152 may be connected to a first intake conduit that is adapted for routing gas to a first sensor, and the second inlet 154 may be connected to a physically separate second intake conduit that is adapted for routing gas to a second pressure sensor. Information from the first and second sensors may then be used to calculate the difference in pressure between the first and second inlets 152, 154. Alternatively, a differential pressure sensor may be used.

Suitable Sensors

Suitable sensors for use with various embodiments of the invention include electronic and optical sensors. For example, suitable sensors may include: (1) Disposable MEM Piezoelectric sensors (e.g., from Silex Microsensors); (2) light-based sensors such as a McCaul $O_2$ sensor—see U.S. Pat. No. 6,150,661 to McCaul; and (3) Micro-pressure sensors, such as those currently available from Honeywell.

Non-Sealing Feature

Figure 4:
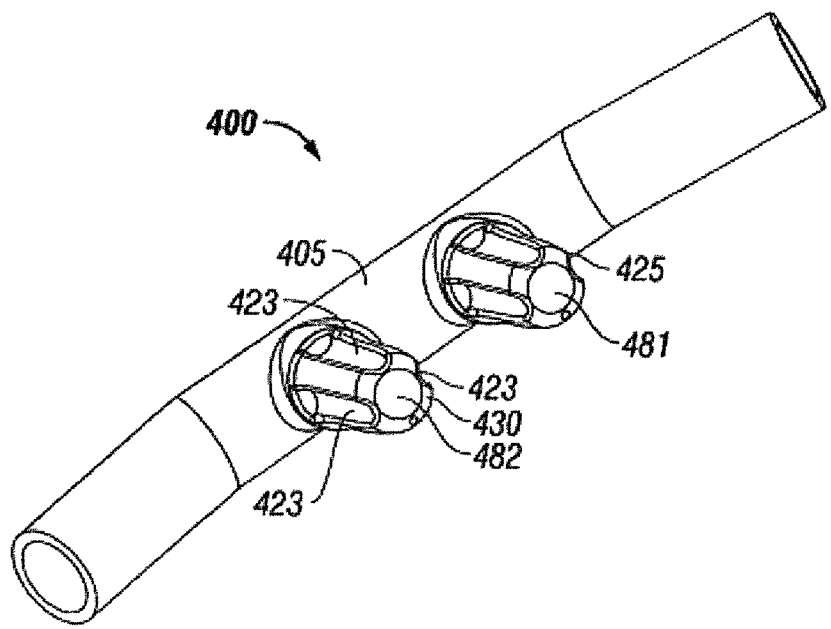
FIG. 4 is a perspective view of a nasal cannula according to yet another embodiment of the invention.

As shown in FIG. 4, in various embodiments of the invention, one or more of the nasal cannula's nasal inserts 425, 430 defines one or more recesses 423 (e.g., grooves, semicircular recesses, or other indentations or conduits) that extend along a length of the nasal insert's exterior surface. As may be understood from this figure, in various embodiments of the invention, at least one of these recesses 423 is an elongate groove that extends from adjacent a distal surface of the nasal insert 325, 330, 425, 430 and past the midpoint between: (1) the nasal insert's distal surface and (2) the portion of the nasal insert 425, 430 that is immediately adjacent the nasal cannula's base portion 305, 405. As may also be understood from this figure, in various embodiments of the invention, each groove 423 extends substantially parallel to the central axis of its respective nasal insert 425, 430.

In particular embodiments of the invention, such as the embodiment shown in FIG. 4, at least one of the nasal cannula's nasal inserts 425, 430 is configured so that when the nasal inserts 425, 430 are operatively positioned within a user's nares, the nasal inserts do not form an airtight seal with the user's nares. This may be due, for example, to the ability of air to flow adjacent the user's nare through recesses 423 in the nasal inserts 425, 430 when the user is wearing the nasal cannula.

As shown in FIG. 4, in various embodiments of the invention, cannula 400 has one or more nasal inserts 425, 430 that defines one or more recesses 423 (e.g., grooves, semicircular recesses, or other indentations or conduits) that extend along a length of the nasal insert's exterior surface. As may be understood from this figure, in various embodiments of the invention, at least one of these recesses 423 is an elongate groove that extends from adjacent a distal surface of the nasal insert 325, 330, 425, 430 and past the midpoint between: (1) the nasal insert's distal surface and (2) the portion of the nasal insert 425, 430 that is immediately adjacent the nasal cannula's base portion 305, 405. As may also be understood from this figure, in various embodiments of the invention, each groove 423 extends substantially parallel to the central axis of its respective nasal insert 425, 430.

In particular embodiments of the invention, such as the embodiment shown in FIG. 4, at least one of the nasal inserts 425, 430 is configured so that when the nasal inserts 425, 430 are operatively positioned within a user's nares, the nasal inserts do not form an airtight seal with the user's nares. This may be due, for example, to the ability of air to flow adjacent the user's nare through recesses 423 in the nozzles 425, 430 when the user is wearing the nasal cannula.

FIGS. 5-8 depict additional embodiments of the invention that are configured so that when the cannula's nasal inserts are operatively positioned adjacent (e.g., partially within) the user's nares, the nasal inserts do not form a seal with the user's nares. For example, in the embodiment shown in FIG. 5, illustrating cannula 500, at least one (and preferably both) of the cannula's nasal inserts, nasal inserts 525, 530, comprise a nasal insert body portion 555 (which may, for example, be substantially tubular), and one or more flange portions, flanges 560, 561, that are adapted to maintain a physical separation between an exterior side surface of the nasal insert body portion 555 and a user's nare when the nasal insert 525, 530 is inserted into the user's nare.

For example, in the embodiment of the invention shown in FIG. 5, each of the nasal inserts 525, 530 includes a nasal insert body portion 555 and a pair of co-facing, elongated flanges, flanges 560, 561 that each have a substantially C-shaped cross section. In this embodiment, these flanges 560, 561 cooperate with a portion of the exterior of the nasal insert body portion 555 to form a substantially U-shaped channel (which is one example of a "nasal lumen") through which ambient air may flow to and/or from a user's nasal passages when the cannula 500 is operatively in place within the user's nares. In this embodiment, when the nasal inserts 525, 530 are properly in place within the user's nares, respiratory gas is free to flow into the user's nose through the nasal insert body portion 555, and ambient air is free to flow into and out of the user's nose through a passage defined by: (1) the flanges 560, 561; (2) the exterior side surface of the nasal insert body portion 555 that extends between the flanges 560, 561; and (3) an interior portion of the user's nose. In various embodiments, air may flow to and/or from a user's nose through this passage when the cannula 500 is operatively in place within the user's nares. A pathway (e.g., a semicircular pathway) may be provided adjacent the interior end of this U-shaped channel, which may act as a passageway for gas exhaled and inhaled through the U-shaped channel. In embodiments, nasal inserts 525, 530 may have conduit inlets 552, 554, and cannula 500 may have conduit outlets 535, 540.

The general embodiment shown in FIG. 5 may have many different structural configurations. For example, as shown in FIG. 6, which depicts a cross section of a nasal insert according to a particular embodiment of the invention, the respiratory gas passageways of the nasal inserts 655 of a cannula may be in the form of a tube having an irregular cross section (e.g., a substantially pie-piece-shaped cross section) rather than a circular cross section. Alternatively, as may be understood from FIG. 7, the respiratory gas passageways of the nasal inserts 755 of a cannula may be in the form of a tube having a substantially half-circular cross section rather than a circular cross section.

Similarly, as may be understood from FIGS. 6 and 7, the shape and size of the cannula's flanges may vary from embodiment to embodiment. For example, in the embodiment shown in FIG. 6, each of the flanges 660, 661 has a relatively short, substantially C-shaped cross section and the distal ends of flanges 660, 661 are spaced apart from each other to form a gap. As shown in FIG. 7, in other embodiments, each of the flanges 760, 761 may have a relatively long, substantially C-shaped cross section and the distal ends of the flanges 760, 761 may be positioned immediately adjacent each other.

As may be understood from FIG. 7, in various embodiments of the invention, a separation 763 (e.g., a slit, such as an angular slit) is provided between the flanges 760, 761. This may allow the flanges 760, 761 to move relative to each other and to thereby conform to the nare in which the nasal insert is inserted. In other embodiments, the cross section of the nasal inserts is substantially as that shown in FIG. 7, except that no separation 763 is provided within the semi-circular flange portion. Accordingly, in this embodiment of the invention, a substantially semi-circular portion of the exterior of the air inlet cooperates with a substantially semi-circular portion of the flange portion to form an exterior having a contiguous, substantially circular cross section. One such embodiment is shown in FIGS. 8A-8C.

As may be understood from FIGS. 8A-8C, in this embodiment, when the cannula 800 is in use, respiratory gas may flow into the user's nose through passageways 881 (e.g., a portion of which may be defined by a corresponding respiratory gas inlet 855) that extend through each of the cannula's nasal inserts 825, 830. A pathway 885 of substantially semi-circular cross section extends between the distal end of each nasal insert 825, 830 to a substantially semicircular outlet 865 defined within the cannula's base 805. In various embodiments, when the cannula 800 is in use, the user may inhale and exhale gas through this pathway 885.

In certain embodiments, as discussed above, a conduit 850 is provided in each of the nasal inserts 825, 830 (see FIG. 8C). Each of these conduits 850 may be adapted to: (1) receive gas from the interior of a corresponding pathway 885 and/or from adjacent the exterior of one of the nasal inserts 825, 830, and (2) guide the gas out of a corresponding outlet 835, 840 in the cannula 800. As discussed above, one or more sensors may be disposed within, or adjacent, the conduit 850 and used to assess one or more attributes of gas flowing through or adjacent the conduit 850.

It should be understood that the embodiments of the invention shown in FIGS. 4-8 and related embodiments may have utility with or without the use of sensors or sensor conduits. It should also be understood that the various nasal inserts may be configured to be disposed in any appropriate orientation within the user's nares when the cannula is operably positioned within the user's nares. For example, in one embodiment of the invention, the cannula may be positioned so that the cannula's nasal lumen is immediately adjacent, or so that it faces anterior-laterally away from, the user's nasal spine.

Figure 9:
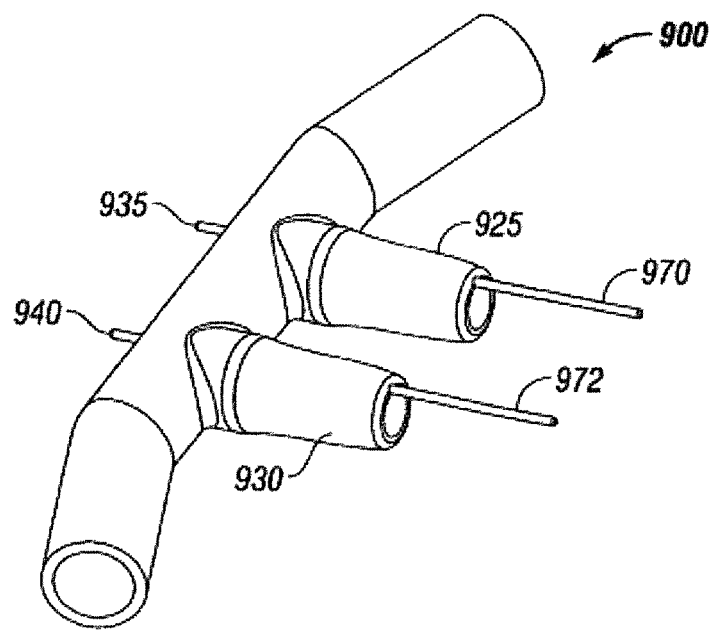
FIG. 9 is a perspective view of a nasal cannula according to a further embodiment of the invention.

Turning to yet another embodiment of the invention, as shown in FIG. 9, the cannula 900 and corresponding sensor may be adapted so that a tube inlet 970, 972 for at least one sensor (or the sensor itself) is maintained adjacent, and spaced a pre-determined distance apart from, the distal end of a respective nasal insert 925, 930. In this embodiment, the sensor (or sensor intake inlet) may be spaced apart from the rest of the cannula 900 adjacent one of the nasal cannula's outlet openings.

As may be understood from FIG. 10, in various embodiments, the first and second nozzles 1026, 1031 of the nasal cannula are configured to remain outside of the user's nares while the cannula is in use. For example, the nozzles may be of a length such that, when the cannula is in use, the distal ends of the nozzles 1026, 1031 lie adjacent, but outside, the user's nares. By preventing insertion of the nozzles 1026, 1031 into the nares, sealing of the nares can be avoided. As may be understood from FIG. 13, in various embodiments, when the nasal cannula is in an operative position adjacent the user's nares, an outlet portion (and distal end) of each nozzle 1326, 1331 is spaced apart from, and substantially in-line (e.g., substantially co-axial) with, a corresponding one of the patient's nares. In various embodiments, when the nasal cannula is operatively in use, the outlet of each nozzle is spaced apart from the patient's nares and each nozzle is positioned to direct a focused flow of gas into a particular respective one of the user's nares.

Figure 11:
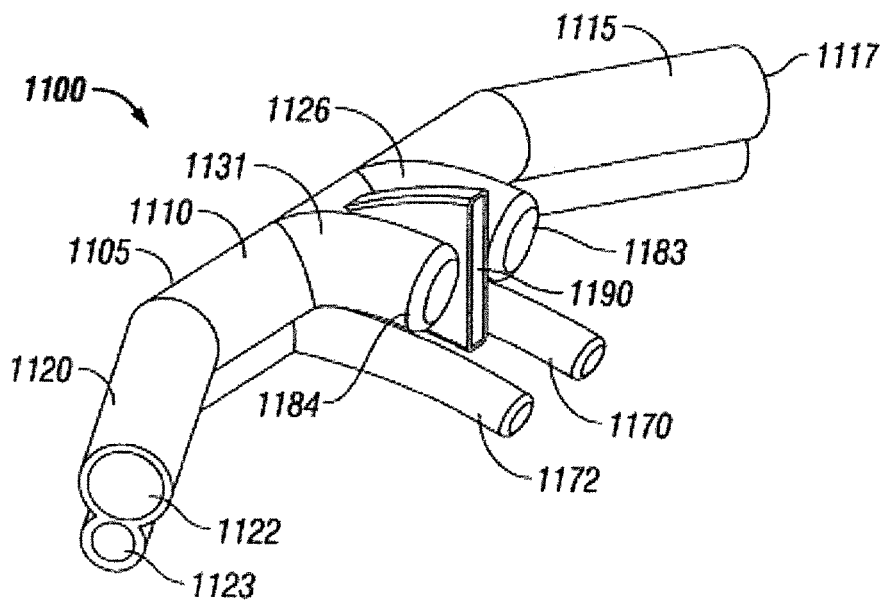
FIG. 11 is a perspective view of a nasal cannula according to a further embodiment of the invention.

As may be understood from FIG. 11, in particular embodiments, a stop 1190 may extend outwardly from the base portion 1105 of the cannula 1100. In some embodiments, the stop 1190 lies in between the first and second nozzles 1126, 1131 and defines a central axis that runs substantially parallel to the respective central axes of the nozzles 1126, 1131. The stop 1190, in some embodiments, may extend outwardly from the base portion 1105 a length greater than that of the nozzles 1126, 1131. In this manner, the stop 1190 prevents the nozzles 1126, 1131 from being inserted into the user's nares when the cannula 1100 is in use.

For example, the stop 1190 may be positioned so that when the cannula 1100 is in use, the stop is designed to engage the columella of the user's nose and thereby prevent the nozzles 1126, 1131 from being inserted into the user's nares. In various embodiments, the first and second nozzles 1126, 1131 are positioned on either side of the stop 1190 so that when the nasal cannula 1100 is operatively in use, the each nozzle 1126, 1131 will be spaced apart from a respective particular one of the patient's nares and will be positioned to direct a focused flow of gas into that particular nare by, for example, being positioned so that the outlet (and distal end) of each nozzle (first outlet 1183 and second outlet 1184) is substantially in-line (e.g., substantially co-axial) with, a corresponding one of the patient's nares.

As may be understood from FIG. 12, in various embodiments, the cannula 1200 may include only a single nozzle 1227. The nozzle 1227, in various embodiments, has an oblong or substantially elliptical cross-section. In these embodiments, the major axis of the ellipse runs substantially parallel to the central axis of the base portion 1205 of the nasal cannula. In one embodiment, the nozzle 1227 is wide enough to allow air to flow into both of a user's nares when the nasal cannula is in use. For example, in various embodiments, the width of the nozzle 1227 (e.g., a length defined by the major axis of the nozzle's elliptical cross section) may be approximately equal to (or greater than) the total width of the user's nares. In various embodiments, the cannula 1200 includes a first tubing inlet 1217 and a second tubing inlet 1222.

Figure 14:
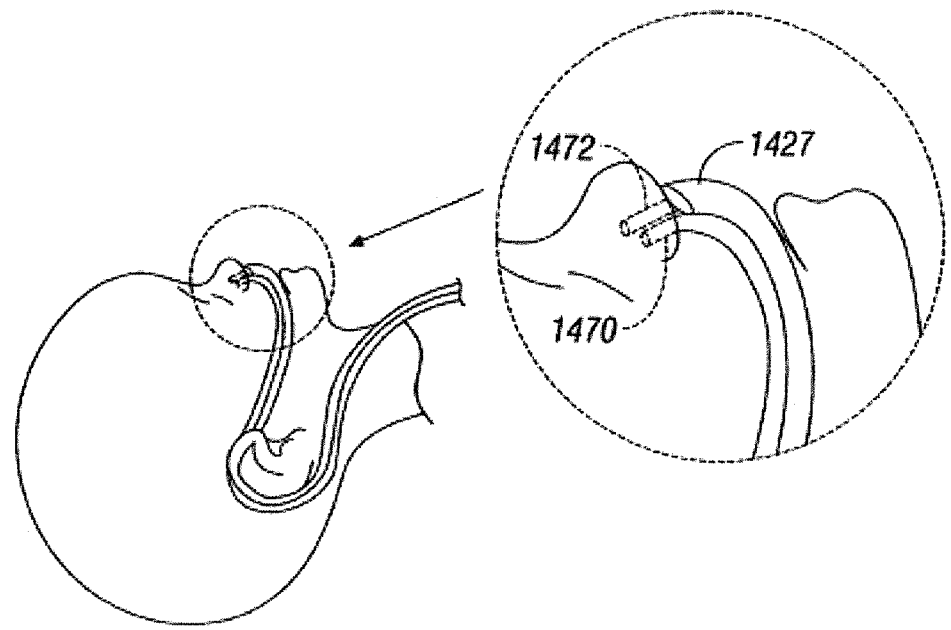
FIG. 14 illustrates another embodiment of a nasal cannula in use on a patient, according to a further embodiment of the invention.

As may be understood from FIG. 14, when the nasal cannula 1400 is operatively in use, a first lateral side 1430 of the nozzle outlet 1429 is spaced apart from, and adjacent, a user's first nare, and a second lateral side 1430 of the nozzle 1429 is spaced apart from, and adjacent, the user's second nare. In this and other configurations, the nozzle 1422 is configured to direct a focused flow of gas simultaneously into each of the user's nares. In various embodiments, when the nozzle is of a width approximately equal to (or greater than) the total width of the user's nares, and other widths, the nozzle 1227 is sufficiently wide to prevent the nozzle 1227 from being inserted into a user's nare, thus preventing sealing of the nasal cannula with the nare.

In various other embodiments, the cannula's single nozzle may have a different cross-section that is not oblong or elliptical. For example, the nozzle may have a substantially circular cross-section, with a diameter that is wide enough to allow air to flow into both of a user's nares when the cannula is in use, while simultaneously being wide enough to prevent insertion into a single nare. In various other embodiments, the nasal cannula may have more than one nozzle, each having a substantially oblong cross section and a width that prevents insertion into each of a user's nares.

In various embodiments, one or more of the cannula's elongate extensions has a diameter that is adapted to prevent sealing with the user's nares. For example, the elongate extension(s) may have a diameter that is substantially narrower than a user's nares, so that sealing is avoided. In other embodiments, the elongate extension(s) may include features such as grooves or recesses, as described above, to prevent sealing when inserted into a user's nare(s).

Exemplary Use of the Cannula

To use a cannula according to a particular embodiment of the invention, a physician or technician may have a patient use the cannula for a brief period of time, while the physician or technician monitors information received from the cannula's various sensors, or the information may be recorded for later analysis. The physician or technician may then use this information to adjust the structure or operation of the cannula until the cannula's sensors indicate that the patient's upper airway environment satisfies certain conditions.

Similarly, in various embodiments, the cannula's sensors may be used to monitor conditions within the patient's upper airway over time. In a particular embodiment, the cannula's sensors may be connected to a control system that will automatically alter or modify the flow of therapeutic gas into the cannula if information from the sensor indicates undesirable conditions within the patient's upper airway. In further embodiments of the invention, the sensor is connected to a control system that issues an alarm if information from the cannula's sensors indicates undesirable conditions within the patient's airway.

Figure 13:
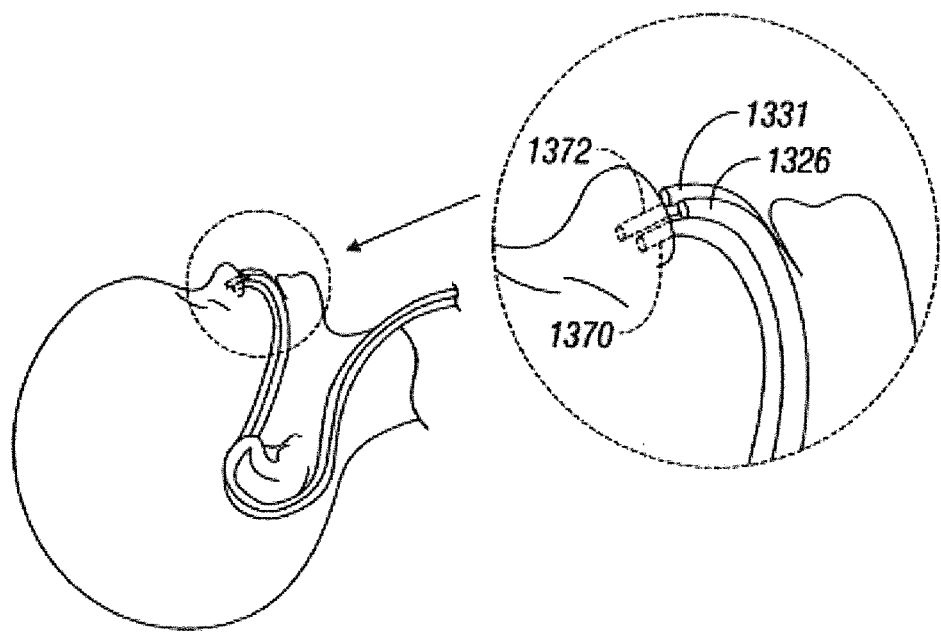
FIG. 13 illustrates an embodiment of a nasal cannula in use on a patient, according to one embodiment of the invention.

FIGS. 13 and 14 depict various embodiments of nasal cannulas being used on a patient. As may be understood from FIG. 13, for example, a nasal cannula is used on a young or small infant for high flow therapy. For example, a nasal cannula similar to that shown in FIG. 10 can be used. In various embodiments, first and second elongate extensions 1370, 1372 are inserted into the patient's nares, while corresponding first and second nozzles 1326, 1331 remain adjacent and external to the patient's nares. As may be appreciated, when the nasal cannula is in use, air flows into the patient's nares via the nozzles. FIG. 14 depicts one embodiment of a nasal cannula in use on a patient. In one embodiment, a nasal cannula such as that shown in FIG. 12 can be used. As may be understood from FIG. 14, a nasal cannula having a single nozzle 1427 can be used, in which the nozzle is sized and shaped (e.g., is elliptical and/or wider than a patient's nare) to prevent insertion into the patient's nares. In various other embodiments, nasal cannula having nasal inserts, as described throughout, can be used. In these embodiments, the nasal inserts are inserted into the user's nares while the cannula is in use. Nasal cannula according to embodiments of the invention can be used on a variety of patients.

High Flow Therapy Device

Figure 15:
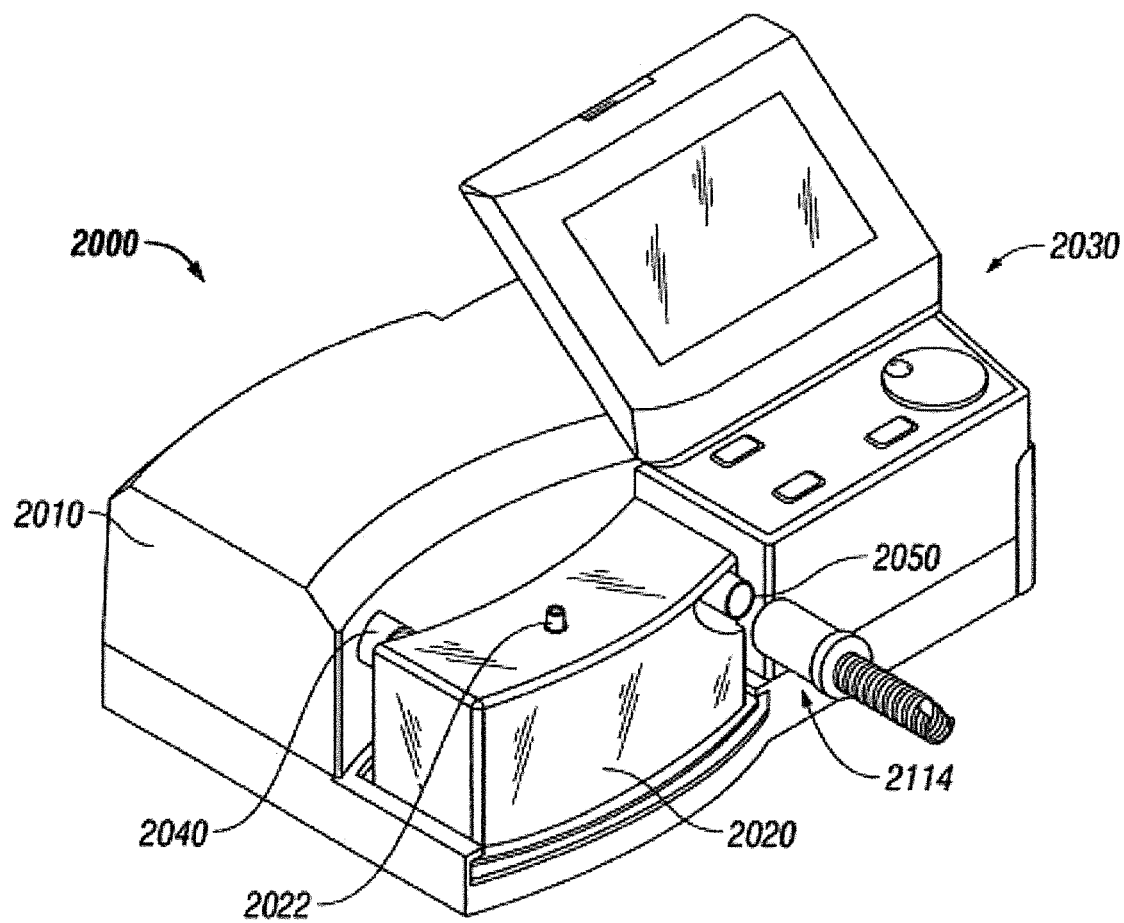
FIG. 15 illustrates a perspective view of a high flow therapy device in accordance with an embodiment of the present disclosure.
Figure 16:
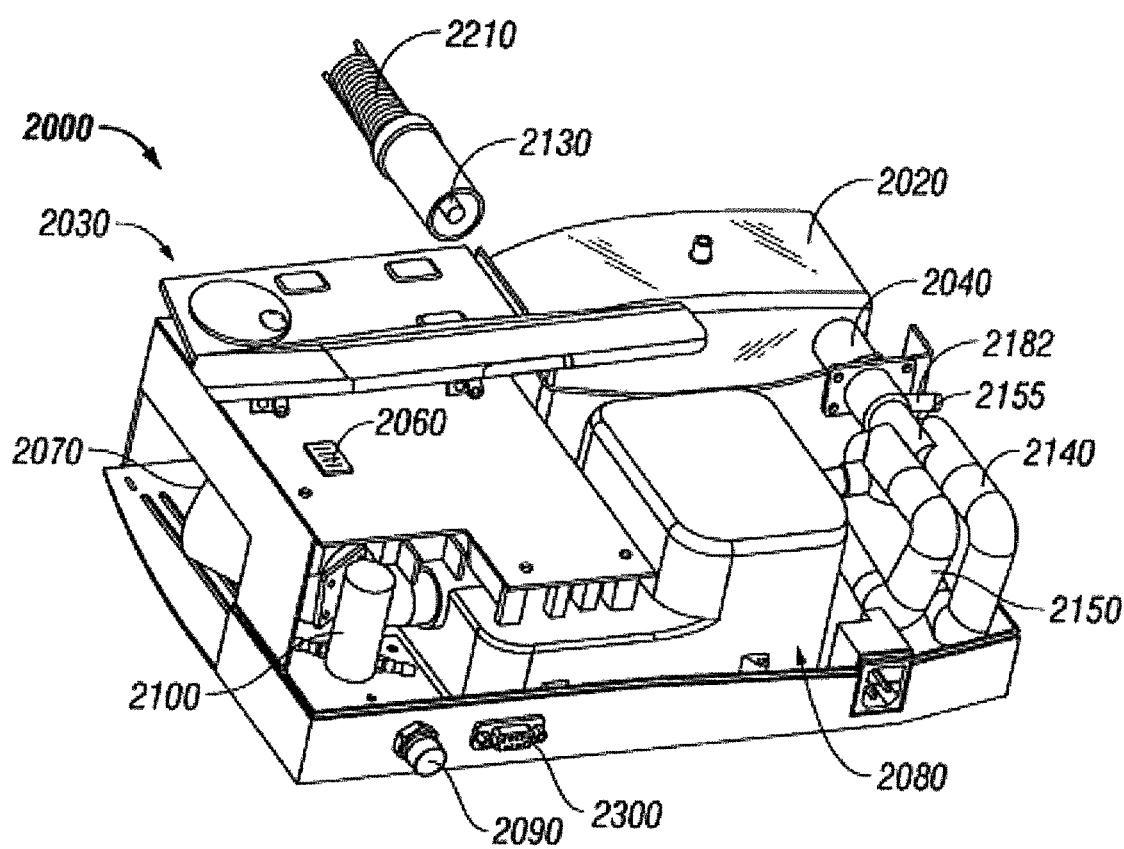
FIG. 16 illustrates a perspective view of the high flow therapy device of FIG. 15 showing internal components, in accordance with an embodiment of the present disclosure.
Figure 17:
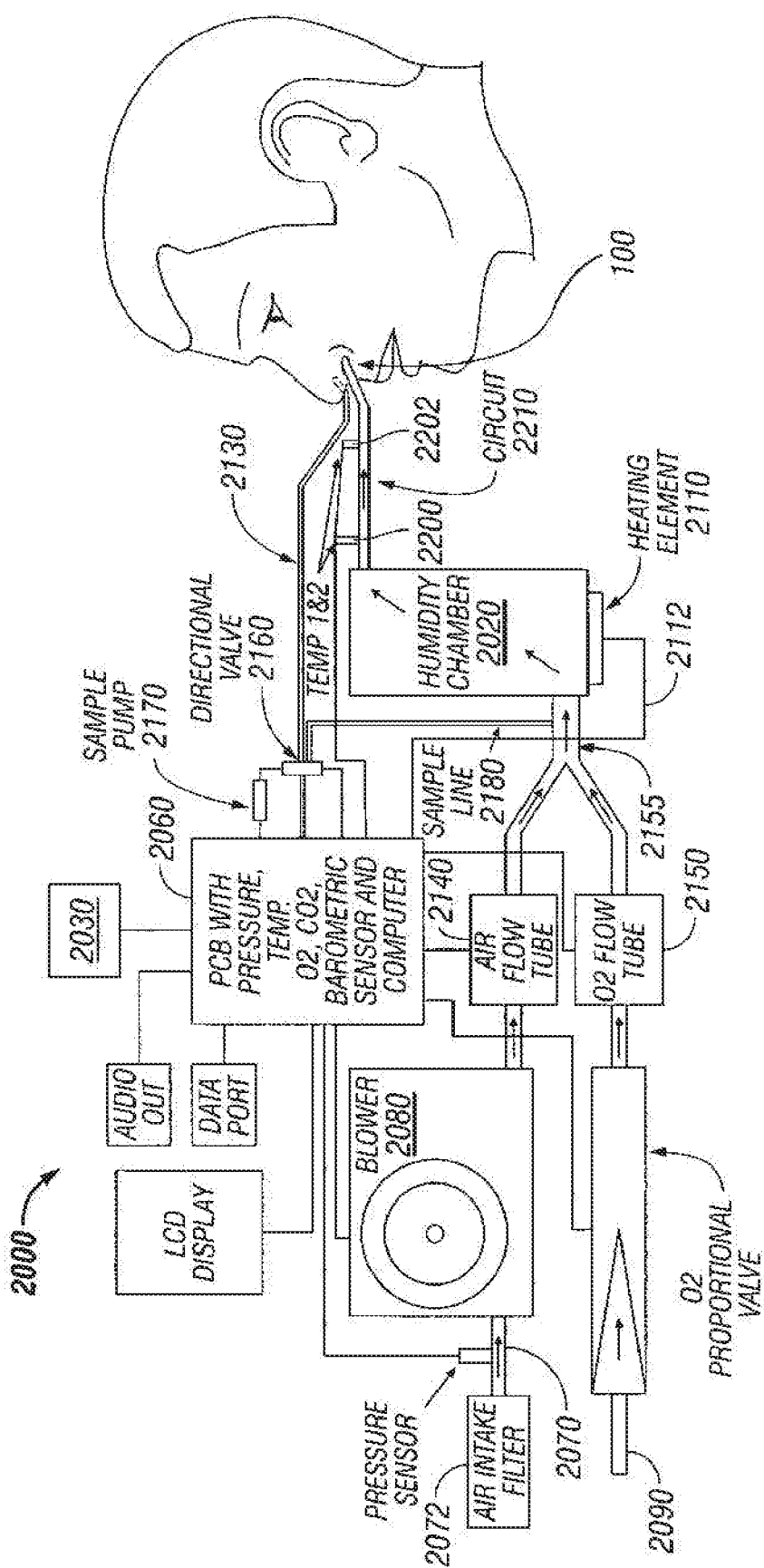
FIGS. 17 and 17A illustrates a schematic view of the high flow therapy device of FIGS. 15 and 16 with a nasal interface and a patient in accordance with embodiments of the present disclosure.

Now referring to FIGS. 15-17, a high flow therapy device 2000 is shown. High flow therapy device 2000 is configured for use with a non-sealing respiratory interface, such as cannula 10, for example, to deliver gas to a patient. In various embodiments, high flow therapy device 2000 is able to heat, humidify, and/or oxygenate a gas prior to delivering the gas to a patient. Additionally, embodiments of high flow therapy device 2000 are able to control and/or adjust the temperature of the gas, the humidity of the gas, the amount of oxygen in the gas, the flow rate of the gas and/or the volume of the gas delivered to the patient.

High flow therapy device 2000 is shown in FIG. 15 including a housing 2010, a humidity chamber 2020 (e.g., vapor generator), a user interface 2030, a gas inlet port 2040 and a gas outlet port 2050. A microprocessor 2060, an air inlet port 2070, a blower 2080, an oxygen inlet 2090 and a proportional valve 2100 are illustrated in FIG. 16. A non-sealing respiratory interface 100 (such as a cannula illustrated in FIGS. 1-14 (e.g., 10 or 1200)), is configured to mechanically cooperate with gas outlet port 2050 to supply a patient with gas.

Figure 18:
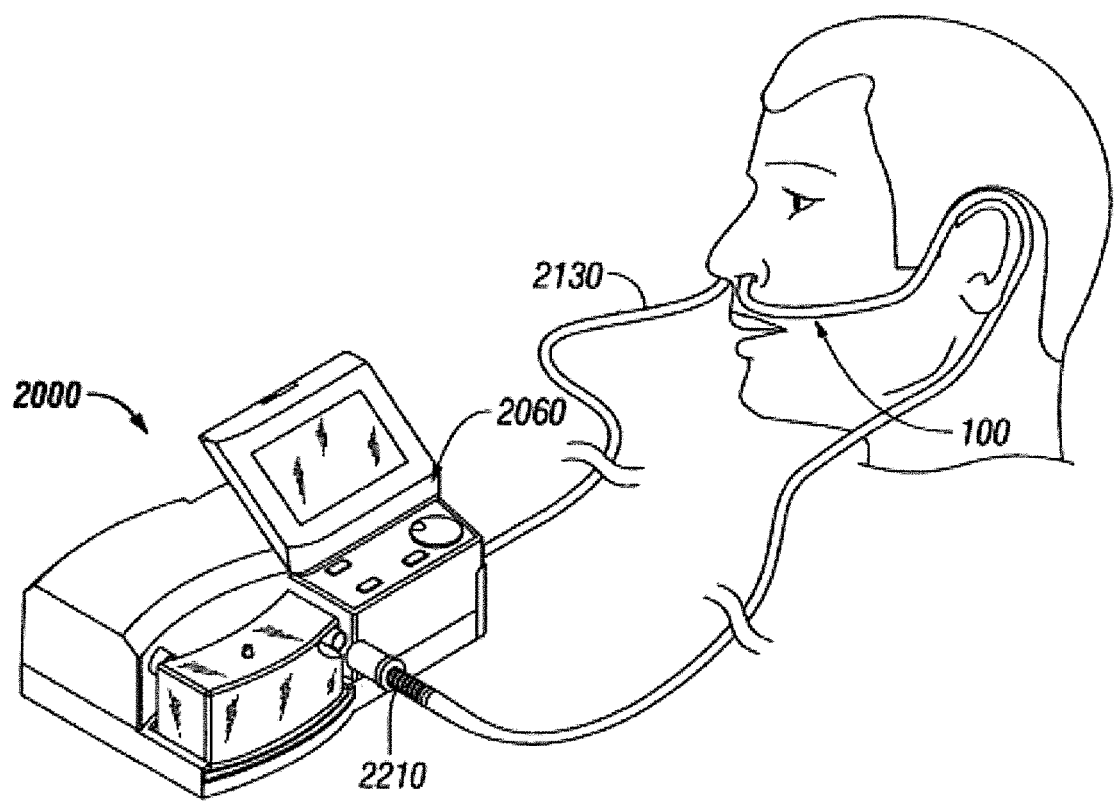
FIG. 18 illustrates a high flow therapy device including a nasal interface and a conduit in accordance with an embodiment of the present disclosure.
Figure 19:
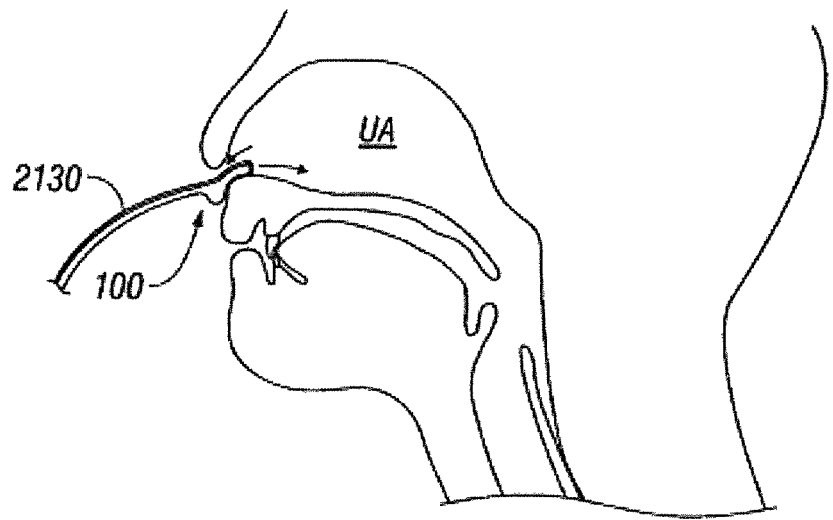
FIGS. 19 and 20 illustrate an enlarged view of a patient's upper airway and a nasal interface in accordance with two embodiments of the present disclosure.
Figure 20:
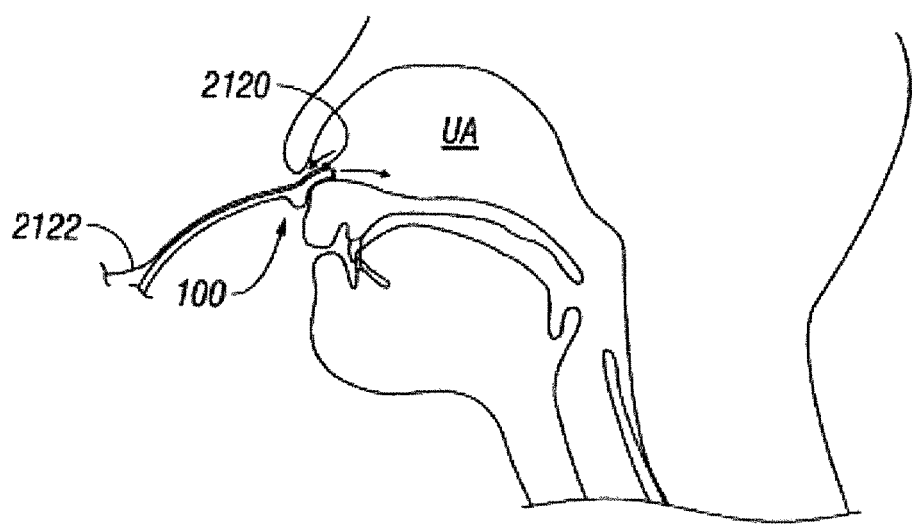

A heating element 2110 is shown schematically in FIG. 17 (and is hidden from view by humidity chamber 2020 in FIG. 15) is in electrical communication with microprocessor 2060 (which is included on printed circuit board ("PCB")), via wire 2112, for instance, and is capable of heating a liquid (e.g., water) within humidity chamber 2020 to create a gas. Non-sealing respiratory interface 100 is configured to delivery this gas to a patient. Further, a sensor 2120 or transducer (shown in FIG. 20) is disposed in electrical communication with microprocessor 2060 and is configured to measure pressure in the upper airway UA (including both the nasal cavity and the oral cavity) of a patient. In an embodiment, a sensor conduit 2130 extends between the upper airway of the patient and sensor 2120 (FIG. 19, sensor 2120 is not explicitly shown in FIG. 19, but may be disposed adjacent microprocessor 2060). In another embodiment, sensor 2120 is disposed at least partially within the upper airway of the patient with a wire 2122 relaying signals to microprocessor 2060 (FIGS. 18 and 20).

In use, a liquid (e.g., water) is inserted into humidity chamber 2020 through a chamber port 2022, for instance. Heating element 2110 heats the liquid to create a vapor or gas. This vapor heats and humidifies the gas entering humidity chamber 2020 through gas inlet port 2040. The heated and humidified vapor flows through gas outlet port 2050 and through non-sealing respiratory interface 100.

In a disclosed embodiment, sensor 2120 collects data for the measurement of the patient's respiration rate, tidal volume and minute volume. Further, based on measurements taken by sensor 2120 and relayed to microprocessor 2060, microprocessor 2060 is able to adjust the temperature of the gas, the humidity of the gas, the amount of oxygen of the gas, flow rate of the gas and/or the volume of the gas delivered to the patient. For example, if the pressure at the patient's upper airway is measured and determined to be too low (e.g., by a pre-programmed algorithm embedded on microprocessor 2060 or from a setting inputted by a operator), microprocessor 2060 may, for example, adjust the speed of blower 2080 and/or oxygen proportional valve 2100 so that sufficient pressure levels are maintained.

Additionally, sensor 2120 may be used to monitor respiratory rates, and microprocessor 2060 may signal alarms if the respiratory rate exceeds or falls below a range determined by either microprocessor 2060 or set by an operator. For example, a high respiratory rate alarm may alert the operator and may indicate that the patient requires a higher flow rate and/or higher oxygen flow.

With reference to FIG. 17, a pair of thermocouples 2200 and 2202 is illustrated, which detect the temperature entering and leaving a circuit 2210 disposed between non-sealing respiratory interface 100 and gas outlet port 2050. Further, a second heating element 2114 (or heater) (e.g., a heated wire) may be disposed adjacent air outlet port 2050 to further heat the gas. It is also envisioned that second heating element 2114 is disposed within circuit 2210. Thermocouples 2200 and 2202 are in communication with microprocessor 2060 and may be used to adjust the temperature of heating element 2110 and second heating element 2114. A feedback loop may be used to control the temperature of the delivered gas, as well as to control its humidity and to minimize rainout. FIG. 16 illustrates an embodiment of circuit 2210 including sensor conduit 2130 co-axially disposed therein, in accordance with an embodiment of the present disclosure.

Relating to the embodiment illustrated in FIG. 16, blower 2080 is used to draw in ambient air from air inlet port 2070 and force it through an air flow tube 2140, through gas inlet port 2040, through humidity chamber 2020 and through gas outlet port 2050 towards non-sealing respiratory interface 100. Blower 2080 is configured to provide a patient (e.g., an adult patient) with a gas flow rate of up to about 60 liters per minute. In a particular embodiment, it is envisioned that blower 2080 is configured to provide a patient with a gas flow rate of up to about 40 liters per minute. Additionally, an air intake filter 2072 (shown schematically in FIG. 17) may be provided adjacent air inlet port 2070 to filter the ambient air being delivered to the patient. It is envisioned that air intake filter 2072 is configured to reduce the amount of particulates (including dust, pollen, fungi (including yeast, mold, spores, etc.) bacteria, viruses, allergenic material and/or pathogens) received by blower 2080. Additionally, the use of blower 2080 may obviate the need for utilization of compressed air, for instance. It is also envisioned that a pressure sensor is disposed adjacent air intake filter 2072 (shown schematically in FIG. 17), which may be capable of determining when air intake filter 2072 should be replaced (e.g., it is dirty, it is allowing negative pressure, etc).

With continued reference to FIG. 16, oxygen inlet 2090 and is configured to connect to an external source of oxygen (or other gas) (not explicitly shown) to allow oxygen to pass through high flow therapy device 2000 and mix with ambient air, for instance. Proportional valve 2100, being in electrical communication with microprocessor 2060, is disposed adjacent oxygen inlet 2090 and is configured to adjust the amount of oxygen that flows from oxygen inlet 2090 through an oxygen flow tube 2150. As shown in FIGS. 16 and 17, oxygen flowing through oxygen flow tube 2150 mixes with ambient air (or filtered air) flowing through air flow tube 2140 in a mixing area 2155 prior to entering humidity chamber 2020.

In a disclosed embodiment, sensor 2120 measures both inspiration pressure and expiration pressure of the patient. In the embodiment illustrated in FIGS. 18 and 19, sensor conduit 2130 delivers the pressure measurements to sensor 2120 (not explicitly shown in FIGS. 18 and 19), which may be disposed adjacent microprocessor 2060. In the embodiment illustrated in FIG. 20, sensor 2120 is position adjacent the patient's upper airway and includes wire 2122 to transmit the readings to microprocessor 2060.

In various instances, clinicians do not desire ambient air to enter a patient's upper airway. To determine if ambient air is entering a patient's upper airway (air entrainment), the inspiration and expiration pressure readings from within (or adjacent) the upper airway may be compared to ambient air pressure. That is, a patient may be inhaling gas at a faster rate than the rate of gas that high flow therapy device 2000 is delivering to the patient. In such a circumstance (since non-sealing respiratory interface 100 is non-sealing), in addition to breathing in the supplied gas, the patient also inhales ambient air. Based on this information, microprocessor 2060 of high flow therapy device 2000 is able to adjust various flow parameters, such as increasing the flow rate, to minimize or eliminate the entrainment of ambient air.

Figure 21:
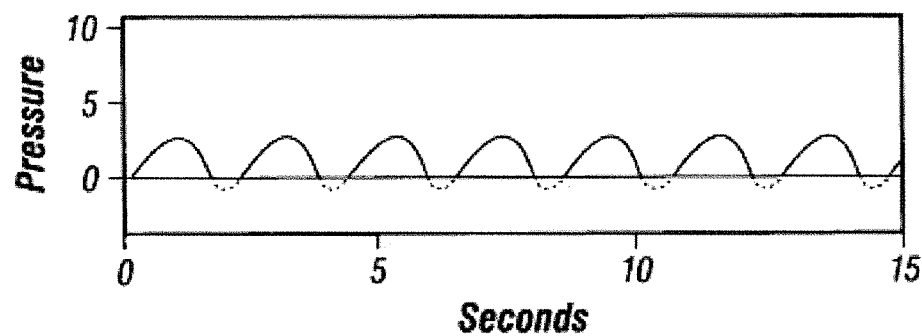
FIG. 21 illustrates an example of a screen shot of a user interface of the high flow therapy device of FIGS. 15-17 in accordance with an embodiment of the present disclosure.

FIG. 21 illustrates an example of a screen shot, which may be displayed on a portion of user interface 2030. The crest of the sine-like wave represents expiration pressure and the valley represents inspiration pressure. In this situation, ambient air entrainment into the patient's upper airway is occurring as evidenced by the valley of the sine wave dipping below the zero-pressure line. Microprocessor 2060 may be configured to automatically adjust an aspect (e.g., increasing the flow rate) of the gas being supplied to the patient by high flow therapy device 2000 to overcome the entrainment of ambient air. Further, microprocessor 2060 may convey the pressure readings to the operator who may then input settings to adjust the flow rate to minimize entrainment of ambient air or to maintain a level of pressure above the ambient air pressure. Further, lowering the flow rates during expiration may also minimize oxygen flow through high flow therapy device 2000. Such lowering of a flow rate may also minimize entry of oxygen into a closed environment, such as the patient room or the interior of an ambulance, where high levels of oxygen might be hazardous.

In a disclosed embodiment, sensor conduit 2130 may be used as a gas analyzer, which may be configured to take various measurements (e.g., percent of oxygen, percentage of carbon dioxide, pressure, temperature, etc.) of air in or adjacent a patient's upper airway.

In another embodiment (not explicitly illustrated), a gas port may be disposed adjacent housing 2010 to communicate with exterior of housing 2010. It is envisioned that the gas port is configured to allow the use of external devices to measure various gas properties (e.g., percent oxygen and pressure). Additionally, the gas port may be used for external verification of gas values. Further, a communications port 2300, shown in FIG. 16, may be included to facilitate connection with an external device, such as a computer, for additional analysis, for instance. Further, communications port 2300 enables connection with another device, enabling data to be monitored distantly, recorded and/or reprogrammed, for example.

A directional valve 2160 and/or a sample pump 2170 (schematically shown in FIG. 17) may also be included to facilitate sampling the gas for analysis. More specifically, in a particular embodiment, sample pump 2170 is capable of moving a quantity of gas towards the gas analyzer. As shown schematically in FIG. 17, the gas sample can be taken from a patient's upper airway via sensor conduit 2130 or from mixing area 2155 via a sample line 2180 and a sample port 2182 (FIG. 16). Directional valve 2160 may be controlled by microprocessor 2060 to direct a gas sample from either location (or a different location such as after the gas is heated). The gas analyzer can compare measurements of the gas sample(s) with predetermined measurements to ensure high flow therapy device 2000 is working optimally. It is further envisioned that sample pump 2170 may be configured to pump a gas or liquid towards the patient to provide the patient with an additional gas, such as an anesthetic, for instance and/or to clean or purge sensor conduit 2130.

The present disclosure also relates to methods of supplying a patient with gas. The method includes providing high flow therapy device 2000, as described above, for example, heating the gas, and delivering the gas to the patient. In this embodiment, high flow therapy device 2000 includes microprocessor 2060, heating element 2110 disposed in electrical communication with microprocessor 2060, non-sealing respiratory interface 100 configured to deliver gas to the patient and sensor 2120 disposed in electrical communication with microprocessor 2060 and configured to measure pressure in the upper airway of the patient. The method of this embodiment may be used, for instance, to provide a patient with respiratory assistance. Blower 2080 may also be included in high flow therapy device 2000 of this method. Blower 2080 enables ambient air to enter high flow therapy device 2000 (e.g., through filter 2072) and be supplied to the patient. In such an embodiment, high flow therapy device is portable, as it does not need an external source of compressed air, for example.

Another method of the present disclosure relates to minimizing respiratory infections of a patient. In an embodiment of this method, high flow therapy device 2000 includes heating element 2110 and non-sealing respiratory interface 100. Here, a patient may be provided with heated and/or humidified air (e.g., at varying flow rates) to help minimize respiratory infections of the patient. Further, such a method may be used in connection with certain filters 2072 to help prevent patients from obtaining various conditions associated with inhaling contaminated air, such as in a hospital. Additionally, providing appropriately warmed and humidified respiratory gases optimizes the motion of the cilia that line the respiratory passages from the anterior third of the nose to the beginning of the respiratory bronchioles, further minimizing risk of infection. Further, supplemental oxygen may add to this effect. Microprocessor 2060 in connection with sensor 2120 may also be included with high flow therapy device 2000 of this method for measuring and controlling various aspects of the gas being delivered to the patient, for instance, as described above.

A further method of the present disclosure relates to another way of supplying a patient with gas. The present method includes providing high flow therapy device 2000 including heating element 2110, non-sealing respiratory interface 100, blower 2080, air inlet port 2070 configured to enable ambient air to flow towards blower 2080 and filter 2070 disposed in mechanical cooperation with air inlet port 2070 and configured to remove pathogens from the ambient air. High flow therapy device 2000 of this method may also include microprocessor 2060 and sensor 2120.

Another method of the present disclosure includes the use of high flow therapy device 2000 to treat headaches, upper airway resistance syndrome, obstructive sleep apnea, hypopnea and/or snoring. High flow therapy device 2000 may be set to provide sufficient airway pressure to minimize the collapse of the upper airway during inspiration, especially while the user is asleep. High Flow Therapy (HFT) may be more acceptable to children and other who may not tolerate traditional CPAP therapy that requires a sealing interface. Early treatment with HFT may prevent the progression of mild upper airway resistance syndrome to more advanced conditions such as sleep apnea and its associated morbidity.

Another method of the present disclosure is the treatment of headaches using HFT. In an embodiment of treating/preventing headaches, gas may be delivered to patient at a temperature of between about 32.degree. C. and about 40.degree. C. (temperature in the higher end of this range may provide a more rapid response) and having at least about 27 milligrams of water vapor per liter. More specifically, it is envisioned that a gas having a water vapor content of between about 33 mg/liter and about 44 mg/liter may be used. It is envisioned that the gas being delivered to the patient includes moisture content that is similar to that of a typical exhaled breath. In an embodiment, the flow rates of this heated and humidified air are sufficient to prevent/minimize entrainment of ambient air into the respired gas during inspiration, as discussed above. The inclusion of an increased percentage of oxygen may also be helpful. Further, the gas may be delivered to the patient using non-sealing respiratory interface 100.

High flow therapy device 2000 used in these methods includes heating element 2110 and non-sealing respiratory interface 100. Microprocessor 2060 and sensor 2120 may also be included in high flow therapy device 2000 of this method. The inclusion of blower 2080, in accordance with a disclosed embodiment, enables high flow therapy device 2000 to be portable, as it does not need to be connected to an external source of compressed air or oxygen. Thus, high flow therapy device 2000 of this method is able to be used, relatively easily, in a person's home, a doctor's office, an ambulance, etc.

The present disclosure also relates to a method of delivering respiratory gas to a patient and includes monitoring the respiratory phase of the patient. Monitoring of a patient's respiratory phase is enabled by taking measurements of pressure in a patient's upper airway. Additionally, respiratory phase may be determined by pressure with circuit 2210 or by monitoring activity of the phrenic nerve. Real-time pressure measurements (see sine-like wave in FIG. 21, for example) enable real-time supplying of gas at different pressures to be delivered to the patient, or variable pressure delivery. For example, gas at a higher pressure may be delivered to the patient during inspiration and gas at a lower pressure may be delivered to the patient during expiration. This example may be useful when a patient is weak and has difficultly exhaling against an incoming gas at a high pressure. It is further envisioned that the pressure level of the gas being delivered to a patient is gradually increased (e.g., over several minutes) to improve patient comfort, for instance.

Figure 22:
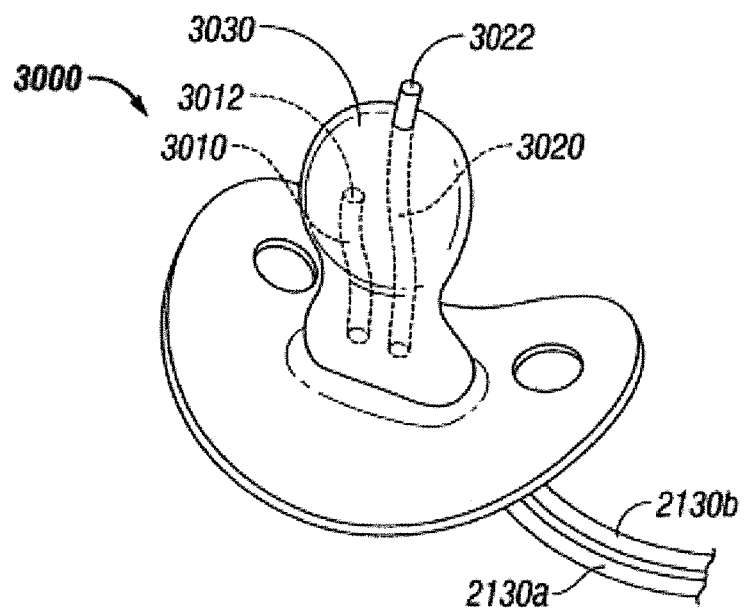
FIGS. 22 and 23 illustrate examples of a non-sealing respiratory interface in the form of a mouthpiece in accordance with embodiments of the present disclosure.
Figure 23:
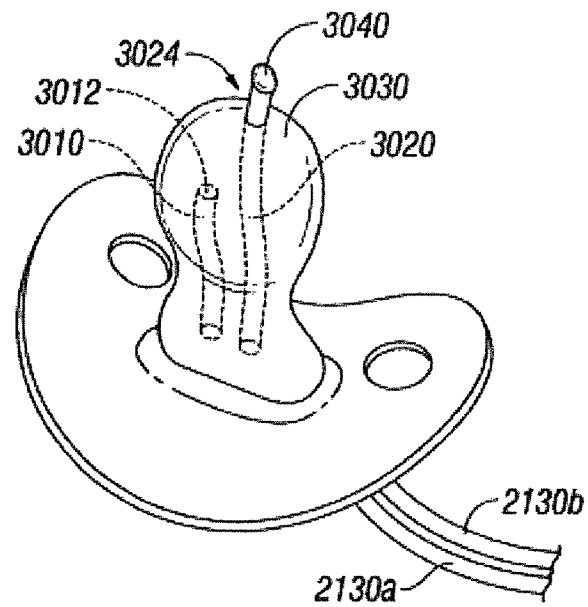
Figure 24:
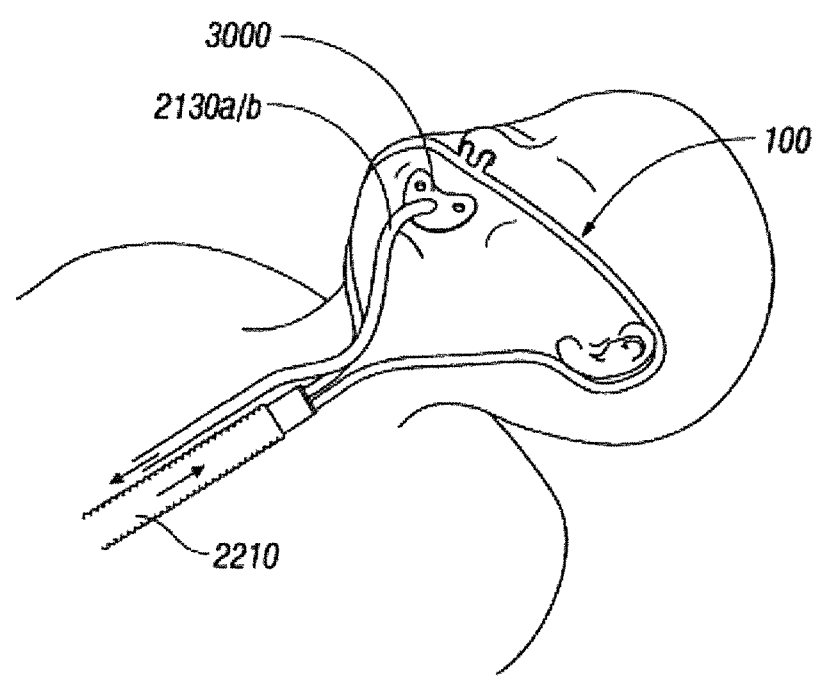
FIG. 24 illustrates a mouthpiece of FIG. 22 or 23 in use on a patient in accordance with an embodiment of the present disclosure.

With reference to FIGS. 22-24, mouthpiece 3000 is illustrated in accordance with an embodiment of the present disclosure. As briefly described above, mouthpiece 3000 is an example of a respiratory interface of the present disclosure. Mouthpiece 3000 (illustrated resembling a pacifier) may be used to detect upper airway pressure of a patient.

A first mouthpiece port 3010 may be used to measure pressure inside mouthpiece 3000 through open end 3012 of first port. First mouthpiece port 3010 may include an open-ended tube that communicates the pressure with mouthpiece 3000 to sensor 2120 (not explicitly shown in FIGS. 22-24) via first port conduit 2130*a*. Sensor 2120 may also be positioned within mouthpiece 3000. It is envisioned that mouthpiece 3000 is at least partially filled with a gas or liquid, e.g., water.

The pressure within mouthpiece 3000 may help evaluate, record or otherwise use the pressure data for determining the strength of sucking or feeding, for instance. The timing of the sucking motion and the differential pressures in the mouth may also be measured. The sucking pressure may be used to help determine the strength of the sucking and may be used to evaluate the health of an infant, for instance. The measurement of oral-pharyngeal pressure may also give data for setting or adjusting respiratory support therapy for the patient. It is envisioned that a relatively short first mouthpiece port 3010 may be used so that a bulb 3030 of mouthpiece 3000 acts as a pressure balloon. It is also envisioned that a relatively long first mouthpiece port 3010 having rigidity may be used to help prevent closure of the tube from pressure from alveolar ridges or from teeth, for example.

A second mouthpiece port 3020 is configured to enter a patient's mouth or oral cavity when mouthpiece 3000 is in use and is configured to measure pressure within the oral cavity (upper airway pressure) through an open end 3022 of second mouthpiece port 3020. Pressure from within the upper airway (e.g., measured adjacent the pharynx) may be transmitted to sensor 2120 via second port conduit 2130*b* or sensor 2120 may be positioned adjacent mouthpiece 3000. That is, the pressure communicated from with the upper airway to the patient's mouth is the pressure being measured. It is envisioned that second mouthpiece port 3020 extends beyond a tip of bulb 3030 to facilitate the acquisition of an accurate upper airway pressure measurement.

Referring to FIG. 23, a balloon 3040 is shown adjacent a distal end 3024 of second port 3020. Here, it is envisioned that a lumen of conduit 2130*b* is in fluid communication with the internal area of balloon 3040. Further, any forces against a wall of balloon 3040 are transmitted through the lumen towards sensor 2120 or transducer for control, observation or analysis.

The pressure within the oral cavity may vary during the phases of sucking and swallowing. High flow therapy device 2000 using mouthpiece 3000 enables concurrent measurement of sucking pressure within mouthpiece 3000 and the pressure outside mouthpiece 3000. This data may help determine treatment characteristics for respiratory support for infants, children or adults, e.g., unconscious adults.

In an embodiment of the present disclosure, high flow therapy device or system 2000 includes microprocessor 2060, heating element 2110, humidity chamber 2020, circuit 2210, blower 2080 and a feedback system. The heating element 2110 is disposed in electrical communication with the microprocessor 2060 and is capable of heating a liquid to create a gas. The humidity chamber 2020 is disposed in mechanical cooperation with the heating element 2110. The circuit 2210 is adapted to direct the gas towards a patient. The blower 2080 is disposed in electrical communication with the microprocessor 2060 and is capable of advancing the gas at least partially through the circuit 2210. The feedback system is configured to control a volume of gas being directed towards the patient.

Figure 17A:
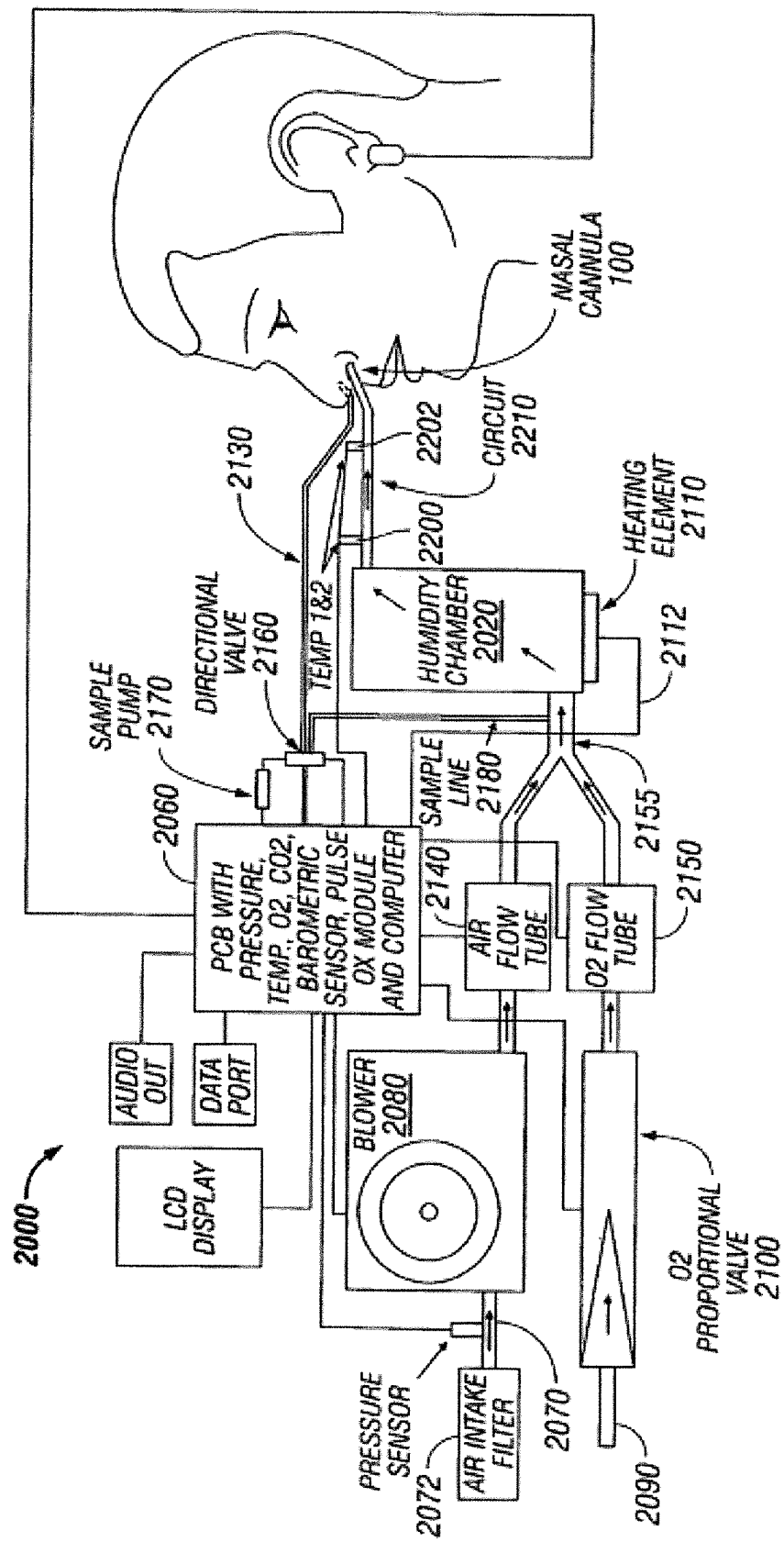

In an embodiment, it is envisioned that at least one gas flow sensor 2120 is disposed in electrical communication with the microprocessor 2060 and is configured to detect at least one flow characteristic of the gas. It is envisioned that high flow therapy system 2000 includes at least one compressed gas entry port 2090. Further, a pulse oximeter (see FIG. 17A), as discussed below, may be incorporated into high flow therapy system of the present disclosure.

The present disclosure also relates to a high flow therapy system 2000 including a microprocessor 2060, a heating element 2110, a humidity chamber 2020, a circuit 2210, at least one proportional valve 2132 (see FIGS. 32A and 32B) and a feedback system. The heating element 2110 is disposed in electrical communication with the microprocessor 2060 and is capable of heating a liquid to create a gas. The humidity chamber 2020 is disposed in mechanical cooperation with the heating element 2110. The circuit 2210 is configured to direct the gas towards a patient. The at least one proportional valve 2132 is disposed in electrical communication with the microprocessor 2060 and is configured to help control the entry and passage of gas. The feedback system is configured for controlling a volume of gas directed towards the patient. It is noted that, while the blower 2080 is not necessarily part of the other embodiments of the present disclosure, this embodiment specifically does not include a blower 2080.

It is envisioned that the high flow therapy system 2000 of this embodiment includes at least one gas flow sensor 2120 disposed in electrical communication with the microprocessor 2060 and is configured to detect at least one flow characteristic of the gas.

The present disclosure also relates to a method for delivering heated and humidified gas to a patient. The method includes the steps of providing a high flow therapy device, providing a non-sealing respiratory interface (e.g., 100), providing a sensor 2120, delivering gas from the high flow therapy device to a patient, and measuring the flow rate of the gas delivery to the patient. The high flow therapy device includes a heating element 2110 capable of heating a liquid to create a gas. The non-sealing respiratory interface is disposed in mechanical cooperation with the high flow therapy device and is configured to direct the gas towards a patient. The sensor is disposed in electrical communication with a microprocessor 2060 of the high flow therapy device and is configured to measure a flow rate of the gas delivered to the patient. An optional step of the method includes increasing (e.g., gradually increasing) the flow rate of the gas delivered to the patient.

The present disclosure relates to a gas delivery conduit adapted for fluidly connecting to a respiratory gases delivery system in a high flow therapy system. In one embodiment, the gas delivery conduit includes a first connector adapted for connecting to the respiratory gases delivery system, a second connector adapted for connecting to a fitting of a patient interface and tubing fluidly connecting the first connector to the second connector where the first connector has a gas inlet adapted to receive the supplied respiratory gas. In one aspect of this embodiment, the gas delivery conduit includes one of electrical contacts and temperature contacts integrated into the first connector. In another aspect of this embodiment, the gas delivery conduit includes a sensing conduit integrated into the gas delivery conduit. In yet another aspect of this embodiment, the first connector of the gas delivery conduit is adapted to allow the user to couple the first connector with the respiratory gases delivery system in a single motion. In yet another aspect of this embodiment, the first connector of the gas delivery conduit is adapted to allow the user to couple the first connector with the respiratory gases delivery system by moving the connector in a direction along an axis of the gas inlet.

Figure 25:
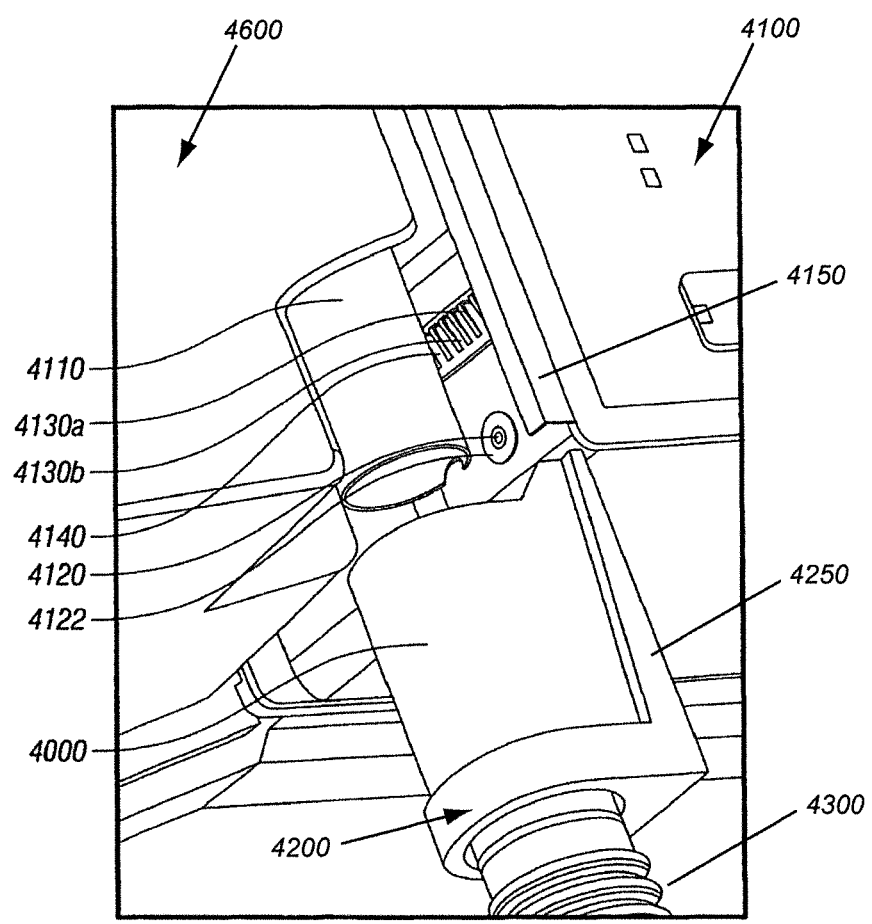
FIG. 25 illustrates an enlarged view of a connector according to an embodiment of the present disclosure.

With reference to FIGS. 25-28, a connector 4000 for use in a system for delivery of respiratory gases (e.g., high flow therapy device 2000) is shown. Connector 4000 includes a gas lumen 4010 and a pressure conduit 4020. Gas lumen 4010 is configured to link a gas outlet 4110 of a therapy device 4100 (e.g., high flow therapy device 2000) with a gas inlet 4210 of a delivery conduit 4200. Pressure conduit 4020 of delivery conduit 4200 is configured for engagement with at least one of a pressure port and a pressure sensor (collectively referred to as pressure port 4120 herein) of therapy device 4100. It is envisioned that a seal 4122 (e.g., an O-ring seal) is disposed adjacent pressure port 4120 (see FIGS. 25 and 27). FIG. 25 also illustrates a tubing 4300 that allows passage of the respiratory gases from connector 4000 to the second connector 5000 (which is described in further detail below). In embodiments, tubing 4300 may be corrugated as shown.

Figure 26:
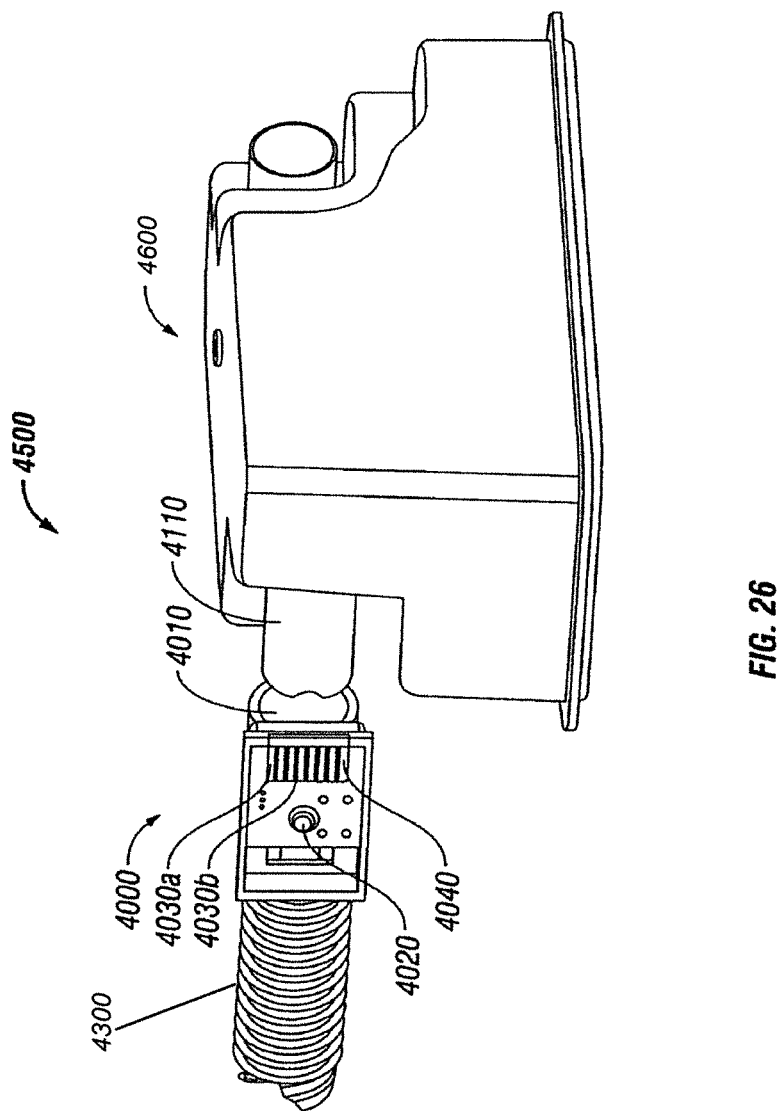
FIG. 26 illustrates a perspective view of a therapy device and the connector of FIG. 25.

In the embodiment illustrated in FIG. 26, connector 4000 also includes two temperature sensor contacts 4030a, 4030b for two temperature sensors (e.g., thermister or thermocouple) 4230a, 4230b of delivery conduit 4200 (shown in FIG. 28 on a lead wire) configured for engagement with temperature sensor contacts 4130a, 4130b of therapy device 4100. FIG. 26 also illustrates an electrical contact 4040 disposed on connector 4000. Electrical contact 4040 is configured for engagement with an electrical contact 4140 of therapy device 4100 and electrical engagement with a heating element 4240 of delivery conduit 4200. It is envisioned that electrical contact 4040 is configured to signal microprocessor 2060 to provide power to a heat transfer plate 4610 (discussed below) and/or heating element 4240.

Figure 27:
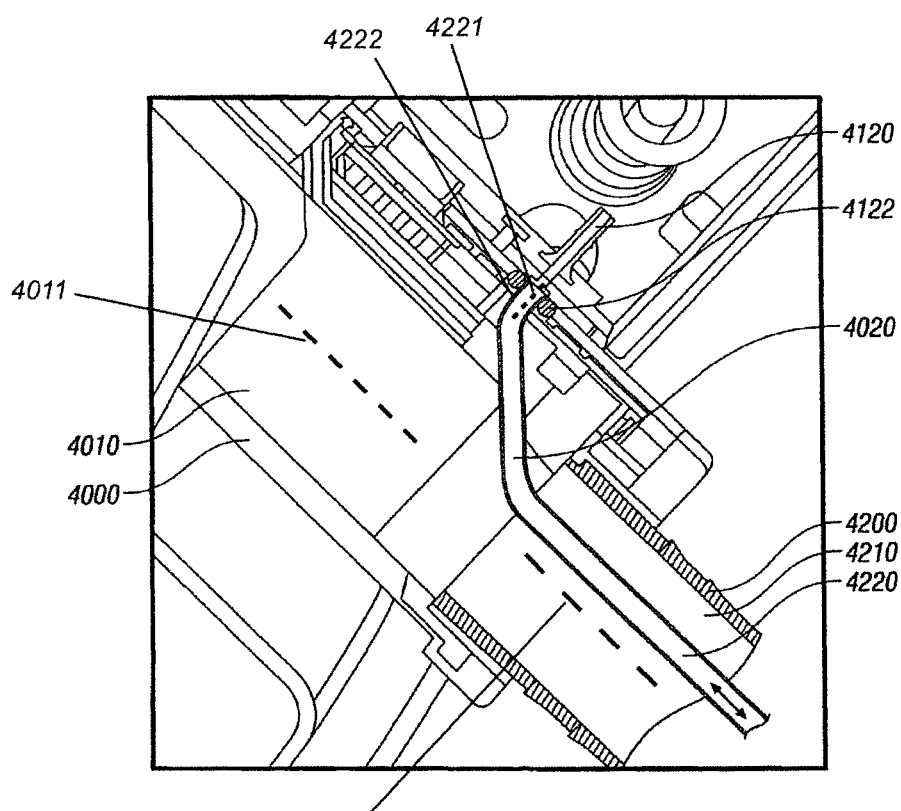
FIG. 27 illustrates a longitudinal cross-sectional view of the connector of FIGS. 25 and 26.
Figure 28:
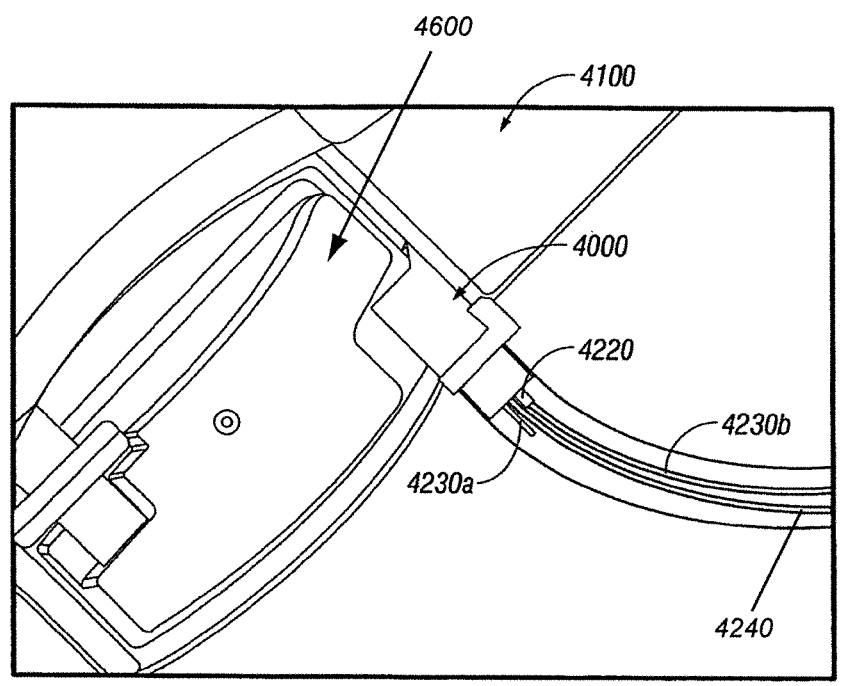
FIG. 28 illustrates a top view of the therapy device of FIG. 26 having the connector operably coupled to the therapy device.

With specific reference to FIG. 27, an inlet portion 4220 of pressure conduit 4020 of connector 4000 is coaxially disposed with gas lumen 4010 of connector 4000, and an outlet portion 4222 of pressure conduit 4020 is coaxially disposed with pressure port 4120 of therapy device 4100. It is envisioned that connector 4000 is also configured to convey gas, electricity and/or light between a patient delivery conduit 4200 and therapy device 4100.

It is therefore envisioned that various connections may be made with a single motion. That is, a gas connection, a pressure connection, at least one temperature sensor contact connection and an electrical connection may be made by approaching connector 4000 (coupled to delivery conduit 4200) with therapy device 4100.

It is further envisioned that connector 4000 is configured to connect at least one optical fiber, electrical wire and/or pressure conduit from a delivery conduit 4200 with therapy device 4100 in a single motion. This may be helpful when sensing temperature, pressure, flow, $CO_2$, $O_2$, Oxyhemoglobin saturation and other clinical measures from sensors operatively coupled to an airway interface or therapy device 4100.

Figure 35:
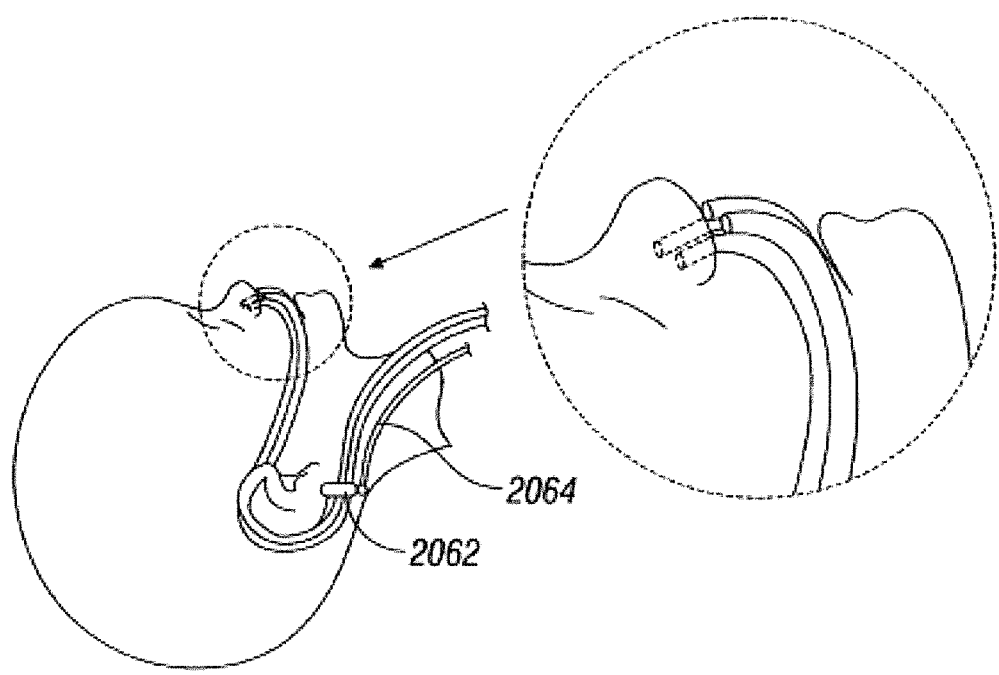
FIG. 35 illustrates a patient with a nasal cannula and an ear lobe probe.

Pulse oximetry, carbon dioxide and $O_2$ detection may thus be integrated into the HFT device (e.g., 4100) helping allow alarms to be incorporated based on data from at least one of a gas sensor, pulse oximetry, respiratory rate, tidal volume, pressure and from synthesis of clinical data. For instance, HFT device 4100 may include a pulse oximeter (schematically illustrated in FIG. 17A as part of printed circuit board box 2060). Pulse oximeter 2060 may be in the form of a microchip coupled with the printed circuit board and may include a probe 2062 and a wire 2064. In a disclosed embodiment (see FIG. 35), probe 2062 is connectable to a patient's ear lobe and wire 2064 connects probe 2062 with printed circuit board 2060 of HFT device 4100.

The HFT system may calculate cardiac output from data gathered from sensors. Data from sensors may be used in a feedback system to control at least one of $FiO_2$ and flow rate. The system may limit control to within pre-selected ranges. For example, $FiO_2$ could be set to be delivered in a range from about 21 percent to about 30 percent depending on pulse oximetry results, and an alarm could notify if the O2 saturation from pulse oximetry fell below a set value for example, below 90 percent.

Figure 32A:
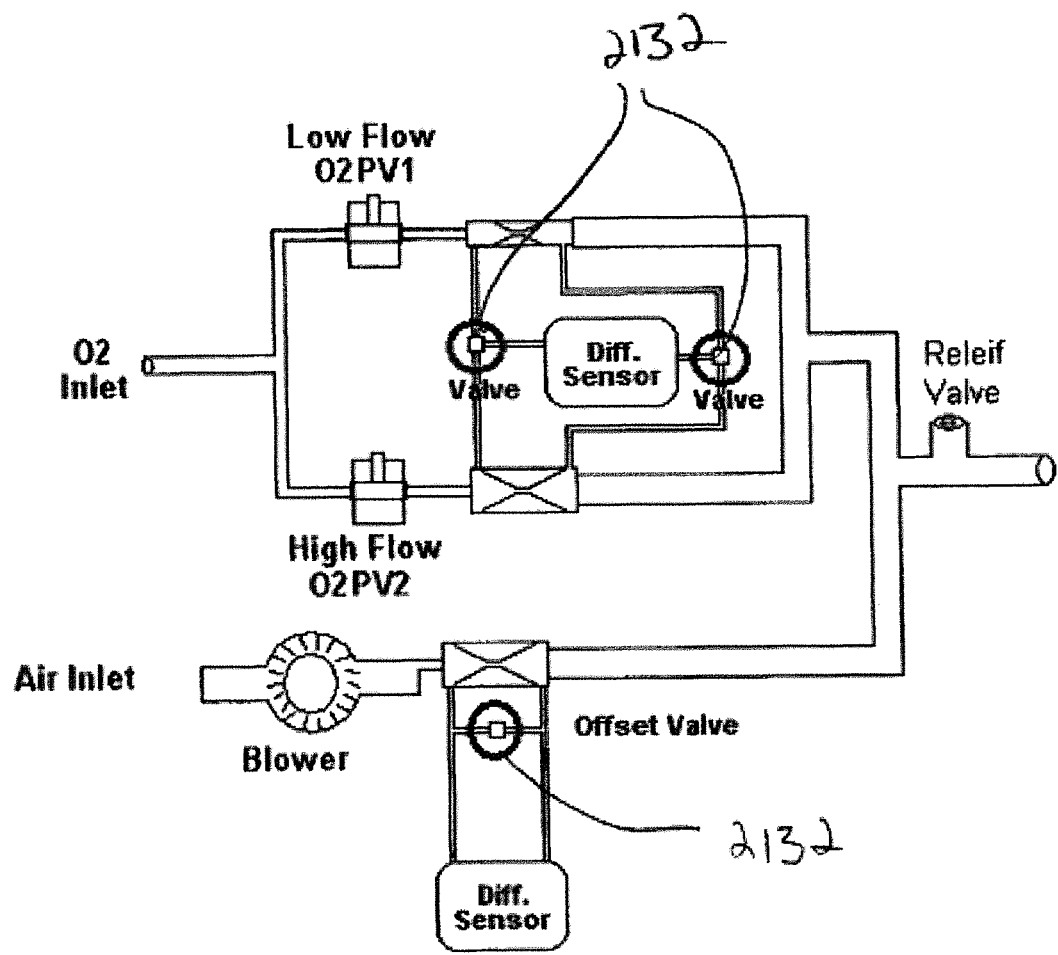
FIGS. 32A and 32B are schematic illustrations of the flow of gas according to embodiments of the present disclosure.
Figure 32B:
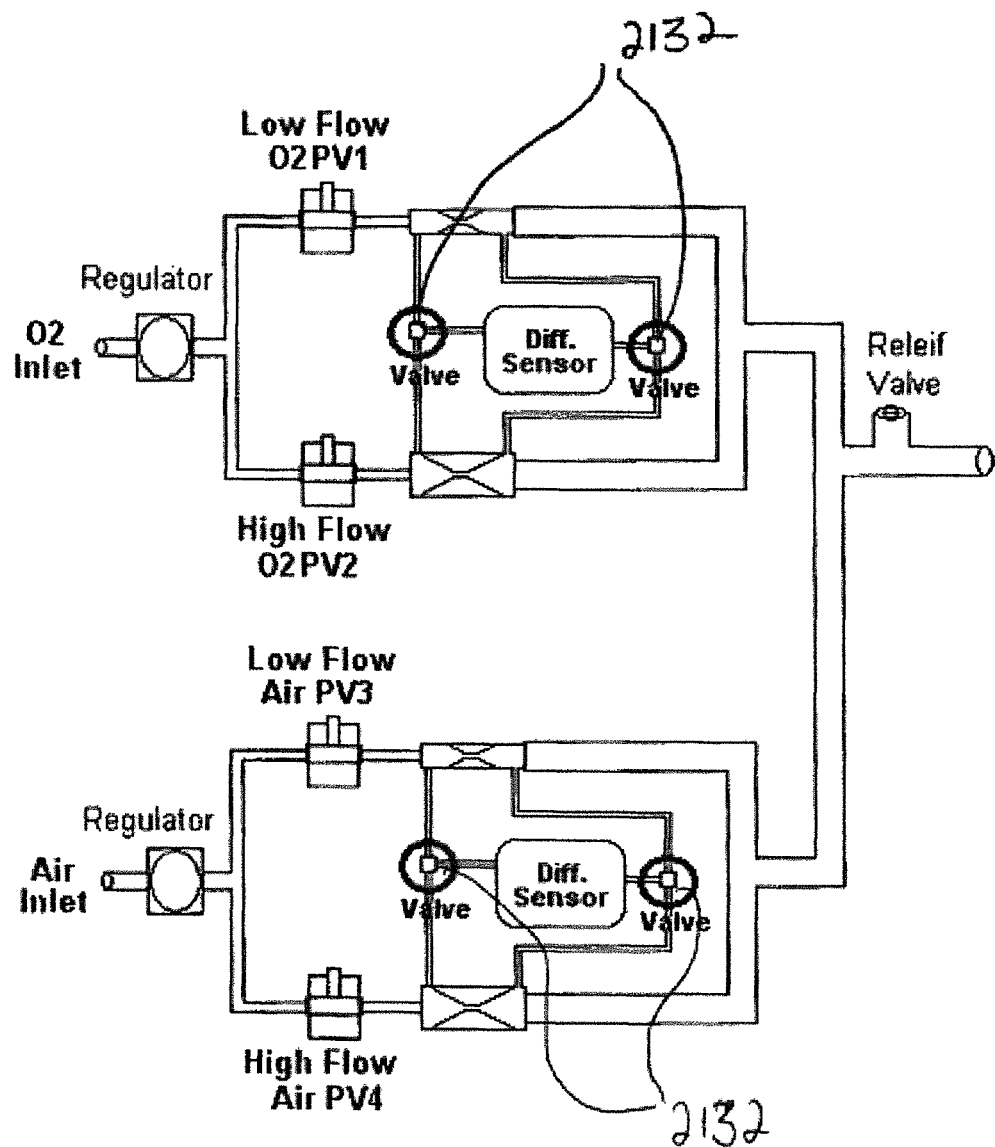

FIGS. 32A and 32B illustrate a schematic diagram of a further embodiment of an HFT device that allows for relatively low percentage gas mixtures, for example low $FiO_2$ when $O_2$ is mixed with air. In weaning a patient from $O_2$ therapy, it may be desirable to decrease a patient from a high percentage of $FiO_2$ to a low percentage of $FiO_2$, and in this case very small flows of $O_2$ may be needed in a mixture with air. For example, to deliver an $FiO_2$ of 25 percent at 5 liters per minute, as may be used in HFT in neonates; about 4.75 liters of air would be mixed with 0.025 liters of $O_2$. Conversely, to get a mixture of gases at higher ranges of $O_2$, low amounts of air would be mixed with $O_2$. The schematic illustrates how two proportional valves 2132 may be used to control flow over a wider range than would be effective with a single proportional valve. Also shown is how a single sensor may be configured to sense flow from two flow tubes (e.g., pneumotachs), in this instance, one for high and one for low volume flows.

HFT may be desirable for use in patients in locations where compressed or liquid $O_2$ is not readily or economically feasible. For patients who may benefit from oxygen therapy, an HFT device (e.g., 4100) may deliver gas from an oxygen concentrator. This gas may be mixed with room air. If 20 liters per minute room air is mixed with 6 liters per minute of $O_2$ from an oxygen concentrator delivering $O_2$ at 85% purity, the delivered gas mixture will have an $O_2$ concentration of about 36%. A higher concentration may be reached with the use of more than one oxygen concentrator.

The present disclosure also relates to a high flow therapy system 4500 including delivery conduit (such as delivery conduit 4200 described herein), therapy device (such as therapy device 4100 described herein), and connector (such as connector 4000 described herein). Delivery conduit 4200 is configured to direct gas towards a patient interface. Therapy device 4100 is configured to supply gas through a humidity chamber 4600 to delivery conduit 4200. Connector 4000 is configured to operatively connect delivery conduit 4200 with therapy device 4100, e.g., in a single motion. As shown in FIG. 25, in embodiments connector 4000 is configured to operatively connect delivery conduit 4200 with therapy device 4100 and humidity chamber 4600, e.g., in a single motion. Specifically, gas outlet 4110 of humidity chamber 4600 receives gas lumen 4010 of connector 4000, and receptacle 4150 of therapy device 4100 receives a flange 4250 of connector 4000. As is understood by one skilled in the art, flange 4250 would serve to orient connector 4000 relative to therapy device 4100 in order to facilitate alignment of previously mentioned temperature contacts, electrical contacts, pressure ports, etc. that may exist on both delivery conduit 4200 and therapy device 4100. In embodiments and as shown in FIGS. 25-26 gas outlet 4110 may have a first cylindrical portion and gas lumen 4010 may have a second cylindrical portion. It is understood that each cylindrical portion would have an axis. FIG. 27 shows a gas lumen axis 4011 and a gas inlet axis 4211. FIG. 27 also shows that outlet portion 4222 can have a cylindrical portion having an outlet port axis 4221. As shown in FIG. 27, in embodiments gas inlet axis 4211 may not be parallel to outlet port axis 4221.

Figure 29:
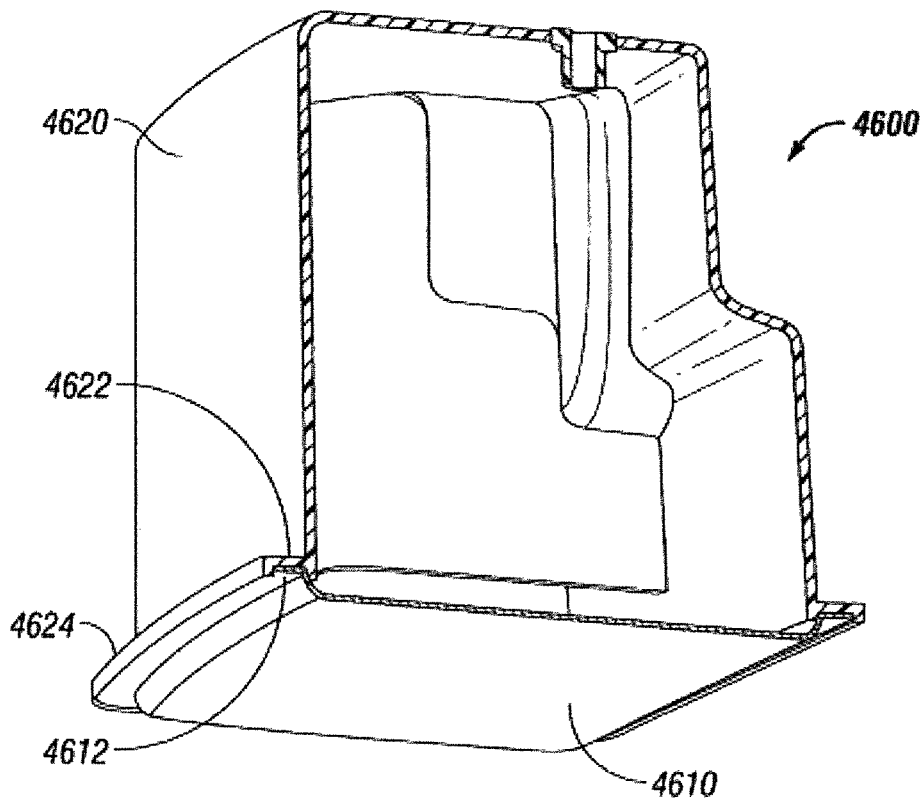
FIG. 29 is a transverse cross-sectional view of a humidity chamber of a therapy device according to an embodiment of the present disclosure.
Figure 29A:
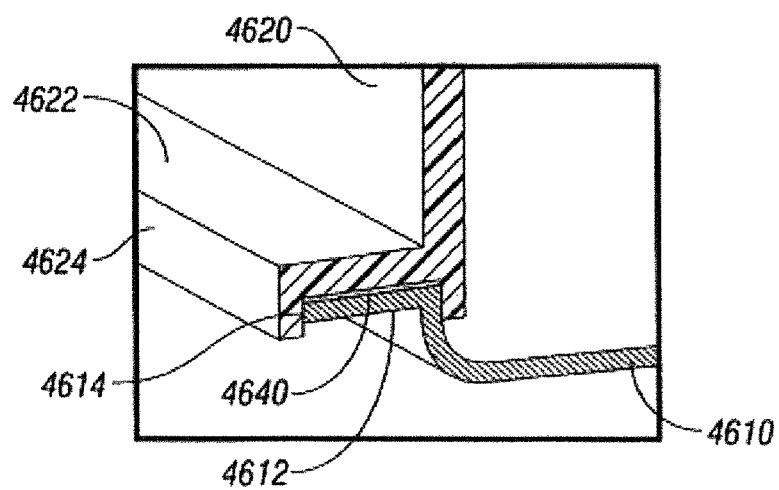
FIGS. 29A-29C are an enlarged sectional views of a portion of the humidity chamber according to embodiments of the present disclosure.
Figure 29B:
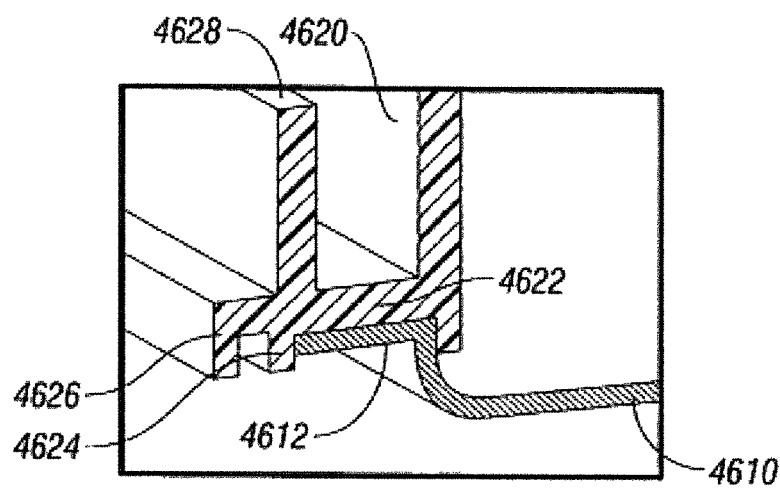
Figure 29C:
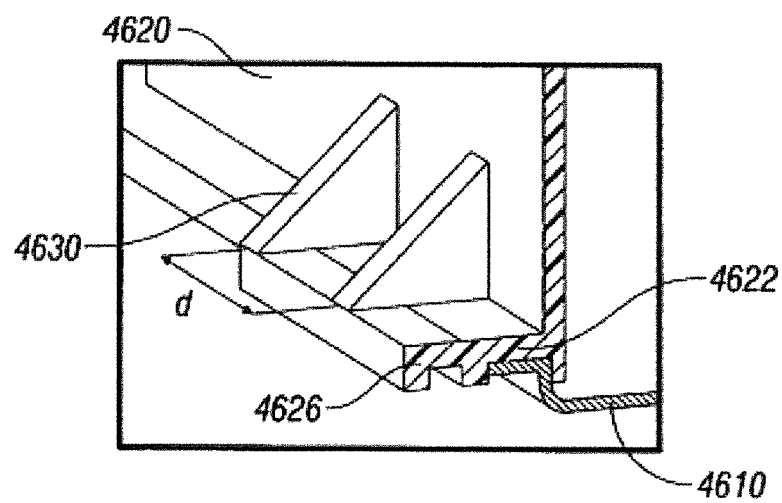

With reference to FIGS. 29-29C, various embodiments of a humidity chamber 4600 use with a therapy device (e.g., therapy device 4100) are shown. With particular reference to FIGS. 29 and 29A, humidity chamber 4600 includes heat transfer plate 4610 (e.g., made of aluminum) and a housing 4620 (e.g., made of thermoplastic). Housing 4620 includes a flange 4622 and a fixed barrier 4624. Flange 4622 is configured for engagement with a lip 4612 of heat transfer plate 4610. Fixed barrier 4624 extends along at least a portion of flange 4622 and is configured to shield an edge 4614 of heat transfer plate 4610.

As shown in FIG. 29B, an embodiment of humidity chamber 4600 includes an overhang 4626 extending from flange 4622/barrier 4624 and also includes a protrusion 4628 shown extending substantially vertically from flange 4622.

In the embodiment shown in FIG. 29C, humidity chamber 4600 also includes a plurality of ribs 4630 extending from a portion of housing 4620 and flange 4622. It is envisioned that a distance "d" between adjacent ribs 4630 is sufficiently small enough to prevent a user's finger from contacting flange 4622. For example, distance "d" may be between about 0.5 cm and about 1.0 cm.

As can be appreciated, various features of FIGS. 29-29C are helpful in protecting users from contacting a heated surface. Heat transfer plate 4610 is disposed in thermal communication with a heater plate (not explicitly shown in FIGS. 29-29C) of therapy device 4100. Thus, heat transfer plate 4610 (e.g., edge 4614 of heat transfer plate 4610) may reach a temperature that exceeds safety standards for an exposed surface. In the present disclosure, flange 4622 is positionable adjacent lip 4612 of heat transfer plate 4610 to help prevent an exposed surface from exceeding an allowable amount. The inclusion of other features (e.g., fixed barrier 4624, overhang 4626, protrusion 4628, and plurality of ribs 4630) of the present disclosure may further help prevent a user from being able to contact a surface having a temperature that exceeds safety standards.

Additionally, humidity chamber 4600 may also include a bonding agent 4640 disposed between lip 4612 of heat transfer plate 4610 and flange 4622 of housing 4620. Bonding agent 4640 (e.g., made from Dymax Medical Class VI Approved UV Cure Acrylic adhesive, or Star*Tech Medical Class VI Approved UV Cure Acrylic Adhesive) may be configured and positioned to provide a substantially watertight seal between heat transfer plate 4610 and housing 4620.

An embodiment of the present disclosure includes a humidity chamber 6000 that may be opened and washed (e.g., in a dishwasher), as shown in FIGS. 33A-33C. This allows for more economic use of an HFT device in the home. The upper housing 6010 is open and configured to mate with a seal 6020 (e.g., rubber or silicone) and a lid 6030. While various structures may be used to allow for a removable portion (e.g., a removable lid), the figures show the lid 6030 having one or more detachable hinges 6040a, 6040b on one surface that allow the lid 6030 to swing open to fill or refill the chamber. On the opposite surface a latch 6050 is included to help seal the lid 6030 closed. It is envisioned that the lid 6030 can be detached for washing.

With continued reference to FIGS. 33A-33C, humidity chamber 6000 illustrated in this embodiment also includes a gas inlet 6060, a gas outlet (not explicitly shown in the illustrated embodiments), a condensation bar 6070, finger protection flanges 6080, an overhang 6090 and a depression 6100 in lid 6030. Condensation bar 6070 is configured to help keep condensation from running out in rear of chamber when lid 6030 is open for refilling. It is envisioned that the chamber is configured to allow refilling without removing the chamber from the HFT device and thus allows fluid to be poured therein rather than solely relying on refilling via an IV bag. As shown, front latch 6040b helps enable lid 6030 to open. Overhang 6090 is configured to help seat lid 6030 correctly and to hold seal 6020 in place. Depression 6100 in lid 6030 is configured to act as a low point for the drippage of condensation.

Figure 30:
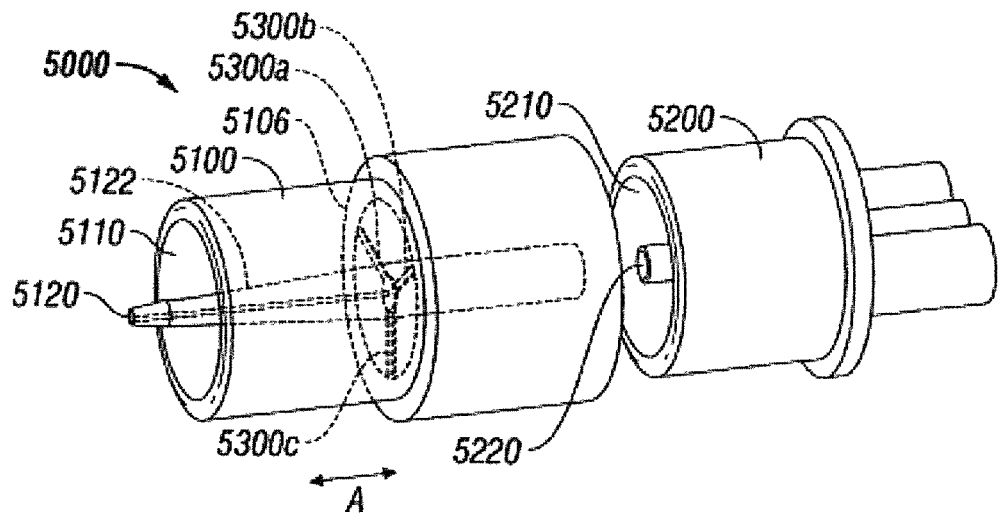
FIG. 30 is a perspective view of a connector according to an embodiment of the present disclosure.
Figure 31:
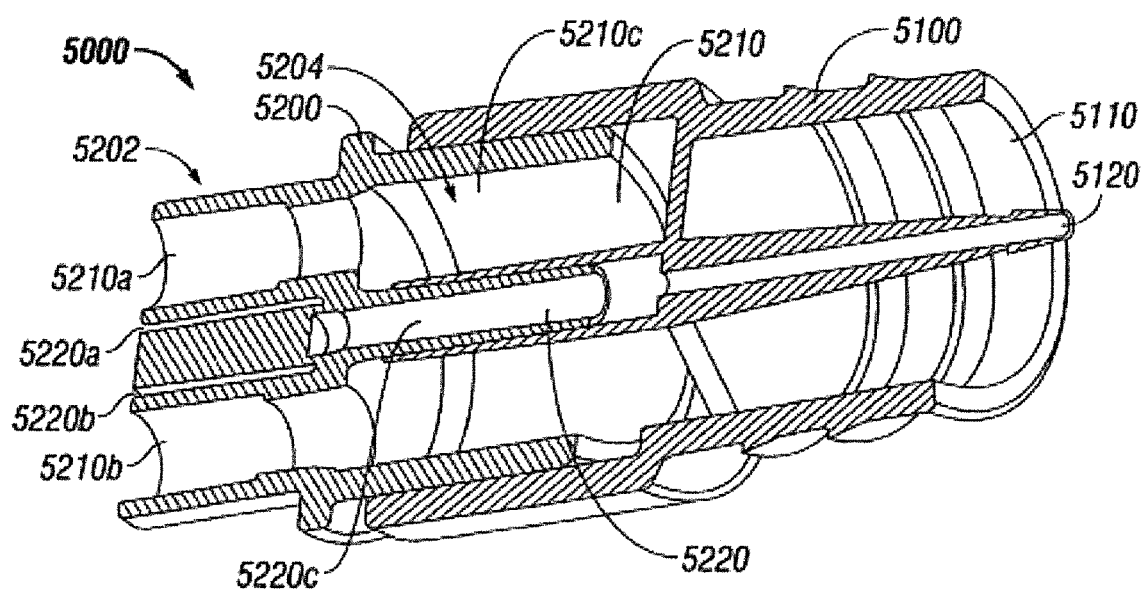
FIG. 31 is a longitudinal cross-sectional view of the connector of FIG. 30.

Referring now to FIGS. 30 and 31, a second connector 5000 for use with a therapy device (e.g., therapy device 4100) is shown. Second connector 5000 includes a conduit fitting 5100 for connecting to a cannula fitting 5200 of a patient interface. Conduit fitting 5100 includes a gas lumen 5110 and a pressure lumen 5120. Gas lumen 5110 is configured to direct gas from therapy device 4100 towards a patient interface (e.g., non-sealing respiratory interface 100). Pressure lumen 5120 is configured to convey pressure from a patient interface 100 towards pressure port 4120 of therapy device 4100. Cannula fitting 5200 is configured for releasable engagement (e.g., coaxial engagement) with conduit fitting 5100 and includes at least one gas lumen 5210 and at least one pressure lumen 5220. The at least one gas lumen 5210 of cannula fitting 5200 is configured to direct gas from therapy device 4100 towards patient interface 100. The at least one pressure lumen 5220 is operatively engageable with pressure lumen 5120 and is configured to convey pressure from patient interface 100 towards pressure port 4120 of therapy device 4100.

In the illustrated embodiments, a distal portion 5202 of cannula fitting 5200 includes two gas lumens 5210a and 5210b, which are in gaseous communication with gas lumen 5210c of a proximal portion 5204 of cannula fitting 5200. The illustrated embodiments also illustrate distal portion 5202 of cannula fitting 5200 includes two pressure lumens 5220a, 5220b in gaseous communication with pressure lumen 5220c of proximal portion 5204 of cannula fitting 5200. In these embodiments, gas may be supplied to and/or pressure may be taken from each of a patient's nostrils.

With continued reference to FIGS. 30 and 31, second connector 5000 further includes at least one spoke 5300 (three spokes 5300a, 5300b and 5300c are shown) connecting a wall 5106 of conduit fitting 5100 and a wall 5122 of pressure lumen 5120 of conduit fitting 5100. Spoke 5300 is configured to allow axial movement (e.g., in the substantial directions of arrow "A" in FIG. 30) of pressure lumen 5120 of conduit fitting 5100 relative to wall 5106 of conduit fitting. Thus, a pressure seal may be created between pressure lumen 5120 of conduit fitting 5100 and at least one pressure lumen 5220 of cannula fitting 5200 prior to a gas seal being created between gas lumen 5110 of conduit fitting 5100 and at least one gas lumen 5210 of cannula fitting 5200. That is, at least one spoke 5300 facilitates a single-motion connection between conduit fitting 5100 and cannula fitting 5200, e.g., by allowing pressure lumens 5120, 5220 to axially move together, while attempting to operatively couple (e.g., create a gas seal) gas lumens 5110, 5210.

It should also be noted that while spokes 5300 are illustrated and described as being part of conduit fitting 5100, it is envisioned and within the scope of the present disclosure to include at least one spoke 5300 on cannula fitting 5200 in addition to or alternatively from providing at least one spoke 5300 on conduit fitting 5100.

An embodiment of the present disclosure also relates to a therapy device including a gas delivery conduit that allows for delivery of therapeutic gases that may be warmed and humidified and delivered to a subject. A second conduit allows pressure from the subject's airway to be communicated to a sensor within the therapy device. This second conduit may be a gas conduit and may also allow for sampling of gas from the subject's airway. Such an embodiment may be useful, for example, in determining the expiratory $CO_2$ of the subject using the device.

In another embodiment, one or more pressure, temperature or other sensors may be placed in the subject's airway and may be used to provide data about the status of the subject receiving therapy and the subject's interaction with the therapy. Such sensors may be in electrical communication with a microprocessor 2060, and electric wires may be configured to follow or be within the delivery conduit. Data from sensors may also be transmitted optically. Optical fibers may transmit light that may be used to determine data about the subject's status and about the subject's interaction with the therapy. Optical fibers may be used in conjunction with certain sensors or in collaboration with electrical sensors. Further, optical fibers may be configured to follow or be disposed within the delivery conduit. The connector used in this embodiment may include contacts for a gas port for sensors, electrical contacts for sensors and/or optical connectors.

Running the HFT unit without water could deliver dry warm air to the user. One aspect of the present disclosure is the ability of the unit to give a signal, which notifies the user that the unit has run low on water or is out of water to supply the needs to humidify the gas delivered. At least one of temperature data and power data of the heaters can be used to determine status of the water level in the humidity chamber 2020. Additional aspects of the present disclosure include the ability of the unit to signal a low water status, and to shut itself off or re-adjust flow and heater settings in response to low water. Another aspect of the present disclosure is the ability to trigger automatic refilling of the humidity chamber with water, by opening a valve controlling the inlet of an appropriate amount of water upon a signal from the microprocessor 2060.

After use, water or moisture may remain in the humidity chamber 2020 or conduit. This is a potential area for growth of microbes. Another aspect of the present disclosure is a drying cycle, where the heater and blower are active, and run until the humidity chamber 2020 and the conduit are substantially dry. This helps prevent the growth of common microbes in the humidity chamber 2020 and the conduit. It is envisioned that monitoring at least one of temperature and current use by the unit helps control the drying cycle. That is, it is envisioned that microprocessor 2060 is able to detect changes in electrical current use and/or temperature data and can use this information to determine that the amount of water in the humidity chamber is inadequate for continued use. In response to an inadequate amount of water, microprocessor 2060 may trigger an auditory and/or visual signal, may trigger a mechanism (e.g., water supply) to add water to the chamber, and/or may adjust the delivered gas flow temperature and/or flow rate.

FIGS. 34A-34D illustrate a saddle 7000 where a portion of the conduit may be seated. In one configuration, the user places a portion of the conduit in a saddle 7000, or other connector. It is envisioned that when the conduit in positioned in the saddle 7000, a signal is sent to the unit to run the drying cycle until the humidity chamber 2020 and the conduit are dry and then to turn the unit off. It is also envisioned that the saddle 7000 is configured to help prevent the unit from being used by a patient during the drying cycle, which may operate at higher temperatures. In such an embodiment, it is envisioned that there are sensors 7100a, 7100b (e.g., electrical sensors, magnetic sensors, mechanical sensors, etc.) disposed on the saddle 7000 and the conduit that must be engaged with one another to enable the drying cycle to run.

The present invention is a respiratory gas delivery system that delivers high flows (i.e. high flow therapy) through a non-sealing patient interface. This High Flow Therapy (HFT) system is comprised of a HFT device (i.e. the main device) and its accessories, which are described in further detail throughout. The HFT device can provide respiratory support for patients ranging from neonates to adults. The HFT device can lower respiratory rates, improve secretion clearance, and reduce the work of breathing. The HFT device can relieve respiratory disorders that respond to certain levels of positive airway pressures, such as asthma, bronchitis, sleep apnea, snoring, COPD, and other conditions of the respiratory tract. For example, the HFT system could deliver up to 35 cm H2O of airway pressure. The HFT device can treat hypothermia and aid in washout of anesthetics after surgery. It is envisioned that the HFT device may have applications similar to those prescribed hypobaric chambers, such as brain or head injury (e.g. concussions). The present disclosure relates to a high flow therapy system for delivering heated and humidified respiratory gas to an airway of a patient. The HFT device can generate flows that are continuous. The HFT system delivers the gases to the patient via a non-sealing patient interface (e.g. nasal cannula) utilizing an "open flow" method of delivery. "Open Flow" specifies that the cannula in the patient's nose does not create a seal or near seal.

The HFT device is an all-in-one device that allows for control of gas flow, gas oxygen concentration, gas temperature, and gas humidity in a single device or system. This includes delivering gases at flow rates up to 60 L/min, oxygen concentrations up to 100%, gases heated from 30 to 40 degrees Celsius, and humidified gases up to 100% relative humidity. The is vastly superior to basic oxygen delivery systems that are limited to gas flows of up to 8 L/min, have no gas temperature control, and have no gas humidity control. Because basic oxygen delivery systems have no gas temperature or gas humidity control, gas flows higher than 8 L/min are not well tolerated by the patient. In contrast, the HFT device can deliver higher flow rates that are easily tolerated in the nasal passages when the gas is warm and humid. The high flow also assures that the patient's inspired volume may be almost entirely derived from the gas delivered (i.e. minimized or no mixture of delivered gas with ambient air). The HFT system may generate a positive pressure in the airways during inhalation and/or exhalation, even though the system is an open system (i.e. does not use a sealing patient interface).

An all-in-one HFT device allows for more control and more accuracy of the gas conditions being delivered. It also provides the opportunity to provide feedback to the operator and to provide feedback loop control of the HFT device through for example gas sensing. Finally, an all-in-one HFT device allows for improved communications and alarms to the operator. For example, the HFT device may gather airway pressure information through its pressure sensing technology described throughout and use that information to adjust flow rates (either manually by the operator or automatically by the HFT device) in order to control airway pressures (e.g. prevent unintended high pressures).

Figure 36:
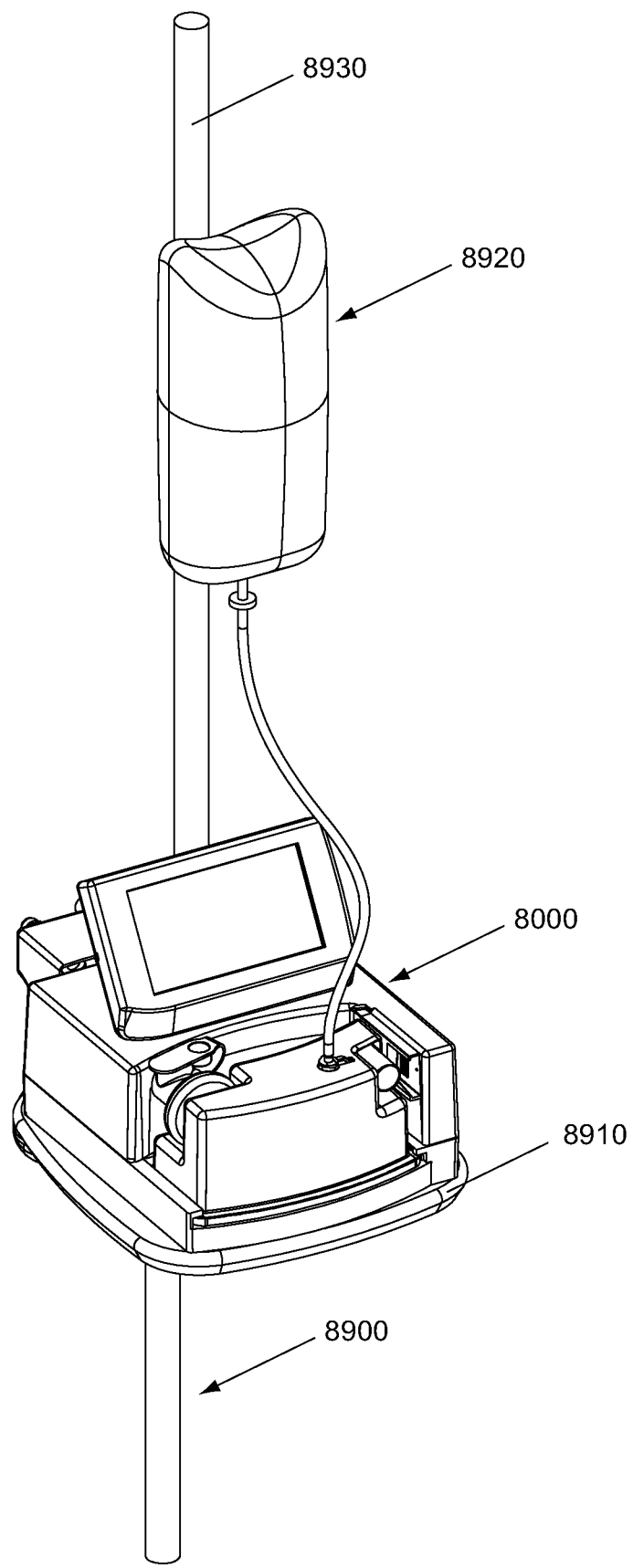
FIG. 36 illustrates a perspective view of a high flow therapy system positioned on a cart in accordance with an embodiment of the present disclosure.
Figure 37:
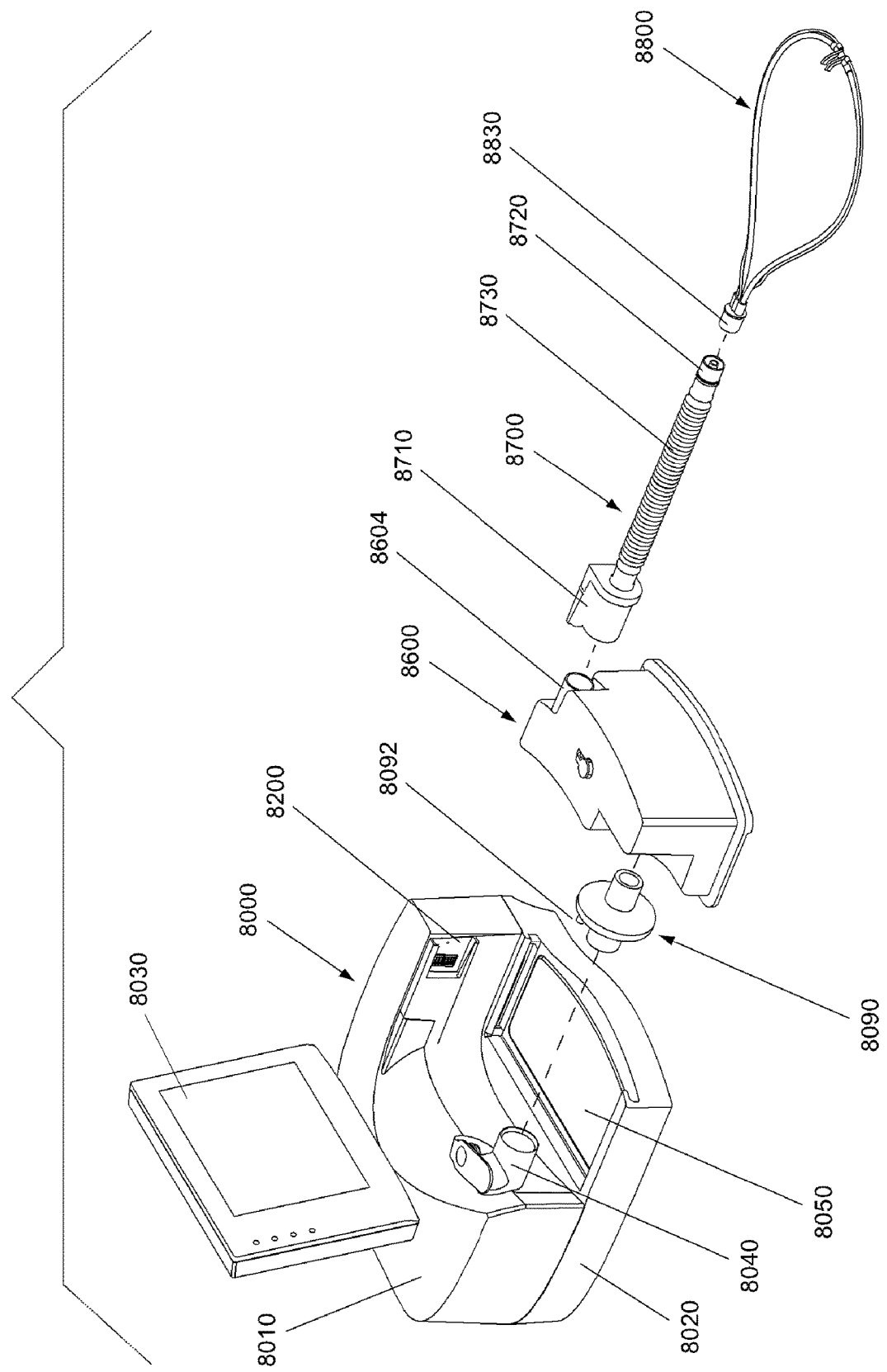
FIG. 37 illustrates an exploded view of the high flow therapy system of FIG. 36 illustrating the major components in a disassembled relationship, in accordance with an embodiment of the present disclosure.
Figure 38:
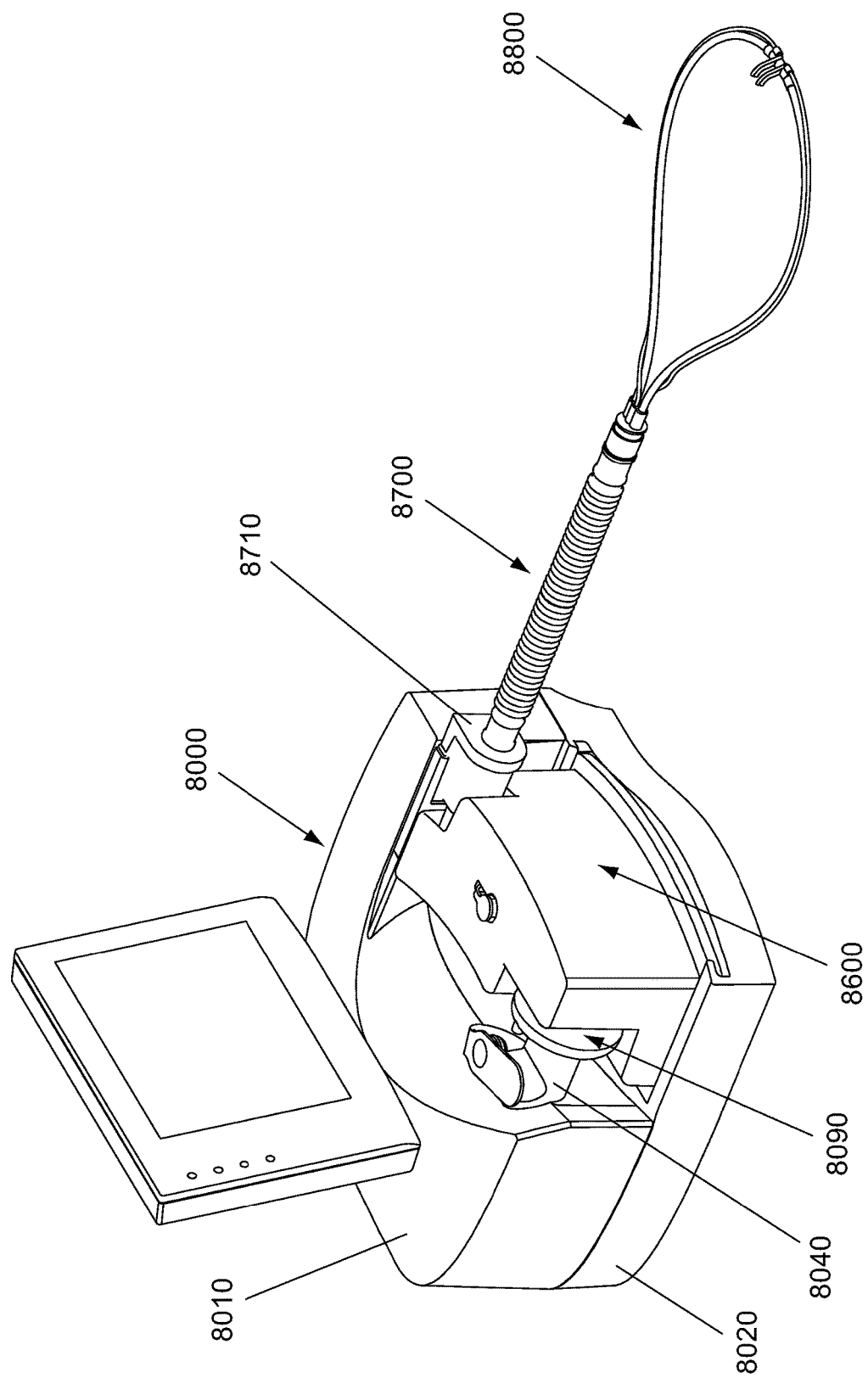
FIG. 38 illustrates an assembled view of the high flow therapy system of FIG. 36 illustrating the major components in an assembled relationship, in accordance with an embodiment of the present disclosure.
Figure 39:
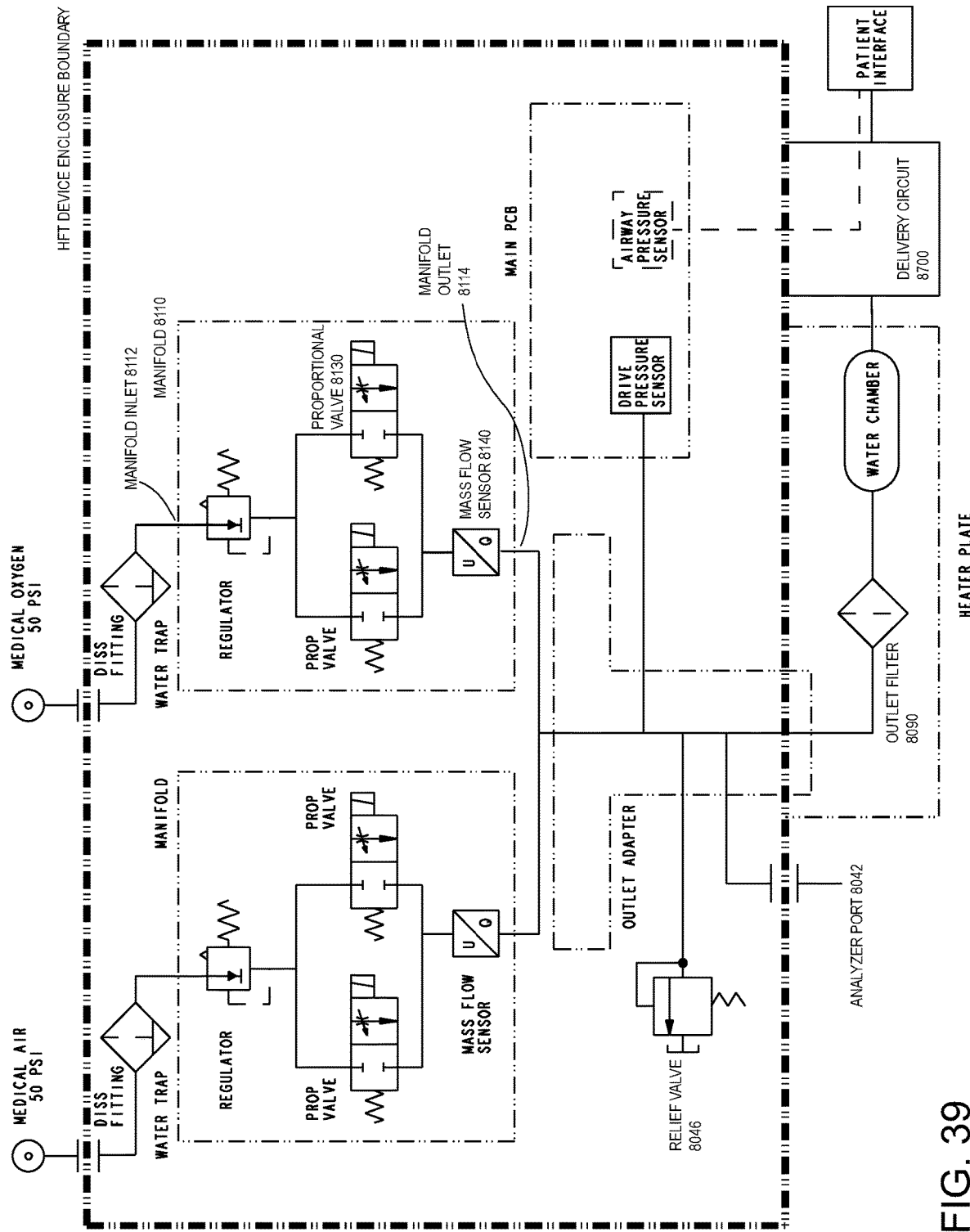
FIG. 39 illustrates a schematic view of the high flow therapy system of FIG. 36 in accordance with an embodiment of the present disclosure.

The HFT system is a microprocessor-controlled respiratory gas delivery system that provides continuous flows of heated and/or humidified air and/or oxygen mixtures to patients. FIG. 36 illustrates of an embodiment of a HFT device 8000 of a HFT system that is positioned on a platform 2900 of a cart 8900 and coupled with a water bag 8920. FIG. 37 illustrates an exploded view of some of the main components of an HFT system, including the HFT device 8000, the water chamber 8600, the delivery circuit 8700, and the patient interface 8800. FIG. 38 illustrates an assembled view of some of the main components of an HFT system. FIG. 39 illustrates a schematic view of some of the main components of an HFT system. The HFT device 8000 can be controlled by a microprocessor on a main PCB (printed circuit board) 8060. The operator of the HFT device inputs settings, such as gas flow rate, gas temperature, gas oxygen concentration, gas humidity levels, etc. via the HFT device's user interface for the microprocessor to control. The user interface may be a graphical user interface (GUI). The user interface may contain information such as graphs (e.g. pressure waveform), numbers, alpha characters, help menus, etc. The user interface may be shown on a display 8030. The display 8030 can have a touch screen that allows the operator make inputs to the HFT device. The display 8030 can be rotated, for example up to 360 degrees, to facilitate viewing or entry. The display 8030 can be pivoted or tilted, for example from 0 to 180 degrees, to facilitate viewing, entry, or shipping. The display 8030 can be removable to facilitate shipping, servicing, or to be used as a portable user interface. The HFT device can also include push buttons or knobs as part of the user interface system. In alternative embodiments, the information on the display 8030 may be projected by the HFT device (e.g. on a wall or on a table) or the information may be transmitted onto another device, such as a hand held device or computer. In another alternative embodiment a separate device, such as phone, tablet, or computer may couple with the HFT device in lieu of the display 8030 or may transmit information to the HFT device in order to serve as the user interface.

Figure 40:
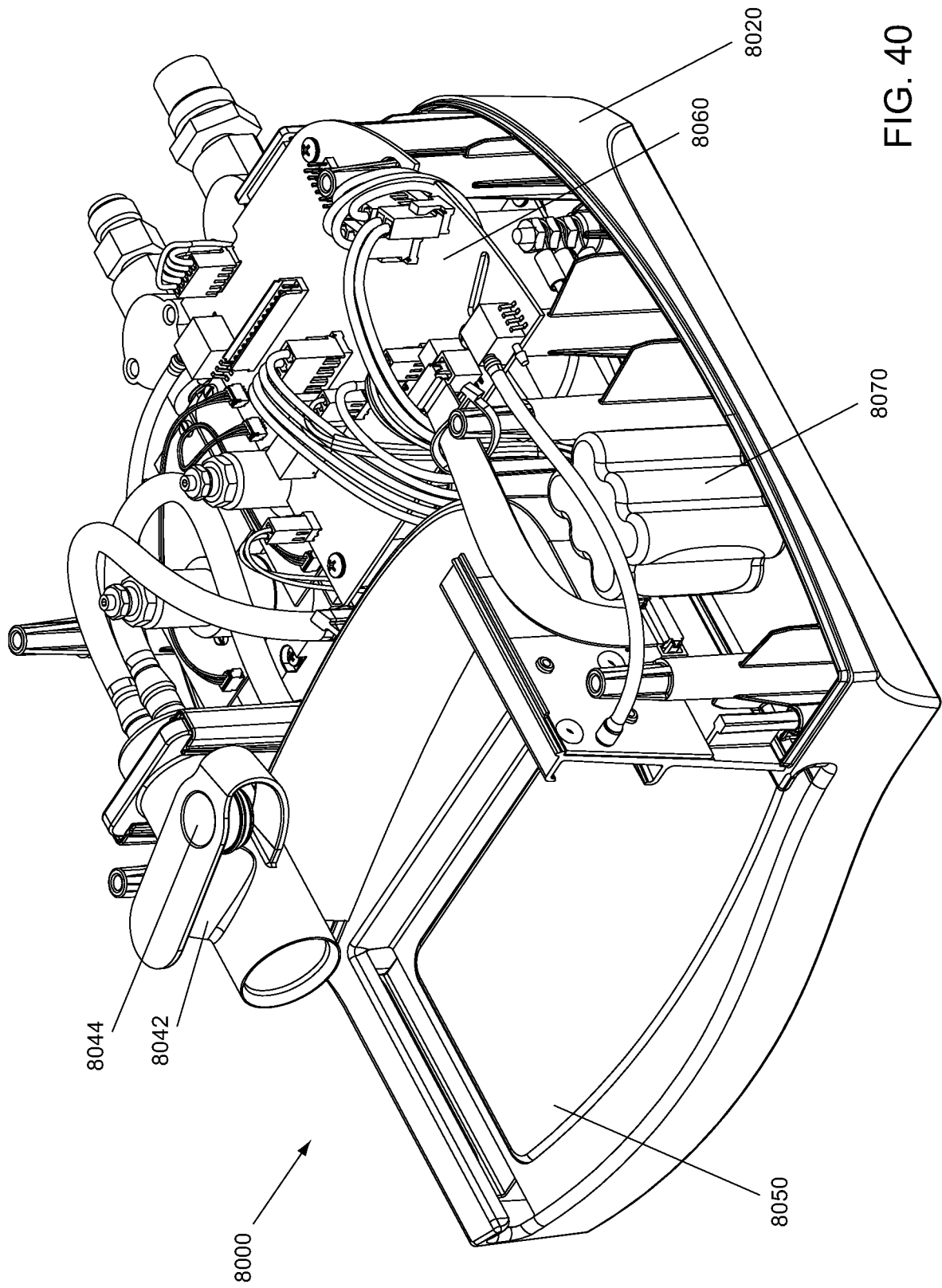
FIG. 40 illustrates a top perspective view of the high flow therapy device of FIG. 36 showing internal components with the upper enclosure removed, in accordance with an embodiment of the present disclosure.
Figure 41:
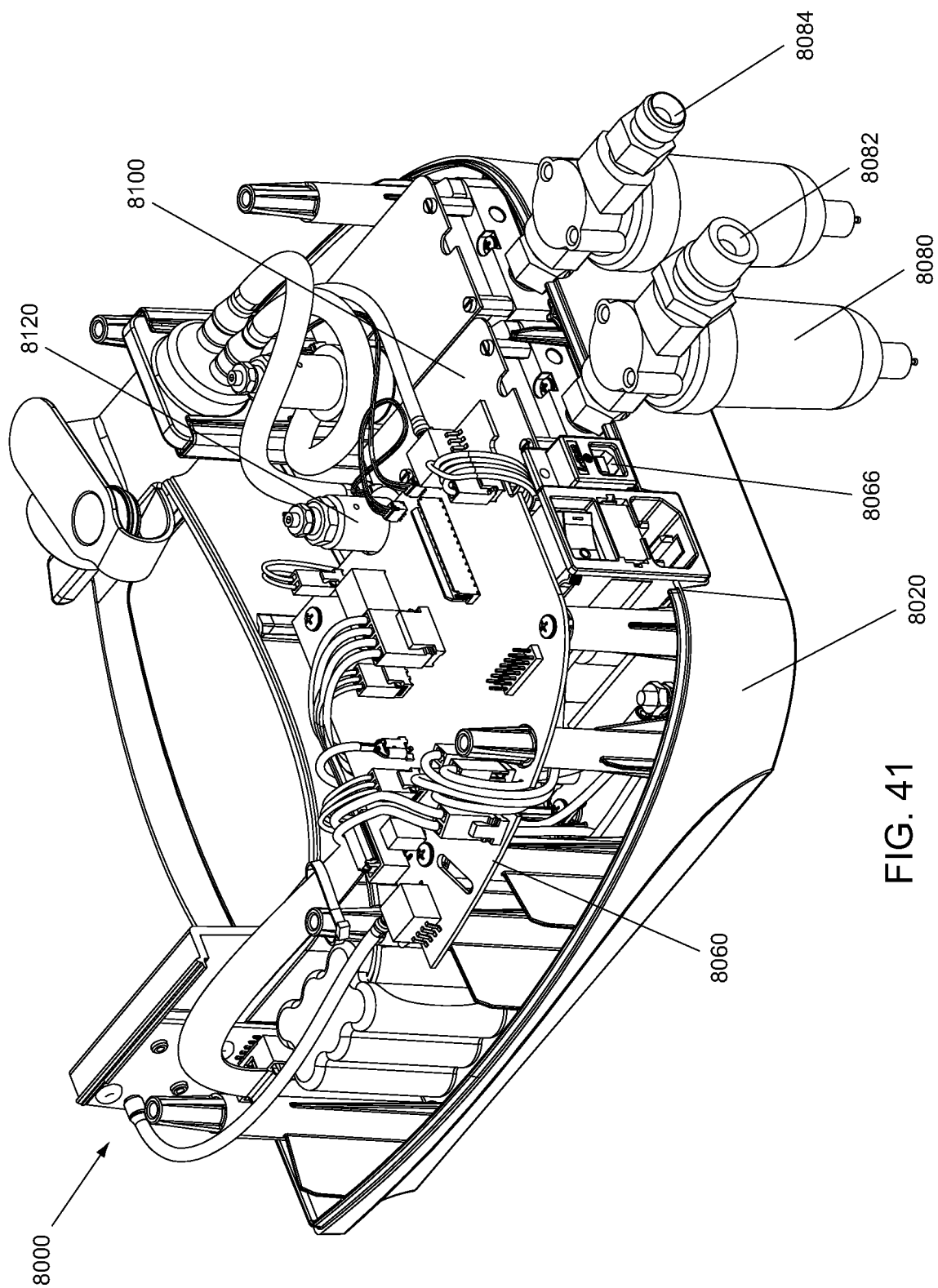
FIG. 41 illustrates a rear perspective view of the high flow therapy device of FIG. 36 showing internal components with the upper enclosure removed, in accordance with an embodiment of the present disclosure.
Figure 42:
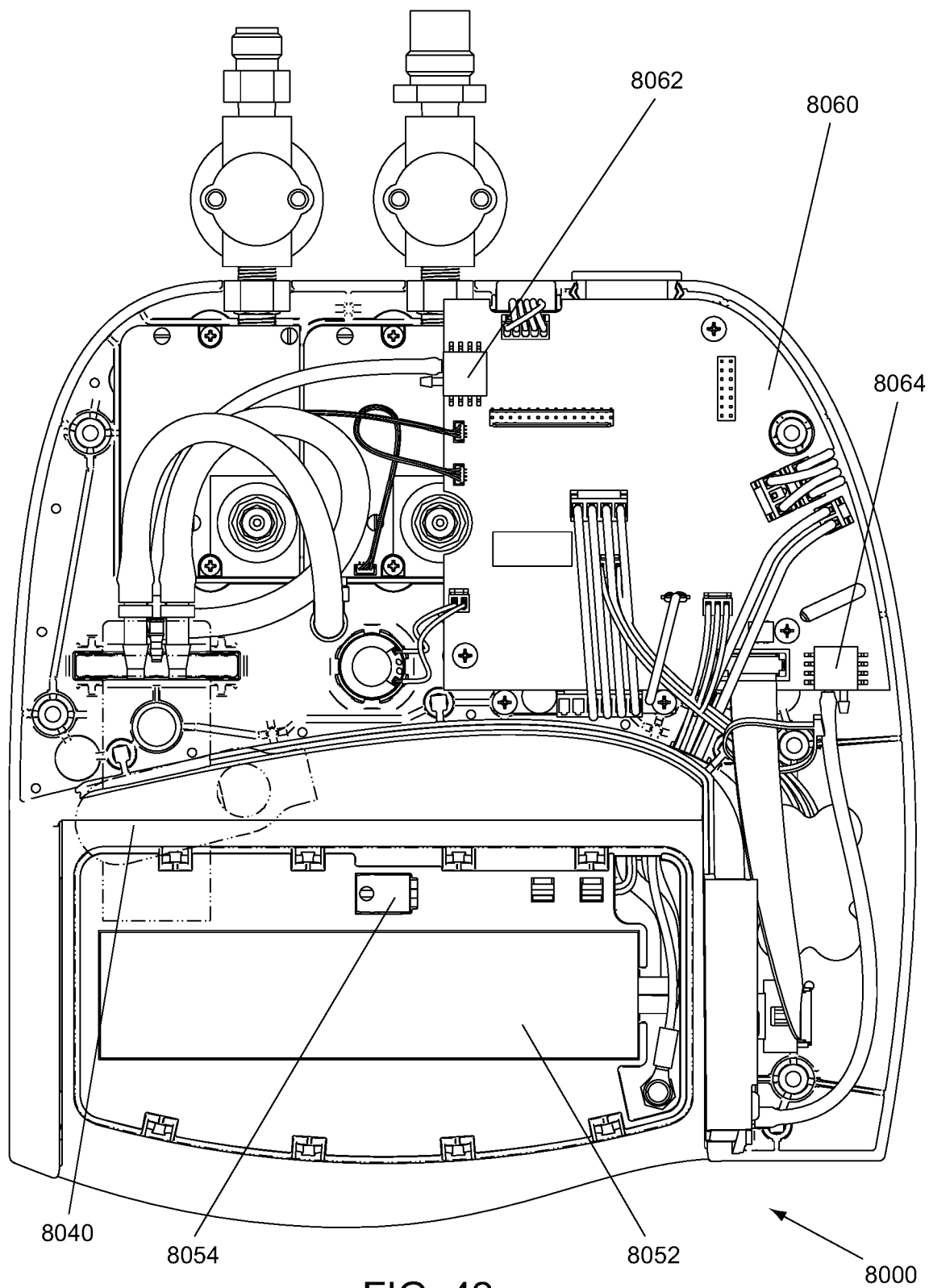
FIG. 42 illustrates a top view of the high flow therapy device of FIG. 36 showing internal components with the upper enclosure removed, the heater plate shown transparent, and the outlet adapter shown transparent, in accordance with an embodiment of the present disclosure.

The HFT device 8000 may have an enclosure with an upper enclosure portion 8010 and a lower enclosure portion 8020 as shown in FIG. 37. FIG. 40 illustrates a top perspective view of the HFT device 8000 with the upper enclosure portion 8010 removed to show some of the internal components. FIG. 41 illustrates a rear perspective view of the HFT device 8000 with the upper enclosure portion 8010 removed to show some of the internal components. FIG. 42 illustrates a top view of the HFT device 8000 with the upper enclosure portion 8010 removed, the heater plate 8050 shown transparent, and the outlet adapter 8040 shown transparent to show some of the internal components. The HFT device 8000 may have a battery 8070 so that it may work, at least partially, as a portable device, without being plugged in, or without wall power (e.g. as a backup battery in a power outage). The HFT device may be mounted on a pole 8930, on a cart 8900, or may be configured to be placed on a table, desk, or nightstand.

Medical grade air and/or medical grade oxygen, for example from hospital gas supply systems or compressed gas tanks, may be used with the HFT system. Other gases, such as helium, may be substituted for the air or oxygen. An inlet filter 8080 (e.g. a water trap) can be connected between a gas source and the HFT device 8000 via a fitting 8082 (e.g. DISS fitting). The inlet filter 8080 could be internal or conversely external to the HFT device so it is visible and accessible for service. The pressurized gas (e.g. air or oxygen from the facility at 50 psi) then enters the HFT device 8000 and its flow system. There may be two inlet filters as shown in FIG. 41. There may be two different fittings (e.g. fitting 8082 and second fitting 8084) for connecting the HFT device 8000 with different gas sources.

The HFT device can have an integrated flow adjustment system to deliver the set flow rate and/or oxygen concentrations to the patient. Flow control can be achieved automatically through the interaction between the system electronics (e.g. the microprocessor) and the flow system. The flow system can consist of valve systems. Valve systems can be used for air and/or oxygen gas flow regulating and metering. The valve systems can be partially or completely enclosed in the HFT device.

A valve system 8100 can be a manifold 8110 (e.g. a molded housing or machined block of plastic or aluminum). A manifold 8110 can have one manifold inlet 8112, one manifold outlet 8114, and one manifold flow path there between. In an alternate embodiment, a single manifold can have a first manifold inlet, a first manifold outlet, and a first manifold flow path there between, as well as a second manifold inlet, a second manifold outlet, and a second manifold flow path there between. In a preferred embodiment, there are two valve systems inside the unit—one for air and one for oxygen. A regulator 8120 can be mounted on the manifold 8110. The regulator 8120 can reduce the gas pressure from its initial pressure (e.g. 50 psi) to a lower or constant pressure that is optimal for subsequent flow rate control inside the device. The pressurized gas flows from the manifold inlet 8112 to the regulator 8120 that is mounted on the manifold 8110. After leaving the regulator 8120, the gas flows through a proportional valve 8130 that can also be mounted on the manifold 8110. The proportional valve 8130 can be a piezo-actuated proportional valve. The proportional valve 8130 can output a gas flow rate proportional to a signal voltage. The proportional valve 8130 is normally closed when no gas flow is required through the valve. In a preferred embodiment, each valve system can have two proportional valves, where a first proportional valve accommodates higher flow rates (e.g. 50 L/min) and a second proportional valve accommodates lower flow rates (e.g. 1 L/min). In this embodiment, the two proportional valves may work independently or may work in cooperation.

The valve system 8100 can have a mass flow sensor 8140 coupled with the manifold 8110 to measure the flow rate of the gas. The mass flow sensor 8140 is coupled to a manifold PCB (printed circuit board), which can be mounted to the manifold 8110. The manifold PCB is electrically connected to the main PCB 8060 to communicate input/output signals and power. This system can be referred to as a 2-position (i.e. on and off), 2-way (i.e. gas in and gas out) piezo-based valve system with integral mass flow metering system. This system can be described as a low-power, highly-sensitive piezo valve working in conjunction with a mass flow sensor and with control loop electronics to achieve accurate flow rates with little power consumption. The results are that the valve systems can be very quiet and cool, eliminating the needs for fans or secondary cooling devices (e.g. heat sinks) inside the HFT device. This integrated flow adjustment system described in the sections above forms a control loop by which the gas flow may be adjusted by the software of the HFT device.

Gas exists the manifold 8110 through the manifold outlet 8114. In an embodiment with two manifolds (i.e. one for each gas), the gases exit their respective manifolds and stream together to mix. This mixing can occur in a tube, a mixing chamber, a blender, etc. In an embodiment with one manifold for two different gases, the gases may stream together within the manifold to mix prior to exiting the manifold (i.e. two manifold inlets and one manifold outlet).

In another embodiments, the HFT device can entrain air from ambient instead of receiving it from a compressed gas source. In yet another embodiment, the HFT device can have an integral blower for air to advance the gas. Both of these embodiments could replace the air valve system and integrate with the flow adjustment system. Gas from these embodiments could still mix with the oxygen downstream as previously described.

Mixed gases can then proceed towards and through an outlet adapter 8040. Pressure inside the outlet adapter 8040 can be measured by a drive pressure sensor 8062. The drive pressure sensor 8062 can be located on the main PCB 8060 and can be pneumatically connected to the bore of the outlet adapter 8040 by a length of flexible tubing. If the pressure inside the outlet adapter 8040 exceeds a certain pressure (e.g. 1 psi), the gas may be vented out of the outlet adapter 8040 through a relief valve 8046.

The end of the outlet adapter 8040 may protrude outside the HFT device 8000 enclosure. The outlet adapter 8040 can feature an oxygen analyzer port 8042 into which an oxygen analyzer may be connected to for oxygen concentration (e.g. FiO2) verification purposes. The oxygen analyzer port 8042 may be closed by a valve, plug, or cap when an analyzer is not in use. Such a feature may be coupled or integral with the outlet adapter 8040 to close off of the oxygen analyzer port 8042. An analyzer adapter may be inserted into the oxygen analyzer port 8042 to allow the fit of different sizes of oxygen analyzers. In one embodiment, an analyzer adapter 8044 may be integrated into the outlet adapter.

An outlet filter 8090 may be connected to the outlet adapter 8040 (e.g. via press fit). This outlet filter may have viral and/or anti-bacterial properties. The outlet filter 8090 serves to keep bacteria, viruses, volatile organic compounds, etc. from entering the water chamber and eventually reaching the patient. The outlet filter 8090 also serves to keep water, humidity, bacteria, viruses, etc. from entering the HFT device itself. This keeps undesirable matter from collecting inside the HFT device and potentially being transmitted to the next patient that uses the HFT device. The outlet filter 8090 therefore is a safety component to reduce risks to the HFT device and the patient from use of the HFT device. The outlet filter 8090 may have a outlet filter gas sampling port 8092. The outlet filter 8090 may have a straight, angled, or staggered filter body portion, filter inlet gas port, and/or filter outlet gas port. The end of the outlet adapter 8040 may be closed by a valve, plug, or cap when the outlet filter 8090 is not engaged, for example between use of the HFT device on different patients. Such a feature may be coupled or integral with the outlet adapter 8040 and would serve to protect the inside of the HFT device when an outlet adapter 8040 is not present.

The outlet filter and the other components downstream may be considered single use, single patient use, or disposable components. These components may include a water chamber, a delivery circuit, a patient interface (e.g. cannula; mask; or artificial airways such as endotracheal tubes, nasotracheal tubes, and tracheotomy tubes), a tee, and/or other fittings. It is preferred that the patient interface be a non-sealing interface (i.e. not intended to form a substantial seal with the patient), such as a non-sealing nasal cannula.

The water chamber 8600 slides into the HFT device 8000 and subsequently engages with outlet filter 8090 (via a friction fit). The HFT device has receiving flanges that couple with the water chamber 8600. The receiving flanges can be spring loaded to facilitate securing the water chamber 8600 and/or to facilitate keeping contact between the heat transfer plate of the water chamber 8600 and the heater plate 8050. The water chamber 8600 can maintain in the HFT device via an upward force and/or friction between the water chamber 8600 and the HFT device 8000. The water chamber 8600 can be inserted or removed without having to manipulate (e.g. press down) another feature, such as latch or bar.

The water chamber 8600 has a water chamber gas inlet and a water chamber gas outlet 8604. The water chamber gas inlet can have a water chamber gas inlet axis and the water chamber gas outlet 8604 can have a water chamber gas outlet axis. The water chamber gas inlet axis and the water chamber gas outlet axis may be parallel. Further, a plane drawn between the water chamber gas inlet axis and the water chamber gas outlet axis may be parallel to a typical table, nightstand, or desk located in the use environment, a platform 8910 on a cart 8900 or I.V. pole (e.g. pole 8930) where the HFT device may be placed during use, or the bottom of the HFT device itself. The gas moves through the water chamber 8600 picking up heat and/or humidity and then into the delivery circuit 8700. It is preferred that the humidified gas that exits either the water chamber 8600 not enter into or through a portion of the HFT device itself to avoid risk of contamination or the need to clean or disinfect that portion of the HFT device prior to use on another patient.

The water chamber 8600 can consist of a housing that is clear (e.g. made of a resin such as polystyrene) that allows the operator to see the water level inside. The water chamber 8600 can have a heat transfer plate (e.g. made of metal such as aluminum). The heat transfer plate may be bonded to the housing (e.g. UV cured adhesive). In an alternate embodiment, a gasket (e.g. an o-ring) may be used to couple and/or seal the heat transfer plate to the housing. The water chamber 8600 may have an inlet baffle on the water chamber gas inlet to prevent water from splashing towards the outlet filter 8090. The water chamber 8600 may have an outlet baffle on the water chamber gas outlet 8604 to prevent water from splashing towards the delivery circuit 8700, for example during movement or transportation of the HFT device.

The operator may fill the water chamber 8600 manually with water up to a maximum level, which may be indicated by markings on the water chamber 8600. In a preferred embodiment, the water chamber 8600 may have an automatic filling system to replace the otherwise manual process of filling the water chamber 8600 with water from a sterile water bag (e.g., water bag 8920) that is suspended above the HFT system. In a manual arrangement, the operator must attend to the device periodically, as needed, in order to verify that the water chamber 8600 is being kept at a water level that is adequate for the device to function normally. If the water level is too low, water must be added to the water chamber 8600. The manual filling process usually involves the operator physically releasing a pinch valve (or other valve mechanism) that normally impedes water flow from the sterile water bag's tubing and waiting a few moments for the water chamber 8600 to fill to the correct level before re-closing the valve. Maintaining a water level that is adequate for normal device function is necessary to prevent unwanted interruptions to therapy. If the water chamber 8600 is allowed to reach a very low level or empty water level, the device may signal an audible alert. If the low water condition is not addressed in time, the device may either continue to supply under-humidified respiratory gas or may automatically pause the gas delivery until the condition is resolved. The advantages of an automatic filling system is that it ensures an adequate water level (e.g. a continuous level, such as a predetermined minimum level) in the water chamber 8600 until the water bag 8920 is empty and that it eliminates the need for operator involvement in the interim. With the automatic filling system, when the water is released into the water chamber 8600 from the water bag 8920, the water level inside the water chamber 8600 will rise until a plastic float component inside seals the fill port. As the water is consumed by the heated humidification process, the water level falls and the float lowers, allowing more water from the water bag 8920 to fill the water chamber 8600 again until the port is re-sealed. If left unattended, this process will continue until the water bag 8920 is completely empty.

The delivery circuit 8700 provides a conduit for the heated and/or humidified respiratory gas as the gas is transported from the water chamber 8600 to the patient interface. The delivery circuit 8700 may have a heating element inside, such as a heated wire 8740. The heated wire 8740 may extend through some or all of the delivery circuit. The heated wire 8740 may be straight, coiled like a spring, or embedded in the delivery circuit 8700. The delivery circuit 8700 actively maintains the desired humidity and temperature parameters of the gas and prevents and/or minimizes rainout or excessive moisture condensation inside the delivery circuit 8700. Rainout is a concern for the safety of the patient.

Figure 43:
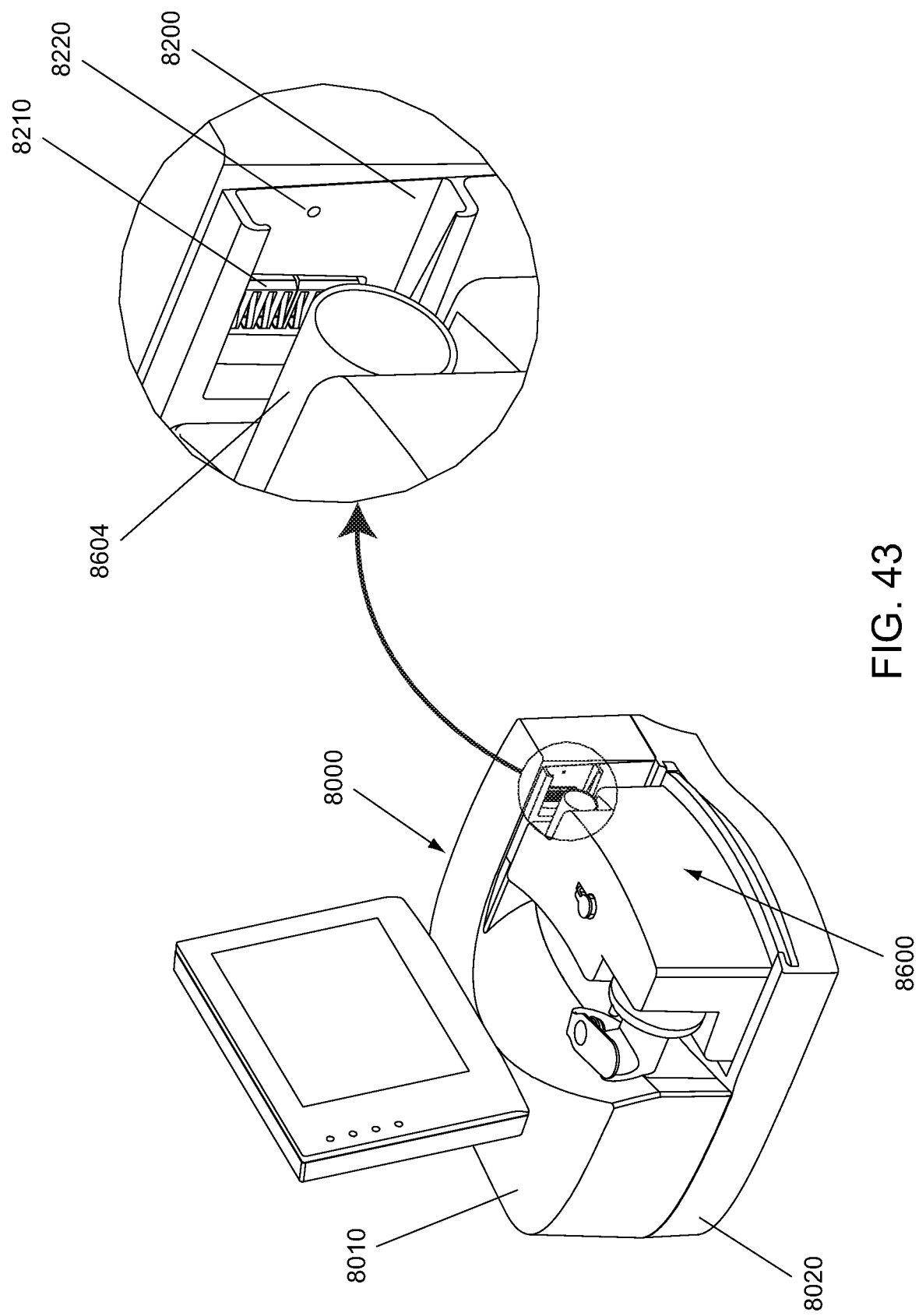
FIG. 43 illustrates a receiving area for a first connector of a delivery circuit according to an embodiment of the present disclosure.
Figure 44:
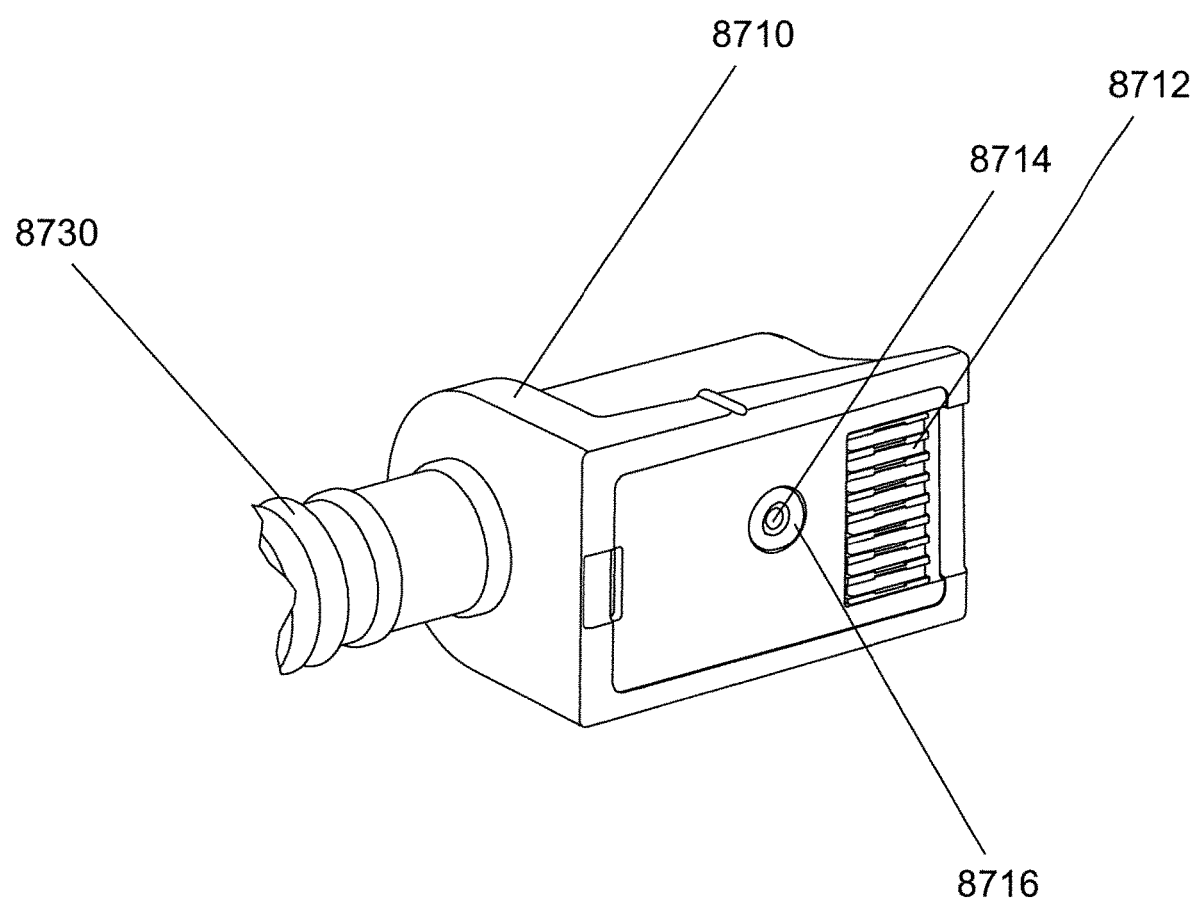
FIG. 44 illustrates the first connector of the delivery circuit according to an embodiment of the present disclosure.
Figure 45:
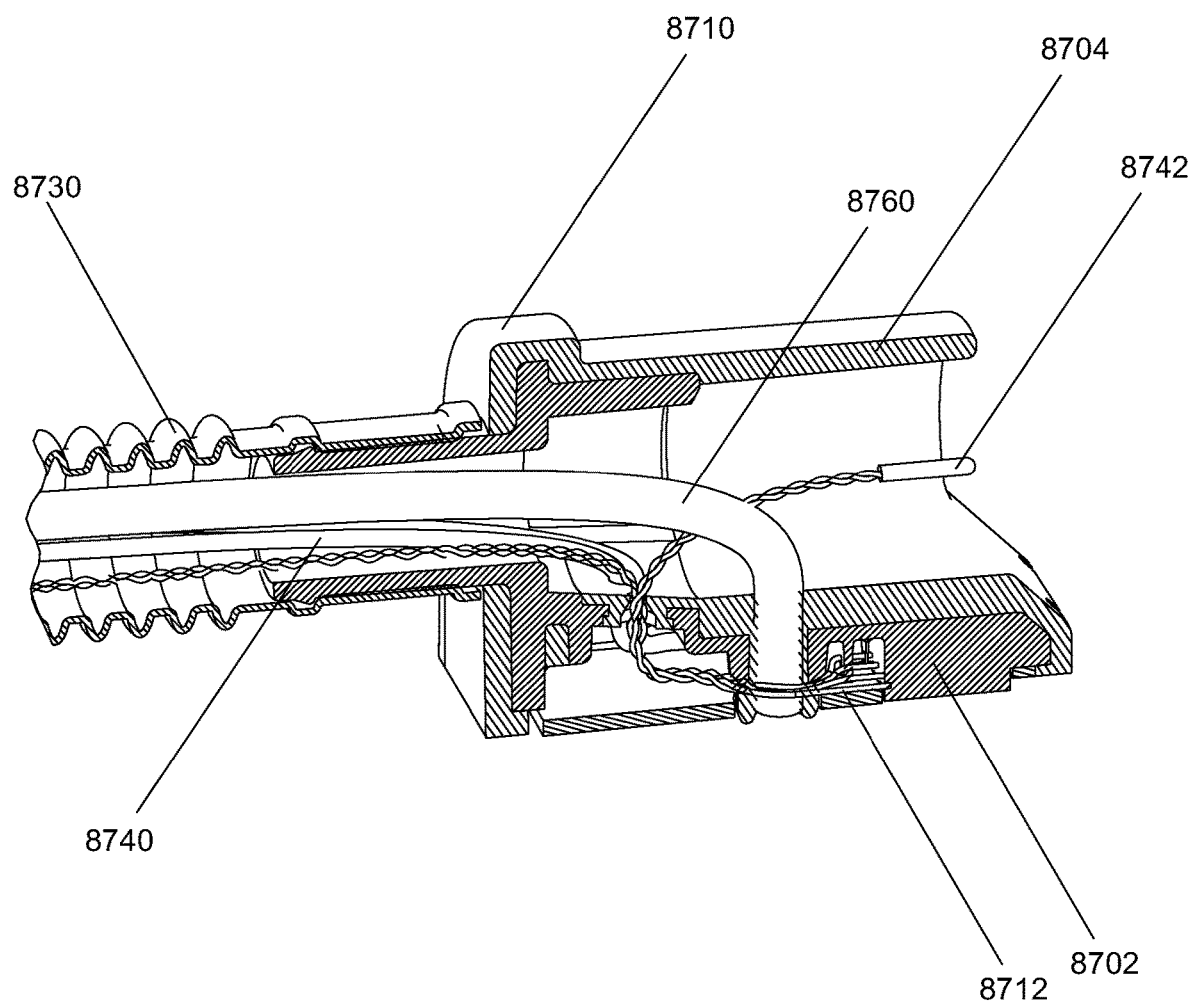
FIG. 45 illustrates a perspective sectional view of the first connector end of the delivery circuit according to an embodiment of the present disclosure.

The delivery circuit 8700 can have a first connector 8710, a second connector 8720, and a tube 8730 (e.g. a corrugated tube) there between. The first connector 8710 can connect the delivery circuit 8700 to the water chamber 8600. FIG. 45 illustrates a perspective sectional view of an embodiment of first connector end and the tube 8730 of the delivery circuit 8700. The first connector 8710 may have a body that is rigid (e.g. rigid portion 8702) and provides structure, such as a plastic, and that houses first connector electrical contacts 8712. The first connector electrical contacts 8712 may be integrally molded into the body. Alternatively, the body may be flexible, have a flexible portion (e.g. by overmolding), or have a flexible portion (e.g. flexible portion 8704) that is coupled with the rigid portion 8702. The first connector 8710 (or its flexible portion) can facilitate sealing and/or coupling the first connector 8710 with the water chamber 8600 (e.g., at water chamber gas outlet 8604). The first connector (or its flexible portion) can facilitate coupling the delivery circuit 8700 to the enclosure of the HFT device. For example, the first connector 8710 (or its flexible portion) conforms to a mating socket 8200 in the enclosure of the HFT device 8000 to provide a snug, secure mechanical engagement. FIG. 43 illustrates mating socket 8200, contacts 8210, and sensor port 8220 of HFT device 8000, as well as water chamber gas outlet 8604 of water chamber 8600. FIG. 44 illustrates first connector 8710, first connector contacts 8712, first connector sensor port 8714, and first connector o-ring of delivery circuit 8700. The delivery circuit 8700 may couple with the HFT device 8000 or the water chamber 8600 via a friction fit. The first connector 8710 (through either the rigid portion or the flexible portion) can provide a hand-grip for the user to insert or remove the delivery circuit 8700 from the water chamber 8600 and/or the HFT device 8000.

The delivery circuit 8700 can also have a long, flexible sensing conduit (e.g., sensing conduit 8760) (and/or or a sampling conduit in other embodiments) that is internal to the delivery circuit (i.e. routed through the annular flow path through the tube 8730). In an alternate embodiment, the sensing conduit 8760 may be external (but possibly coupled) to the delivery circuit 8700. In another alternate embodiment, the tube 8730 could be a multiple lumen tube where a first lumen is the gas delivery path, a second lumen is the sensing conduit (or a sampling conduit), and possibly a third lumen is a sampling conduit. The sensing conduit 8760 (via a first connector sensor port 8714) can pneumatically connect the HFT device (via a sensor port 8220 on its enclosure) to the distal end of the patient interface (e.g. distal end of second conduit 8820). The use of a sensing conduit (or sampling conduit) can allow all electrical sensing components required for signal processing to remain inside the HFT device with the other electronics, rather than having electrical sensing components in one of the disposable components (e.g. on the distal end of the patient interface).

When the delivery circuit 8700 is coupled with the HFT device 8000, a seal can be created between the sensor port 8220 on the HFT device and the first connector sensor port 8714 in the delivery circuit 8700. The delivery circuit or the HFT device may have a seal (e.g. first connector o-ring 8716) to facilitate this seal. When the delivery circuit is coupled with the enclosure of HFT device, the first connector contacts 8712 on the delivery circuit can engage with contacts 8210 on the HFT device 8000. This electrical engagement can enable the control of the thermal components in the delivery circuit 8700 by the software of the HFT device to maintain the desired temperature and humidity parameters of the gas. The delivery circuit 8700 may also have at least two temperature sensors (e.g. thermistors) internally. A first thermistor 8742 can be located near the first connector 8710 and a second thermistor 8744 can be located near the second connector 8720. The thermistors can provide temperature feedback to the main PCB 8060 via the electrical contact engagement between the delivery circuit 8700 and the HFT device. The heated wire 8740 is powered by the HFT device via the electrical contact engagement between the delivery circuit 8700 and the HFT device.

Figure 46:
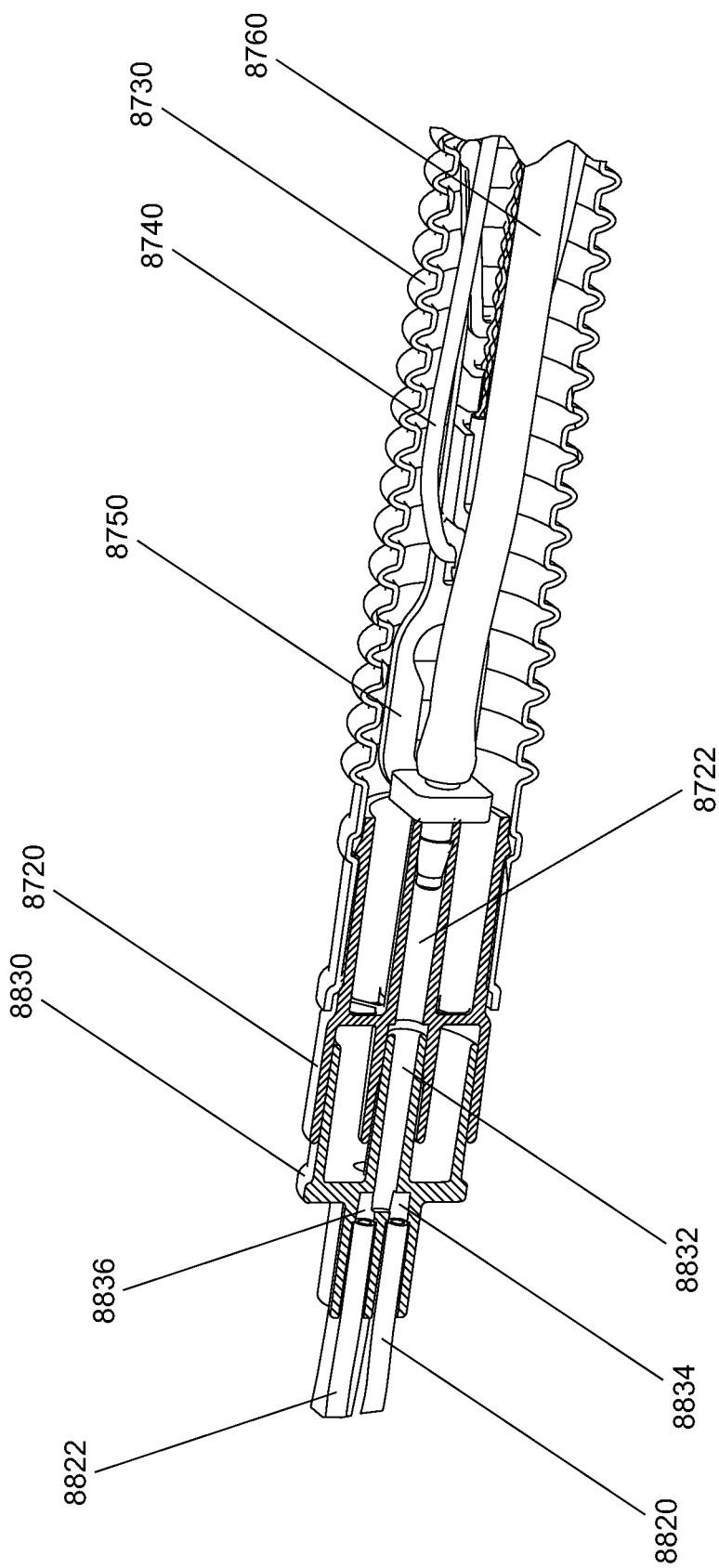
FIG. 46 illustrates a first perspective sectional view of a second connector the delivery circuit and patient fitting of the patient interface according to an embodiment of the present disclosure.
Figure 47:
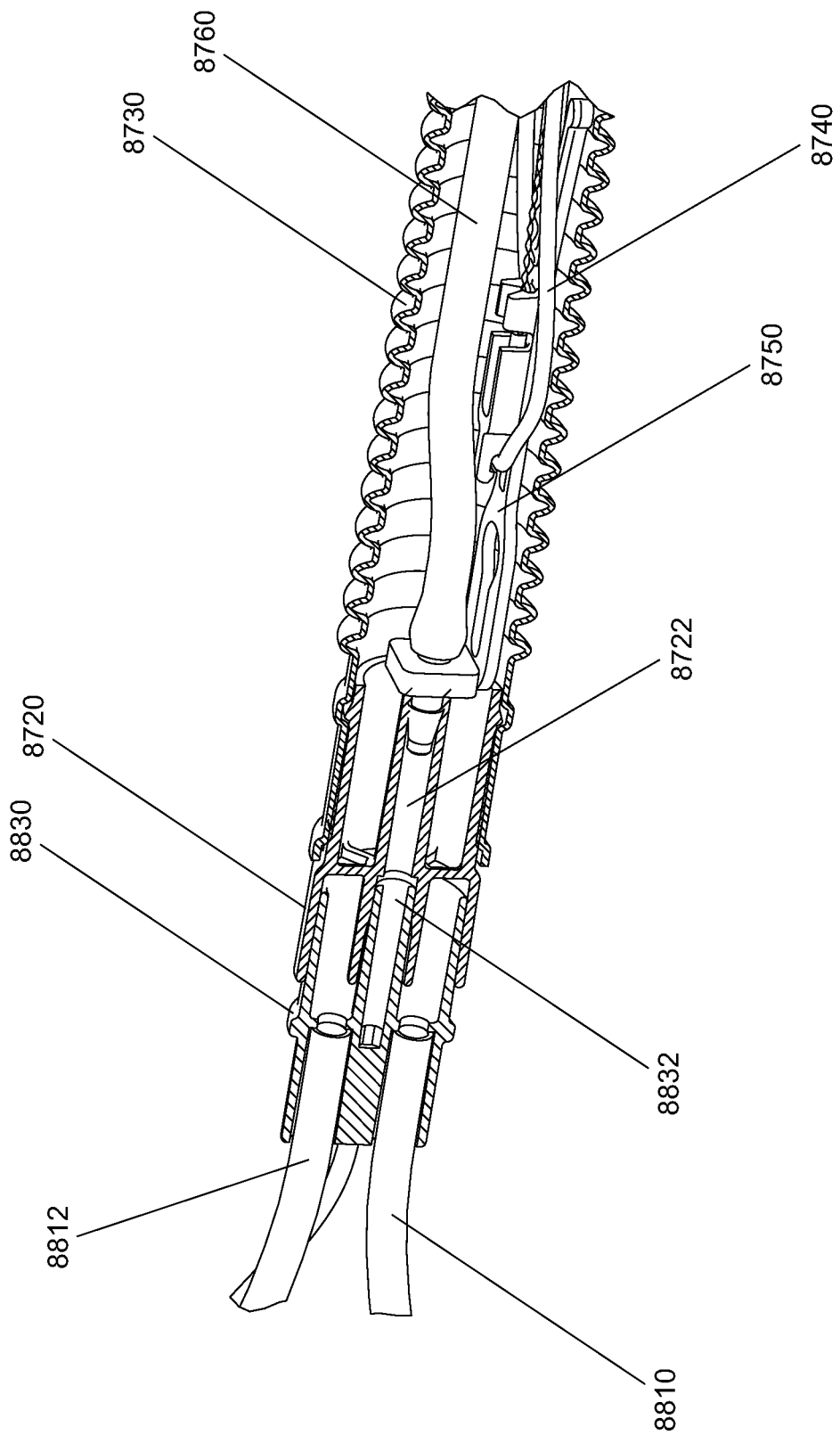
FIG. 47 illustrates a second perspective sectional view of a second connector the delivery circuit and patient fitting of the patient interface according to an embodiment of the present disclosure.
Figure 48:
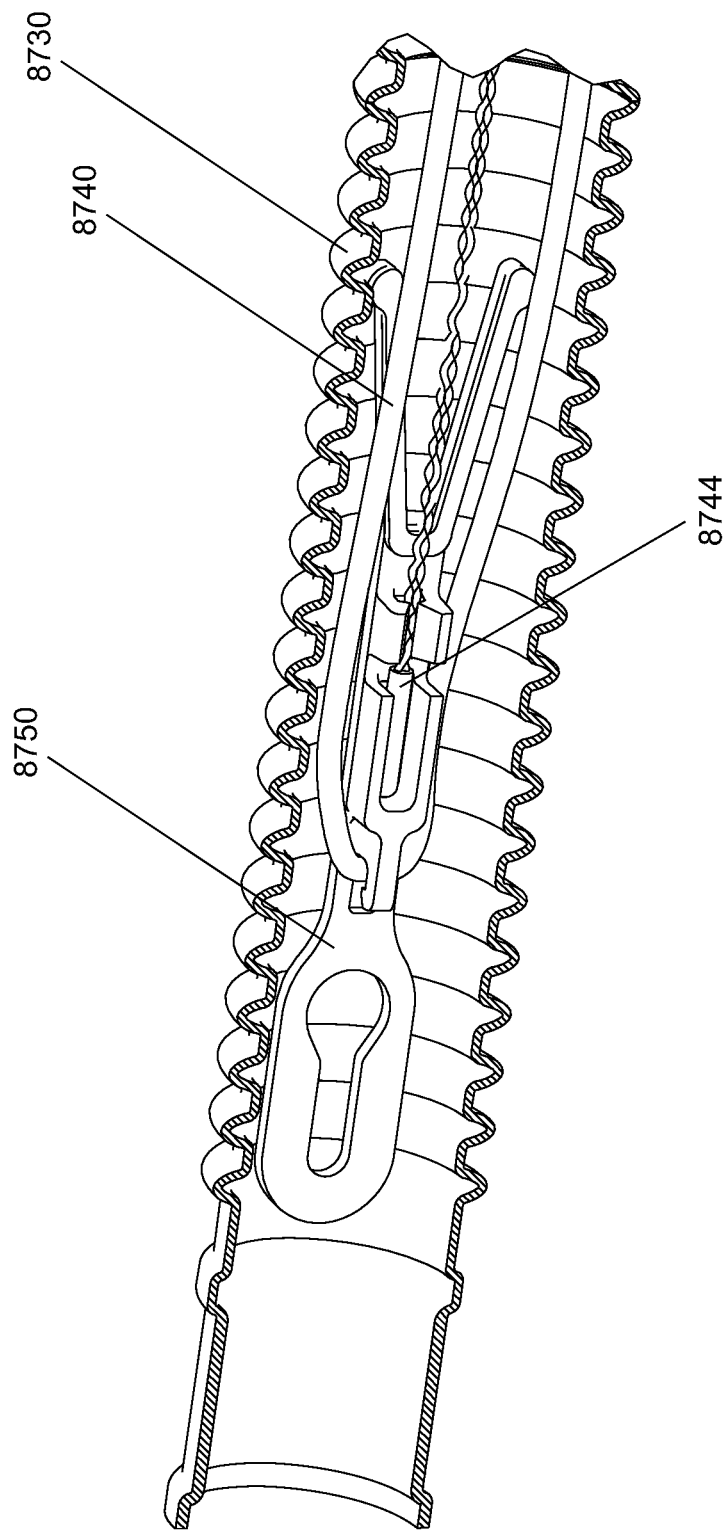
FIG. 48 illustrates a perspective sectional view of the delivery circuit at the second connector end with the second connector and sensing conduit removed, according to an embodiment of the present disclosure.

FIG. 46 illustrates a first perspective sectional view of an embodiment of the second connector end of the delivery circuit 8700 and the patient fitting end of the patient interface. FIG. 47 illustrates a second perspective sectional view of an embodiment of a second connector end of the delivery circuit 8700 and a patient fitting end of the patient interface. FIG. 48 illustrates a perspective sectional view of an embodiment of the second connector end of the delivery circuit 8700 with the second connector and the sensing conduit removed to show some of the internal components. The delivery circuit 8700 can have a holder 8750 internal and near the second connector 8720. The holder 8750 can couple with the second thermistor 8744 and/or the heated wire 8740. The holder 8750 can provide a means for pulling during assembly the second thermistor 8744 and/or the heated wire 8740 through the delivery circuit 8700 towards the second connector 8720. The holder 8750 can maintain a specific distance between the heated wire 8740 and the second thermistor 8744 to ensure that the gas temperature reading by the second thermistor 8744 is not influenced or made inaccurate by the temperature of the heated wire 8740. The heated wire 8740 can bend or wrap around the holder 8750 to facilitate the return of the heated wire 8740 back to the first connector 8710. The holder 8750 can couple to the tube 8730, for example by having a protrusion (i.e. a ring or partial ring) that inserts into at least one of the corrugations on the tube 8730 or can couple with the second connector 8720. The holder 8750 can provide a means for positioning the holder 8750 at a specific location within the tube 8730 or a certain distance from the second connector 8720. The second connector 8720 can have a port (e.g., second connector sensor port 8722) to connect the sensing conduit 8760.

Figure 49:
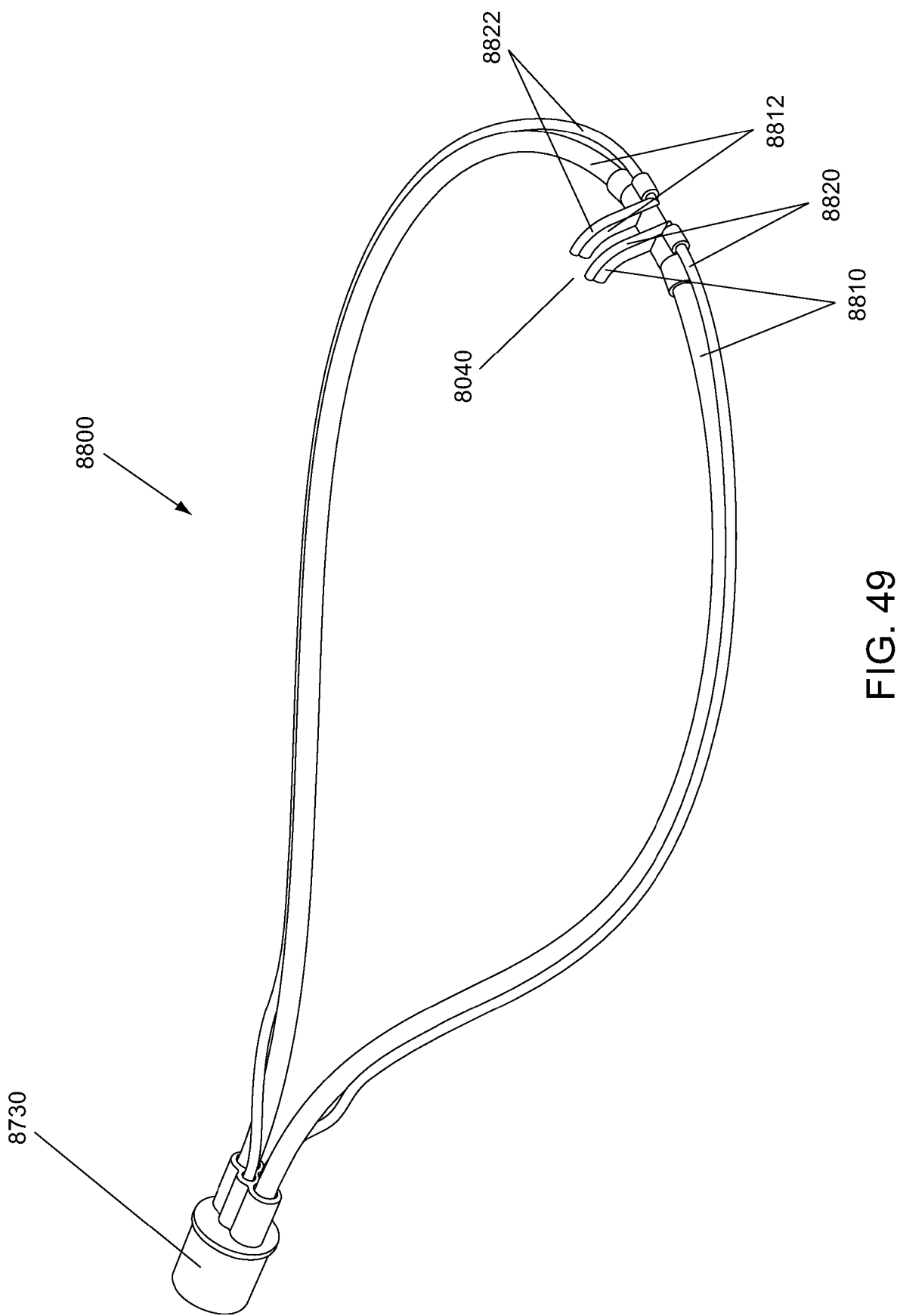
FIG. 49 illustrates the patient interface according to an embodiment of the present disclosure.

The patient interface, such as patient interface 8800, may have a nasal cannula portion 8840 that is intended to enter the nasal passages. The patient interface 8800 may have a first conduit 8810 for delivering the respiratory gas. The patient interface 8800 may have a second conduit 8820 for sensing or sampling (e.g. collecting pressure data in the nasal passages via the nasal cannula portion 8840). As shown in FIG. 49, first conduit 8810 and second conduit 8820 may extend through the nasal cannula portion 8840. In a preferred embodiment, patient interface 8800 may have a two first conduits 8810, 8812 as shown in FIG. 49. In one embodiment, patient interface 8800 may have a two second conduits 8820, 8812 as shown in FIG. 49. The patient interface 8800 may mechanically and fluidly couple with the delivery circuit 8700 via a friction fit. The patient interface 8800 may have a patient fitting 8830 that may couple with the second connector 8720 to allow for the delivery of the respiratory gas through patient fitting 8830 and to a first conduit (e.g. first conduits 8810, 8812) as shown in FIG. 47. When the patient interface 8800 is coupled with the delivery circuit 8700, a seal can be created between the sensing conduit 8760 (via second connector sensor port 8722) in the delivery circuit and a patient fitting sensing conduit 8832 in the patient fitting as shown in FIG. 46. The patient fitting sensing conduit 8832 in the patient fitting pneumatically couples or communicates with a second conduit (e.g., second conduits 8820, 8822). Therefore, the second conduit can be in communication with the sensor port 8220 on the HFT device. The patient interface 8800 can be described as a sensing-enabled nasal cannula patient interface. In one embodiment shown in FIG. 46, the patient fitting sensing conduit 8832 in the patient fitting 8830 can split into two fitting sensing conduits 8834, 8836 which can pneumatically couple with two second conduits 8820, 8822. As shown in FIG. 46 and FIG. 47, first conduit 8810 may have a larger bore than the bore of second conduit 8820. The nasal cannula portion 8840 and the patient fitting 8830 can be connected by one or more patient tubes. A patient tube may be single or double lumen tube. A double lumen patient tube may have a first lumen for gas delivery and a second lumen for sensing or sampling.

The main PCB 8060 of the HFT device may have a sensor 8064 for taking measurements at or proximal the outlet of the patient interface. In one embodiment, the sensor 8064 can be a pressure sensor for measuring the airway pressure of the user. In this embodiment, the delivery circuit and the patient interface can have a conduit system that communicates with the pressure sensor. This would allow the HFT system to monitor and/or control pressure. In an alternate embodiment, the sensor 8064 can be for sampling the gas at or proximal the outlet of the patient interface. For example, the gas exhaled by the user may be sampled for $CO_2$ content. In a similar manner to the pressure sensor embodiment, the delivery circuit and the patient interface would have a conduit system that communicates with the sensor 8064 for sampling.

Different versions of delivery circuit can couple with the HFT device. As mentioned throughout, a delivery circuit can have thermal, electrical, temperature sensing, pressure sensing, and/or gas sampling capabilities and/or conduits in addition to its gas delivery function. The HFT device can be configured to recognize what type of delivery circuit is being connected to the device. For example, when a delivery circuit with gas delivery, electrical, and pressure sensing capabilities is connected, the HFT device could recognize this type of delivery circuit and consequently activate the pressure sensing aspects of the HFT device, such as pressure sensing graphics, alarms, etc. Different delivery circuits with different capabilities then could serve to activate different and various functionality of the HFT device, which may exist in the HFT device but be dormant or inactive depending on the delivery circuit connected. The HFT device may have mechanical, electrical, or optical means for recognizing the delivery circuit type connected. In one embodiment, the delivery circuit may depress certain switch on the HFT device or may contact certain electrical contacts on the HFT device. In another embodiment, the HFT device may optically read a certain delivery circuit or may scan a feature (e.g. a barcode or serial number) on a certain delivery circuit. In one example, if an operator tried to connect a delivery circuit not authorized or compatible with the HFT device (e.g. a delivery circuit connected to a sealed patient interface), the HFT device may be programmed to have limited function or not function at all. In an alternate example, if an operator tried to connect a delivery circuit connected to a sealed patient interface, the HFT device may be programmed to switch to a bi-level or Bi-PAP mode (e.g. pressure based mode) instead of an HFT mode (e.g. flow based mode) and actually allow use with a sealed mask like a CPAP, Bi-PAP, or a ventilator.

The disposable components, such as the outlet filter 8090, water chamber 8600, delivery circuit 8700, and patient interface 8800, may be individually removed from the HFT device system after use. Alternatively, groups of these disposable devices may be removed at the same time. For example, the outlet filter may be decoupled from the HFT device in one motion to disengage the water chamber, delivery circuit, and patient interface at the same time. This is advantageous to simplify the disassembly, as well as to minimize the amount of water or other contents in the disposable components that may be inadvertently leaked into the environment during disassembly.

The HFT device may further serve as a diagnostic device either during its typical HFT use or while it not being used for typical HFT treatment. The HFT device could utilize the previously mentioned sensing capabilities (e.g. pressure sensing, gas sampling, etc.) for diagnostic applications. For example, the HFT device may be used to diagnosis respiratory alignments such as sleep apnea. The HFT device could monitor, measure, record, and output the necessary information. The HFT device could incorporate functionality or accessories to include determination of stage of sleep, for example via electroencephalogram (EEG), electro-oculogram (EOG), submental electromyogram (EMG) and/or electrocardiogram/heart rate (ECG). The HFT device could incorporate functionality or accessories to include sleep parameters such as airflow, respiratory movement/effort, oxygen saturation (e.g. by oximetry), snoring, pulse rate, head movement, head position, limb movement, actigraphy, and/or peripheral arterial tone. Diagnostic accessories coupled with the HFT device could include a body sensors, pulse oximeter, a wearable wrist device, a chest or abdomen band or belt, headgear, thermistor, nasal cannula, and/or nasal/oral oral cannula, any of these which may have integrated sensors or sensing technology.

The HFT device may receive information (e.g. software upgrades) via a wired connection, USB, memory card, fiber optic, wireless connection, blue tooth, Wi-Fi, etc. The HFT device may send information (e.g. patient reports) via similar communication means. The HFT device may include wired connection such as USB port 8066 or memory card, or a wireless connection such as blue tooth or Wi-Fi.

The bulk of the work of heating the respiratory gas can be done by the heater 8052 (e.g. PTC heater element) that is part of the HFT device. This heater 8052 can be concealed by a heater plate 8050 (e.g. stainless steel material) of the HFT device, which may be in direct contact with the heat transfer plate (e.g. aluminum material) of the water chamber 8600 during use. During the heating process, the duty cycle of the heater 8052 and/or the heated wire 8740 is precisely and continuously adjusted by the HFT device's embedded software in response to feedback supplied by a temperature sensor 8054 that is located near the heater 8052 (and in some embodiments may be in contact with the heater plate 8050) and/or in response to the feedback supplied by the thermistors (e.g., first thermistor 8742, second thermistor 8744) in the delivery circuit 8700.

The HFT device may periodically decrease the gas flow rate from the set gas flow rate to allow the lungs to temporarily return to a more normal resting volume. The HFT device may automatically lower the gas flow by a certain percentage or by a certain value from the set gas flow value for a specific amount of time over a certain frequency or time period. For example, the HFT device may automatically lower the gas flow by a 20% or by 5 L/min for five seconds every ten minutes. Alternatively, the HFT device may automatically adjust the gas flow by a certain percentage, by a certain value, or a certain multiple of the expected patient tidal volume, for example based on age, weight, and/or BMI. For example, the gas flow may be decreased automatically by the HFT device to less than two times the patient expected tidal volume for five seconds every twelve breathing cycles. These types of periodic deviations from set gas flow rates could be inputted by the operator via the GUI or may be part of the programmed software. In an alternate embodiment, the HFT system may be used as a bubble CPAP system. The patient interface may have an expiratory tube connected to the nasal cannula portion for gas to exit. The distal end of the expiratory tube may be immersed in a water tank. In one embodiment, the water chamber may serve as the water tank. In an alternate embodiment, the water chamber may have a first water compartment that is fluidically coupled with the HFT device and the delivery circuit and a second water compartment that is fluidically coupled with the expiratory tube only and serves as the water tank. Water is placed in the water tank. The depth to which the expiratory tube is immersed underwater can determine the pressure generated in the airway of the patient. The gas flow may flow through the expiratory tube and bubble out into the water tank. The patient interface may be a sealed interface. The pressure sensing technology of the HFT system described throughout can be used to verify that the patient is receiving the desired pressure when the HFT system is being used as a bubble CPAP system or any embodiment described throughout. Automatic filling system technology described previously could be applied to the water tank.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. For example, although the embodiment shown in FIG. 1 shows each nasal insert 125, 130 having two inlets 152, 154, in alternative embodiments of the invention, one or more of the nasal inserts 125, 130 may have more or less than two inlets (and/or more or less than two sensors). Further, sensors such as sensor 2120 may be situated or in communication with any area of the airway or with an artificial airway (such as that described in Provisional Application Ser. No. 61/004,746 filed on Nov. 29, 2007), and is not limited to sensing the environment of the anterior nares. Although specific terms are employed herein, they are used in a generic and descriptive sense only and not for purposes of limitation.

We claim:

1. A high flow therapy system for delivering heated and humidified respiratory gas to an airway of a patient, the high flow therapy system comprising:
   a high flow therapy device including a microprocessor;
   a first inlet configured to receive a first gas;
   a valve in electrical communication with the microprocessor, the valve coupled to the first inlet and configured to adjust an amount of the first gas that flows from the first inlet;
   a second inlet configured to receive a second gas;
   a blower coupled to the second inlet;
   a respiratory gas flow pathway for delivering the respiratory gas to the airway of the patient by way of a non-sealing respiratory interface, wherein flow rate of the respiratory gas is controlled by the microprocessor of the high flow therapy device adjusting the speed of the blower as the second gas flows toward the blower from the second inlet;
   a mixing area for mixing the first gas and the second gas in the respiratory gas flow pathway;
   a humidification area configured for humidifying respiratory gas in the respiratory gas flow pathway; and
   a heated delivery conduit for minimizing condensation of humidified respiratory gas,
   wherein the high flow therapy device is adapted to affect temperature within the humidification area and temperature within the heated delivery conduit.

2. The high flow therapy system of claim 1, further comprising a drive pressure sensor.

3. The high flow therapy system of claim 1, further comprising a relief valve.

4. The high flow therapy system of claim 1, wherein the system is configured to allow for measurement of oxygen concentration of the respiratory gas.

5. The high flow therapy system of claim 1, further comprising an outlet filter operationally coupled to the respiratory gas flow pathway.

6. The high flow therapy system of claim 1, further comprising a safety component coupled to an outlet of the high flow therapy device.

7. The high flow therapy system of claim 1, wherein the humidification area is configured to impede water from entering the high flow therapy device.

8. The high flow therapy system of claim 1, wherein the humidification area is configured to impede water from entering the heated delivery conduit.

9. The high flow therapy system of claim 1, wherein the humidification area is configured to allow for automatic filling of water.

10. The high flow therapy system of claim 1, wherein at least one of respiration rate, tidal volume, and minute volume are calculated by the microprocessor.

11. The high flow therapy system of claim 1, wherein the microprocessor is configured to control at least one of temperature of the gas, humidity of the gas, mixture of the gas, the flow rate of the gas, and volume of the gas delivered to the patient.

12. The high flow therapy system of claim 1, wherein the system is configured to control the flow rate of the respiratory gas delivered to the patient based on a respiratory phase of the patient during use.

13. The high flow therapy system of claim 1, wherein the system is configured to deliver the respiratory gas to the patient at different airway pressures based on a respiratory phase of the patient during use.

14. A high flow therapy system for delivering heated and humidified respiratory gas to an airway of a patient, the system comprising:
- a high flow therapy device including a microprocessor;
- a first inlet configured to receive a first gas;
- a valve in electrical communication with the microprocessor, the valve coupled to the first inlet and configured to adjust an amount of the first gas that flows from the first inlet;
- a second inlet configured to receive a second gas;
- a blower coupled to the second inlet;
- a respiratory gas flow pathway for delivering the respiratory gas to the airway of the patient by way of a non-sealing respiratory interface, wherein flow rate of the respiratory gas is controlled by the microprocessor of the high flow therapy device adjusting the speed of the blower as the second gas flows toward the blower from the second inlet;
- a mixing area for mixing the first gas and the second gas in the respiratory gas flow pathway;
- a humidification area configured for humidifying respiratory gas in the respiratory gas flow pathway;
- a heated delivery conduit for minimizing condensation of humidified respiratory gas; and
- a touchscreen adapted to allow an operator to make inputs to the high flow therapy device.

15. The high flow therapy system of claim 14, wherein the touchscreen is coupled with a display that can be rotated.

16. The high flow therapy system of claim 14, wherein the touchscreen is coupled with a display that can tilted.

17. The high flow therapy system of claim 14, wherein the touchscreen is coupled with a display that is removable.

18. A high flow therapy system for delivering heated and humidified respiratory gas to an airway of a patient, the system comprising:
- a high flow therapy device including a microprocessor;
- a first inlet configured to receive a first gas;
- a proportional valve in electrical communication with the microprocessor, the proportional valve coupled to the first inlet and configured to adjust an amount of the first gas that flows from the first inlet;
- a second inlet configured to receive a second gas;
- a blower coupled to the second inlet;
- a respiratory gas flow pathway for delivering the respiratory gas to the airway of the patient by way of a non-sealing respiratory interface, wherein flow rate of the respiratory gas is controlled by the microprocessor of the high flow therapy device adjusting the speed of the blower as the second gas flows toward the blower from the second inlet;
- a mixing area for mixing the first gas and the second gas in the respiratory gas flow pathway;
- a humidification area configured for humidifying respiratory gas in the respiratory gas flow pathway; and a heated delivery conduit for minimizing condensation of humidified respiratory gas,
- wherein the respiratory gas exits the humidification area without reentering the high flow therapy device.

* * * * *